(12) United States Patent
Moriguchi

(10) Patent No.: US 12,279,824 B2
(45) Date of Patent: Apr. 22, 2025

(54) OPHTHALMIC APPARATUS

(71) Applicant: Topcon Corporation, Tokyo (JP)

(72) Inventor: Yoshikiyo Moriguchi, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 562 days.

(21) Appl. No.: 17/679,085

(22) Filed: Feb. 24, 2022

(65) Prior Publication Data

US 2022/0175246 A1 Jun. 9, 2022

Related U.S. Application Data

(63) Continuation of application No. PCT/JP2020/030732, filed on Aug. 12, 2020.

(60) Provisional application No. 62/898,753, filed on Sep. 11, 2019.

(51) Int. Cl.
*A61B 3/135* (2006.01)
*A61B 3/00* (2006.01)
*A61B 3/10* (2006.01)

(52) U.S. Cl.
CPC .......... *A61B 3/135* (2013.01); *A61B 3/0008* (2013.01); *A61B 3/102* (2013.01)

(58) Field of Classification Search
CPC ....... A61B 3/135; A61B 3/0008; A61B 3/102; A61B 3/0025; A61B 3/1025
USPC ........................................................ 351/221
See application file for complete search history.

(56) References Cited

U.S. PATENT DOCUMENTS

| | | | |
|---|---|---|---|
| 4,854,692 A | * | 8/1989 | Kobayashi ........... A61B 3/1025 351/221 |
| 7,331,669 B2 | | 2/2008 | Elsner |
| 7,831,106 B2 | | 11/2010 | Elsner et al. |
| 8,237,835 B1 | | 8/2012 | Muller |

(Continued)

FOREIGN PATENT DOCUMENTS

| | | |
|---|---|---|
| EP | 3738501 A1 | 11/2020 |
| JP | 861-293430 A | 12/1986 |

(Continued)

OTHER PUBLICATIONS

Ueno Tokio et al. Ophthalmologic Imaging Device; JP 2017029483 (Year: 2017).*

(Continued)

*Primary Examiner* — Tuyen Tra
*Assistant Examiner* — Rahman Abdur
(74) *Attorney, Agent, or Firm* — XSENSUS LLP

(57) ABSTRACT

An ophthalmic apparatus includes an irradiation optical system, an optical scanner, an optical splitting and combining unit, and a detector. The irradiation optical system includes a light source and is configured to generate measurement light using light from the light source. The optical scanner is configured to deflect the measurement light and to guide the deflected measurement light to a subject's eye. The optical splitting and combining unit is configured to guide the measurement light to the optical scanner and to generate interference light between reference light that is generated from the light from the light source and returning light of the measurement light from the subject's eye. The detector is configured to detect the returning light and the interference light via the optical splitting and combining unit.

26 Claims, 38 Drawing Sheets

(56) References Cited

U.S. PATENT DOCUMENTS

| | | |
|---|---|---|
| 8,488,895 B2 | 7/2013 | Muller et al. |
| 10,441,167 B2 | 10/2019 | Bublitz et al. |
| 2007/0263171 A1 | 11/2007 | Ferguson et al. |
| 2010/0073634 A1 | 3/2010 | Ferguson et al. |
| 2010/0166293 A1 | 7/2010 | Sugita et al. |
| 2011/0085136 A1 | 4/2011 | Ferguson et al. |
| 2012/0062843 A1 | 3/2012 | Ferguson et al. |
| 2012/0293770 A1 | 11/2012 | Hirose |
| 2014/0176903 A1 | 6/2014 | Qiu et al. |
| 2014/0247427 A1 | 9/2014 | Ferguson et al. |
| 2015/0085252 A1 | 3/2015 | Fujimura et al. |
| 2016/0345822 A1 | 12/2016 | Fujimura et al. |

FOREIGN PATENT DOCUMENTS

| | | |
|---|---|---|
| JP | 2009-535164 A | 10/2009 |
| JP | 2010-259495 A | 11/2010 |
| JP | 2011-161007 A | 8/2011 |
| JP | 2013-248376 A | 12/2013 |
| JP | 2015-221091 A | 12/2015 |
| JP | 2016-500327 A | 1/2016 |
| JP | 2017-29483 A | 2/2017 |
| JP | 2019-118720 A | 7/2019 |

OTHER PUBLICATIONS

Office Action issued on Oct. 4, 2022, in corresponding Japanese patent Application No. 2021-545177, 10 pages.

Extended European Search Report issued Sep. 8, 2023 in European Patent Application No. 20862583.0, 11 pages.

International Search Report and Written Opinion mailed on Sep. 29, 2020, received for PCT Application PCT/JP2020/030732, Filed on Aug. 12, 2020, 11 pages including English Translation.

Fechtig et al., "Line-field Parallel Swept Source MHz OCT for Structural and Functional Retinal Imaging", Biomedical Optics Express, Mar. 1, 2015, vol. 6, No. 3, 20 pages.

* cited by examiner

OPHTHALMIC APPARATUS

CROSS-REFERENCE TO RELATED APPLICATIONS

The present application is a continuation application of International Patent Application No. PCT/JP2020/030732, filed Aug. 12, 2020, which claims priority to U.S. Provisional Japanese Patent Application No. 62/898,753, filed Sep. 11, 2019. The contents of these applications are incorporated herein by reference in their entirety.

FIELD

The disclosure relates to an ophthalmic apparatus.

BACKGROUND

In recent years, screening tests have been performed using ophthalmic apparatuses. Such ophthalmic apparatuses are expected to be applied to self-examinations, and further downsizing and weight saving of the ophthalmic apparatuses are desired. In contrast, for detailed observation of the site of interest in the subject's eye, it is effective to acquire a plurality of images in that the site of interest is depicted from various perspectives.

For example, U.S. Pat. Nos. 7,831,106, 8,237,835, and U.S. patent Ser. No. 10/441,167 disclose an ophthalmic apparatus configured to pattern-illuminate a subject's eye using slit light and to detect returning light of the slit light using CMOS (Complementary Metal Oxide Semiconductor) image sensor. This ophthalmic apparatus can acquire images of the subject's eye with a simple configuration, by adjusting the illumination pattern and the timing of light receiving timing using the CMOS image sensor.

In particular, U.S. Pat. No. 8,237,835 and U.S. patent Ser. No. 10/441,167 disclose an ophthalmic apparatus including an optical system that combines optical coherence tomography optical system with an optical system for acquiring images of the subject's eye pattern-illuminated with slit light.

For example, "Line-field parallel swept source MHz OCT for structural and functional retinal imaging" (Daniel J. Fechtig et al., BIOMEDICAL OPTICS EXPRESS, Feb. 2, 2015, Vol. 6, No. 3, p. 716-735) discloses a method of performing optical coherence tomography using line-shaped measurement light.

SUMMARY

One aspect of embodiments is an ophthalmic apparatus, including: an irradiation optical system including a light source and configured to generate measurement light using light from the light source; an optical scanner configured to deflect the measurement light and to guide the deflected measurement light to a subject's eye; an optical splitting and combining unit configured to guide the measurement light to the optical scanner and to generate interference light between reference light that is generated from the light from the light source and returning light of the measurement light from the subject's eye; and a detector configured to detect the returning light and the interference light via the optical splitting and combining unit.

Another aspect of the embodiments is an ophthalmic apparatus, including: an irradiation optical system including a light source and configured to generate measurement light using light from the light source; an optical scanner configured to deflect the measurement light; an optical splitting and combining unit configured to guide the measurement light deflected by the optical scanner to a subject's eye and to generate interference light between reference light that is generated from the light from the light source and returning light of the measurement light from the subject's eye; and a detector configured to detect the returning light and the interference light via the optical splitting and combining unit.

DETAILED DESCRIPTION

Figure 1:
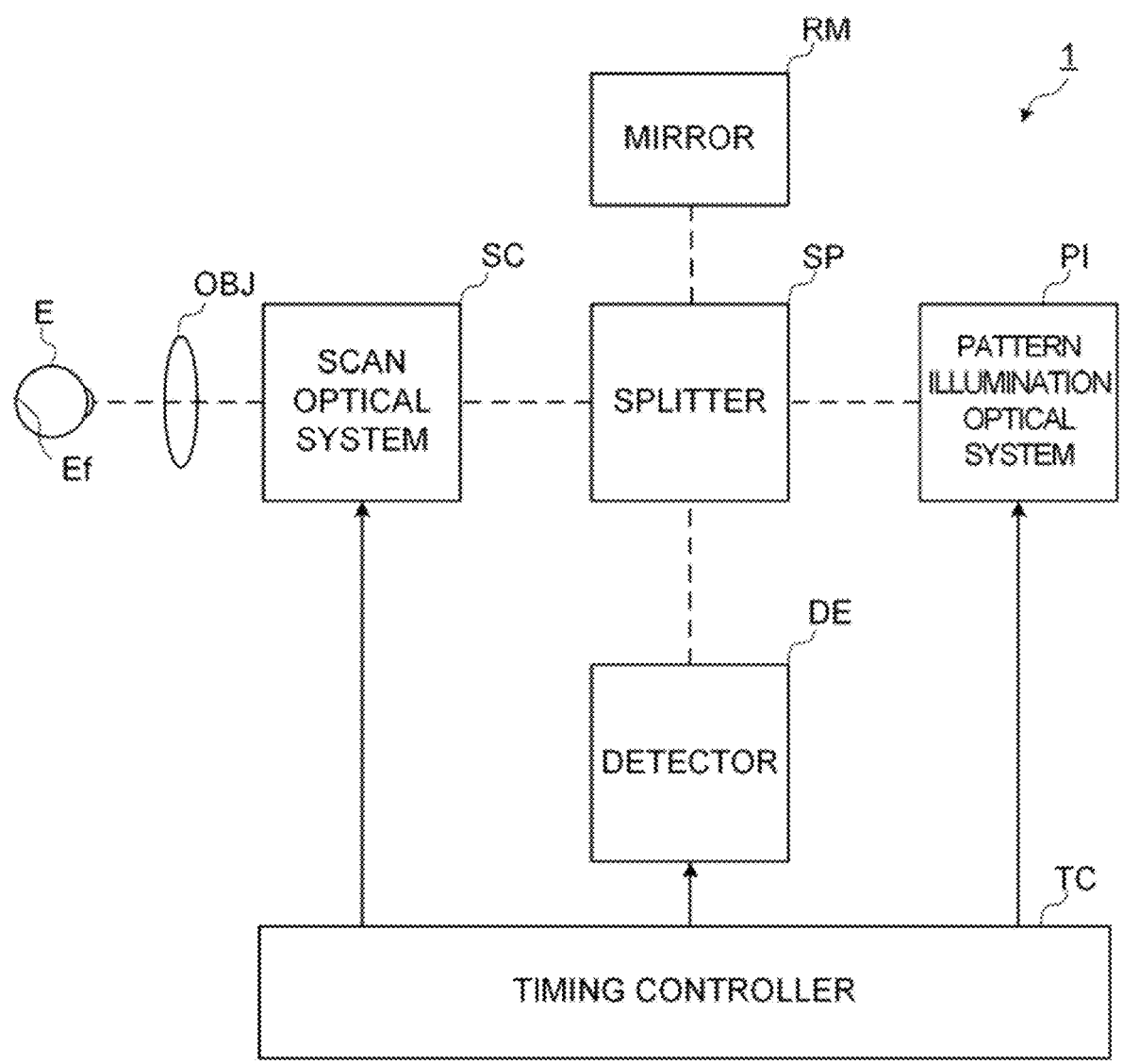
FIG. 1 is a schematic diagram illustrating an example of a configuration of an ophthalmic apparatus according to a first embodiment.

In the conventional methods, when the subject's eye is a microcoria, it is known that the amount of light entering the eye decreases and the acquired image of the subject's eye (especially in the center) becomes darker. Thus, this may lead to a decrease in the accuracy of the measurement signal and deterioration of the image quality, making it difficult to observe the subject's eye in detail.

In addition, even if the optical system for acquiring the front image (or measurement signal) of the subject's eye is simply combined with the optical system for acquiring the tomographic image (or measurement signal) of the subject's eye, the apparatus will increase in size and the complexity of control.

According to some embodiments according to the present invention a new technique for observing a subject's eye in detail with a simple configuration can be provided.

Referring now to the drawings, exemplary embodiments of an ophthalmic apparatus according to the present invention are described below. The contents of the document cited in the present specification can be appropriately incorporated as contents of the following embodiments.

In this specification, the term "splitter" means an optical element or an optical system that splits incident light into two light by splitting the power at a predetermined splitting ratio, an optical element or an optical system that splits incident light having a plurality of wavelength components different from each other into light having two wavelength ranges different from each other, or an optical element or an optical system that splits incident light into two light in a time division. For example, the "splitter", that splits the incident light at a split ratio of 50:50, realizes the function of a half mirror (beam splitter). For example, the "splitter", that splits the incident light in wavelength, realizes the function of a dichroic beam splitter. For example, the "splitter", that splits the incident light in a time division, realize the function of an optical path switching element such as a flip mirror.

It should be noted that, in this specification, an optical element or an optical system that splits the incident light into two light and reversibly combines the two incident light may be referred to as a "splitter". Further, it should be noted that, in this specification, an optical element or an optical system that combines two incident light may be referred to as a "splitter".

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

An ophthalmic apparatus according to embodiments generates measurement light (illumination light) with a predetermined shape using light from a light source, and irradiates the measurement light onto a predetermined site on a subject's eye while moving an irradiated position (irradiated range) of the measurement light by deflecting the measurement light that has been guided to an optical scanner by a splitter (for example, FIG. 1).

Returning light of the measurement light from the subject's eye is detected using a detector via the splitter. The light receiving result(s) of the returning light is read out from light receiving element(s) at the light receiving position(s) of the returning light corresponding to the irradiated position(s) of the measurement light, in synchronization with the movement timing of the irradiated position(s) of the measurement light. An SLO image (front image) of the predetermined site of the subject's eye can be acquired using the light receiving results of the returning light of the measurement light obtained by the detector.

Further, the splitter combines (interferes) the reference light obtained by splitting the measurement light with the returning light of the measurement light from the subject's eye to generate combined light (interference light). The detector receives the combined light generated by the splitter. The light receiving result(s) of the combined light is read out from light receiving element(s) at the light receiving position(s) of the returning light corresponding to the irradiated position(s) of the measurement light, in synchronization with the movement timing of the irradiated position(s) of the measurement light. An OCT image (tomographic image) of the predetermined site of the subject's eye can be acquired using the light receiving results of the combined light obtained by the detector.

This allows to acquire SLO signals (or SLO images) and OCT signals (or OCT images) of the predetermined site of the subject's eye, while sharing the light source, the optical scanner, and the detector. In particular, by sharing the light source and the optical scanner, the SLO signals and the OCT signals, or the SLO image and the OCT image can be aligned with high accuracy.

In some embodiments, the measurement light and the reference light are generated by splitting the light from the light source. In some embodiments, the measurement light and the reference light are generated by switching the optical path of the light from the light source.

In some embodiments, by performing light-shielding control on the reference light, the light receiving result of the returning light and the light receiving result of the combined light are acquired using a single detector. This allows to greatly simplify the configuration of the ophthalmic apparatus.

In some embodiments, the returning light is split into first returning light and second returning light, and the detector includes a first detector that detects the first returning light and a second detector that detects the combined light between the second returning light and the reference light. This allows to simultaneously acquire the SLO signals and the OCT signals (or the SLO images and the OCT images).

In some embodiments, the predetermined site is an anterior segment or a posterior segment. Examples of the anterior segment include a cornea, an iris, a crystalline lens, a ciliary body, and a ciliary zonule. Examples of the posterior segment include a vitreous body, and a fundus or the vicinity of the fundus (retina, choroid, sclera, etc.).

The configuration of the ophthalmic apparatus according to the embodiments is not limited to the above configuration. For example, the ophthalmic apparatus according to the embodiments deflects measurement light with a predetermined shape, and irradiates the measurement light onto a predetermined site on the subject's eye, while moving an irradiated position (irradiated range) of the measurement light that has been guided to the subject's eye via the splitter (for example, FIG. 22).

Returning light of the measurement light from the subject's eye is detected using a detector. The light receiving result(s) of the returning light is read out from light receiving element(s) at the light receiving position(s) of the returning light corresponding to the irradiated position(s) of the measurement light, in synchronization with the movement timing of the irradiated position(s) of the measurement light. An SLO image (front image) of a predetermined site of the subject's eye can be acquired using the light receiving results of the returning light of the measurement light obtained by the detector.

The splitter combines (interferes) the reference light obtained by splitting the measurement light with the returning light of the measurement light from the subject's eye to generate combined light (interference light). The detector receives the combined light generated by the splitter. The light receiving result(s) of the combined light is read out from light receiving element(s) at the light receiving position(s) of the returning light corresponding to the irradiated position(s) of the measurement light, in synchronization with the movement timing of the irradiated position(s) of the measurement light. An OCT image (tomographic image) of the predetermined site of the subject's eye can be acquired using the light receiving results of the combined light obtained by the detector.

A method of controlling the ophthalmic apparatus according to the embodiments includes one or more steps for realizing the processing executed by a processor (computer) in the ophthalmic apparatus according to the embodiments. A program according to the embodiments causes the processor to execute each step of the method of controlling the ophthalmic apparatus according to the embodiments.

Hereinafter, a case where the ophthalmic apparatus according to the embodiments acquires images of the fundus of the subject's eye mainly will be described. Hereafter, the measurement light according to the embodiments will be referred to as "illumination light".

First Embodiment

Figure 2:
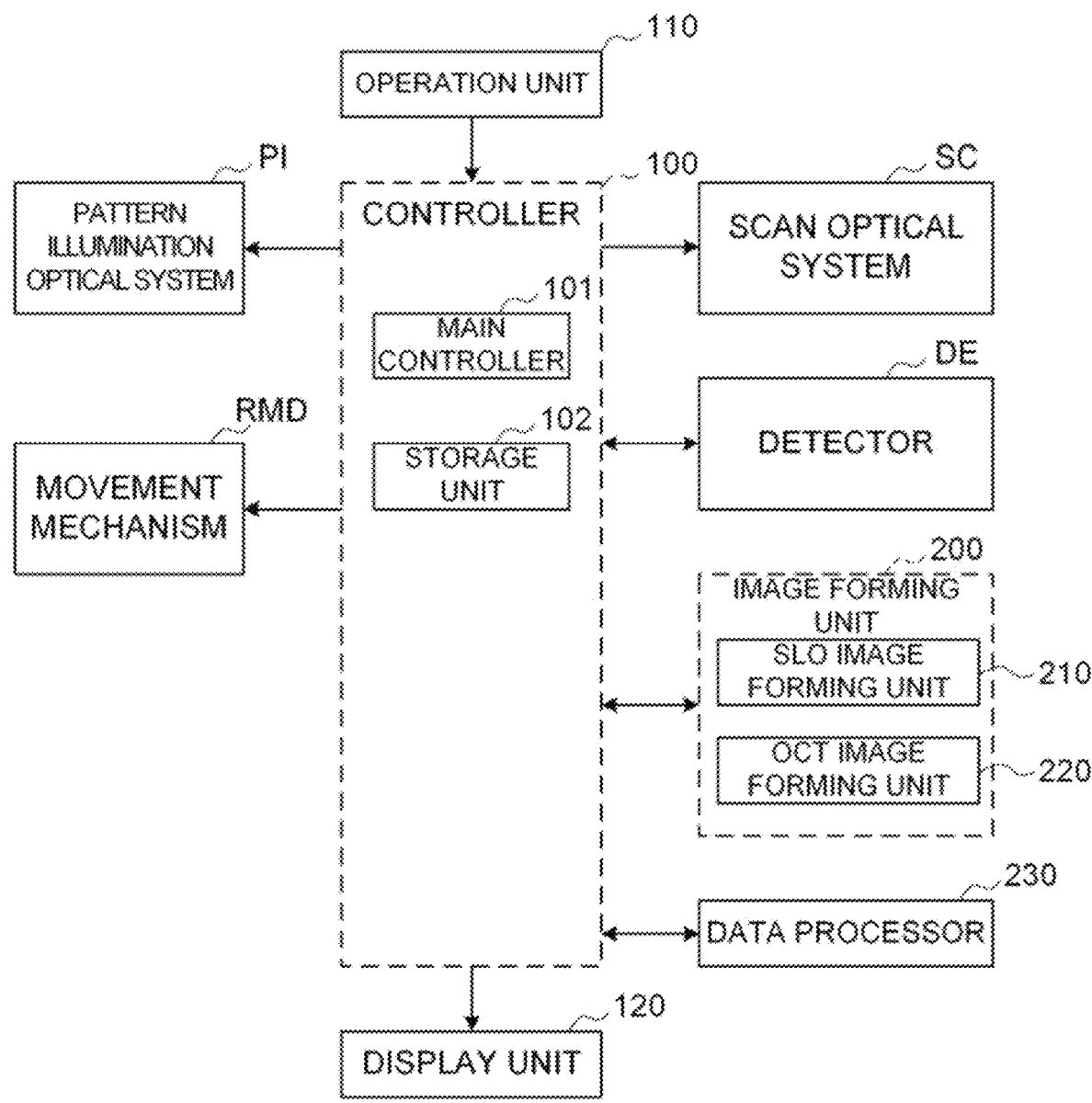
FIG. 2 is a schematic diagram illustrating an example of a configuration of a control system of the ophthalmic apparatus according to the first embodiment.

FIGS. 1 and 2 show block diagrams of examples of the configuration of the ophthalmic apparatus according to a first embodiment. FIG. 1 represents the schematic block diagram illustrating the configuration of an optical system of the ophthalmic apparatus according to the first embodiment. FIG. 2 shows a schematic block diagram illustrating the configuration of a control system (processing system) of the ophthalmic apparatus according to the first embodiment. In FIG. 2, like reference numerals designate like parts as in FIG. 1. The same description may not be repeated.

The ophthalmic apparatus 1 according to the first embodiment includes a pattern illumination optical system PI, a splitter SP, a mirror RM, a scan optical system SC, an objective lens OBJ, a detector DE, and a timing controller TC.

The pattern illumination optical system PI generates illumination light (illumination pattern, measurement light) with a predetermined shape. The pattern illumination optical system PI includes a light source and a slit with a aperture having a predetermined shape formed, and outputs the illumination light with the predetermined shape by illuminating the slit with light from the light source. The pattern illumination optical system PI generates the illumination light in the visible region or infrared (near-infrared) region.

In some embodiments, the pattern illumination optical system PI includes a projector with a light source, and the projector outputs the illumination light with a predetermined shape. Examples of the projector include an LCD (Liquid Crystal Display) type projector using a transmissive LCD panel, an LCOS (Liquid Crystal On Silicon) type projector using a reflective LCD panel, a DLP (Digital Light Processing) (registered trademark) type projector using a DMD (Digital Mirror Device).

Further, the pattern illumination optical system PI generates the illumination light and reference light (split light)

using light from the light source. In some embodiments, the pattern illumination optical system PI generates the illumination light and the reference light by splitting the light from the light source. In some embodiments, the pattern illumination optical system PI generates the reference light by splitting the illumination light. In some embodiments, the pattern illumination optical system PI outputs the illumination light and the reference light by switching the optical path of the light from the light source.

The splitter SP guides the illumination light generated by the pattern illumination optical system PI into an illumination optical path (measurement optical path), and guides the reference light into a reference optical path. The scan optical system SC and the objective lens OBJ are arranged in the illumination optical path. The mirror RM is arranged in the reference optical path.

The illumination light that has been guided to the illumination optical path is deflected by the scan optical system SC. The scan optical system SC includes a one-axis optical scanner or a two-axis optical scanner. For example, when the shape of the luminous flux cross section of the illumination light generated by the pattern illumination optical system PI is a shape extending in a one-dimensional direction, the scan optical system SC includes the one-axis optical scanner or the two-axis optical scanner to two-dimensionally deflect the illumination light. For example, when the shape of the luminous flux cross section of the illumination light generated by the pattern illumination optical system PI is a shape extending in a two-dimensional direction, the scan optical system SC includes the one-axis optical scanner to one-dimensionally deflect the illumination light.

The illumination light deflected by the scan optical system SC is refracted by the objective lens OBJ, enters into the eye through the pupil of the subject's eye E, and is irradiated onto the fundus Ef of the subject's eye E. The returning light of the illumination light irradiated onto the fundus Ef passes through the objective lens OBJ and the scan optical system SC, and enters the splitter SP.

The reference light that has been guided to the reference optical path is reflected by the mirror RM, and returns to the splitter SP. The mirror RM can be moved along the optical path of the reference light. By moving the mirror RM along the optical path of the reference light, the optical path length of the reference light can be changed. In some embodiments, the optical path length of the illumination light is configured to be changeable instead of the optical path length of the reference light. In some embodiments, the optical path length of the reference light and the optical path length of the illumination light are configured to be changeable.

The splitter SP generates the interference light (combined light) between the returning light of the illumination light from the subject's eye E passing through the illumination optical path and the reference light passing through the reference optical path. That is, the splitter SP guides the illumination light from the pattern illumination optical system PI to the scan optical system SC, and generates the interference light between the reference light and the returning light of the illumination light from the subject's eye E.

The detector DE includes a CMOS image sensor, CCD (Charge Coupled Device) image sensor, or a time delayed integration (TDI) sensor. The detector DE detects the returning light of the illumination light from the subject's eye E passing through the illumination optical path and the interference light generated by the splitter SP, via the splitter SP. The detector DE can output the light-receiving result using the rolling shutter method, the global shutter method, or the TDI method under the control from the timing controller TC.

The timing controller TC controls the pattern illumination optical system PI, the scan optical system SC, and the detector DE. The timing controller TC acquires the light reception results of the returning light or the combined light from the light receiving elements of the detector DE at the light receiving positions of the returning light corresponding to the irradiated positions, in synchronization with the movement timing of the irradiated positions of the illumination light, while moving the irradiated positions of the illumination light on the subject's eye E by controlling the optical scan optical system SC. The functions of the timing controller TC are realized by one or more processors.

As shown in FIG. 2, the control system of the ophthalmic apparatus 1 is configured with a controller 100 as a center. It should be noted at least a part of the configuration of the control system may be included in the ophthalmic apparatus 1.

The controller 100 controls each part of the ophthalmic apparatus 1. The controller 100 includes a main controller 101 and a storage unit 102. The main controller 101 includes a processor and executes the control processing of each part of the ophthalmic apparatus 1 by executing processing according to the program(s) stored in the storage unit 102. For example, the controller 100 realizes the functions of the timing controller TC shown in FIG. 1.

The main controller 101 controls each of the pattern illumination optical system PI, a movement mechanism RMD, the scan optical system SC, the detector DE, an image forming unit 200, and the data processor 230.

Examples of the control for the pattern illumination optical system PI include switching the light source on and off, switching the wavelength range of the emitted light of the light source, changing the light amount of the light source, and controlling the shape of the luminous flux cross section of the illumination light.

The movement mechanism RMD moves the mirror RM along the optical path of the reference light using a known mechanism.

Examples of the control for the scan optical system SC include control of at least one of a deflection start angle, a deflection end angle, a deflection angle range, a deflection speed, and a deflection frequency of the illumination light.

Examples of the control for the detector DE include the rolling shutter control, the global shutter control, and the TDI control.

The image forming unit 200 forms an image of the subject's eye E based on detection result of the returning light or the interference light obtained by the detector DE. Examples of the image of the subject's eye E include a front image and a tomographic image.

The image forming unit 200 includes an SLO image forming unit 210 and an OCT image forming unit 220. The SLO image forming unit 210 forms the SLO image (front image) of the subject's eye E based on detection result of the returning light obtained by the detector DE. For example, the SLO image forming unit 210 forms the SLO image based on the detection result of the returning light and the pixel position signal. The pixel position signal is generated from irradiated position information of the illumination light on the fundus Ef and position information of the light receiving element that has received the returning light in the detector DE, for example. The irradiated position information can be specified from deflection control information of the scan optical system SC, for example.

The OCT image forming unit 220 forms the OCT image (tomographic image) of the subject's eye E based on detection result of the interference light obtained by the detector DE. For example, the OCT image forming unit 220 applies Fourier transform and the like to the spectral distribution based on the detection result of the interference light, for each incident position of the illumination light on the subject's eye E to form the reflection intensity profile in each A-line. The OCT image forming unit 220 forms the OCT image by imaging the reflection intensity profile in each A-line.

The data processor 230 executes various kind of data processing. Examples of the data processing include data processing on the image formed by the image forming unit 200. Examples of this processing include image processing, image analyzing, image evaluation, diagnosis support, and the like.

Further, the data processor 230 can synthesis two or more SLO images formed by the image forming unit 200 to form an SLO synthesis image. Examples of the SLO synthetic image include a panoramic image and a color SLO image. In the same way, the data processor 230 can form a two-dimensional OCT image or a three-dimensional OCT image from two or more one-dimensional OCT images formed by the image forming unit 200.

The operation unit 110 includes an operation device. The operation device includes various hardware keys and/or various software keys. Upon receiving the operation content for the operation device, the controller 100 outputs a control signal corresponding to the operation content to each part of the ophthalmic apparatus 1.

The display unit 120 includes a display device. The display device includes a liquid crystal display. At least a part of the display device and at least a part of the operation device may be configured integrally. One example of this is the touch panel display.

The illumination light is an example of the "measurement light" according to the embodiments. The pattern illumination optical system PI is an example of the "irradiation optical system" according to the embodiments. The splitter SP is an example of the "optical splitting and combining unit" according to the embodiments. The scan optical system SC is an example of the "optical scanner" according to the embodiments. The SLO image forming unit 210 is an example of the "first image forming unit" according to the embodiments. The OCT image forming unit 220 is an example of the "second image forming unit" according to the embodiments.

Figure 3:
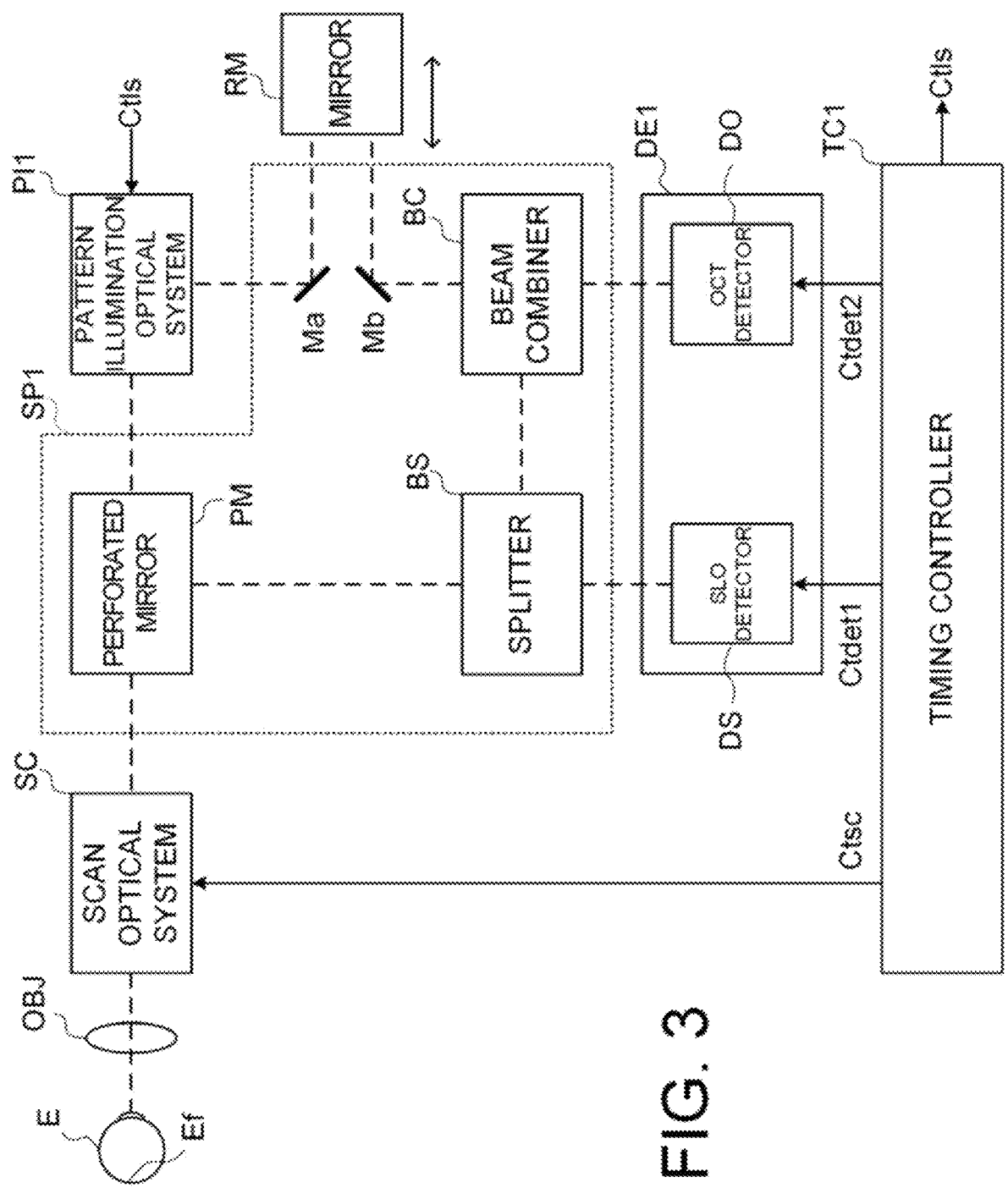
FIG. 3 is a schematic diagram illustrating an example of a configuration of an optical system of the ophthalmic apparatus according to the first embodiment.

FIG. 3 shows a block diagram of an example of the configuration of the ophthalmic apparatus 1 in FIG. 1. In FIG. 3, like reference numerals designate like parts as in FIG. 1, and the redundant explanation may be omitted as appropriate. The pattern illumination optical system PI1 is an example of the irradiation optical system PI in FIG. 1. The splitter SP1 is an example of the splitter SP in FIG. 1. The detector DE1 is an example of the detector DE in FIG. 1. The timing controller TC1 is an example of the timing controller TC.

The splitter SP1 includes a perforated mirror PM, a splitter BS, a beam combiner BC, and mirrors Ma and Mb.

In the perforated mirror PM, a hole is formed. The illumination light or the returning light of the illumination light passes through this hole. The perforated mirror PM separates the optical path of the returning light of the illumination light from the subject's eye E from the optical path of the illumination light generated by the pattern illumination optical system PI1. The hole formed in the perforated mirror PM is arranged at a position conjugate optically to an iris of the subject's eye E. As a result, the light irradiated onto the subject's eye E and the returning light from the subject's eye E are pupil-divided.

In some embodiments, the illumination light from the pattern illumination optical system PI1 passes through the hole formed in the perforated mirror PM, and the returning light of the illumination light is reflected on the peripheral region of the hole to be guided to the splitter BS.

In some embodiments, the illumination light from the pattern illumination optical system PI1 is reflected on the peripheral region of the hole, is guided to the scan optical system SC, and the returning light of the illumination light passes through the hole to be guided to the splitter BS.

The splitter BS splits the returning light of the illumination light from the perforated mirror PM into first returning light and second returning light. The function of the splitter BS is realized by an optical path switching element such as a beam splitter, a dichroic beam splitter, or a flip mirror.

The first returning light split by the splitter BS is received by the detector DE1 (SLO detector DS). The SLO detector DS in the detector DE1 may be a detector used in the known SLO (Scanning Laser Ophthalmoscope). The second returning light split by the splitter BS is guided to the beam combiner BC.

In contrast, the reference light generated by the pattern illumination optical system PI1 also enters the splitter SP1. The reference light entering the splitter SP1 is reflected by the mirror Ma and is guided to the mirror RM. The mirror RM reflects the incident light in a direction opposite to the traveling direction of the incident light. The reference light reflected by the mirror RM is reflected by the mirror Mb to be guided to the beam combiner BC.

The beam combiner BC generates the interference light between the second returning light split by the splitter BS and the reference light reflected by the mirror Mb. The interference light generated by the beam combiner BC is received by the detector DE1 (OCT detector DO). The OCT detector DO in the detector DE1 may be a detector used in the known OCT (Optical Coherence Tomography). In some embodiments, the function of the beam combiner BC is realized by a fiber coupler. In some embodiments, the function of the beam combiner BC is realized by a first mirror that deflects the second returning light toward the light receiving surface of the OCT detector DO and a second mirror that deflects the reference light toward this light receiving surface.

The timing controller TC1 outputs the control signal Ctsc to the scan optical system SC, outputs the control signal Ctdet1 to the SLO detector DS, outputs the control signal Ctdet2 to the OCT detector DO, and outputs the control signal Ctls to the pattern illumination optical system PI1. As a result, the light receiving results are read out from the light receiving elements at the light receiving positions of the second returning light and the interference light corresponding to the irradiated positions of the illumination light, in synchronization with the movement timing of the irradiated positions of the illumination light on the subject's eye E.

The perforated mirror PM is an example of the "optical splitter" according to the embodiments. The splitter BS is an example of the "first splitter" according to the embodiments. The SLO detector DS is an example of the "first detector" according to the embodiments. The OCT detector DO is an example of the "second detector" according to the embodiments. The mirrors Ma and Mb, and the mirror RM are an example of the "second optical path length changing unit" according to the embodiments.

Figure 4:
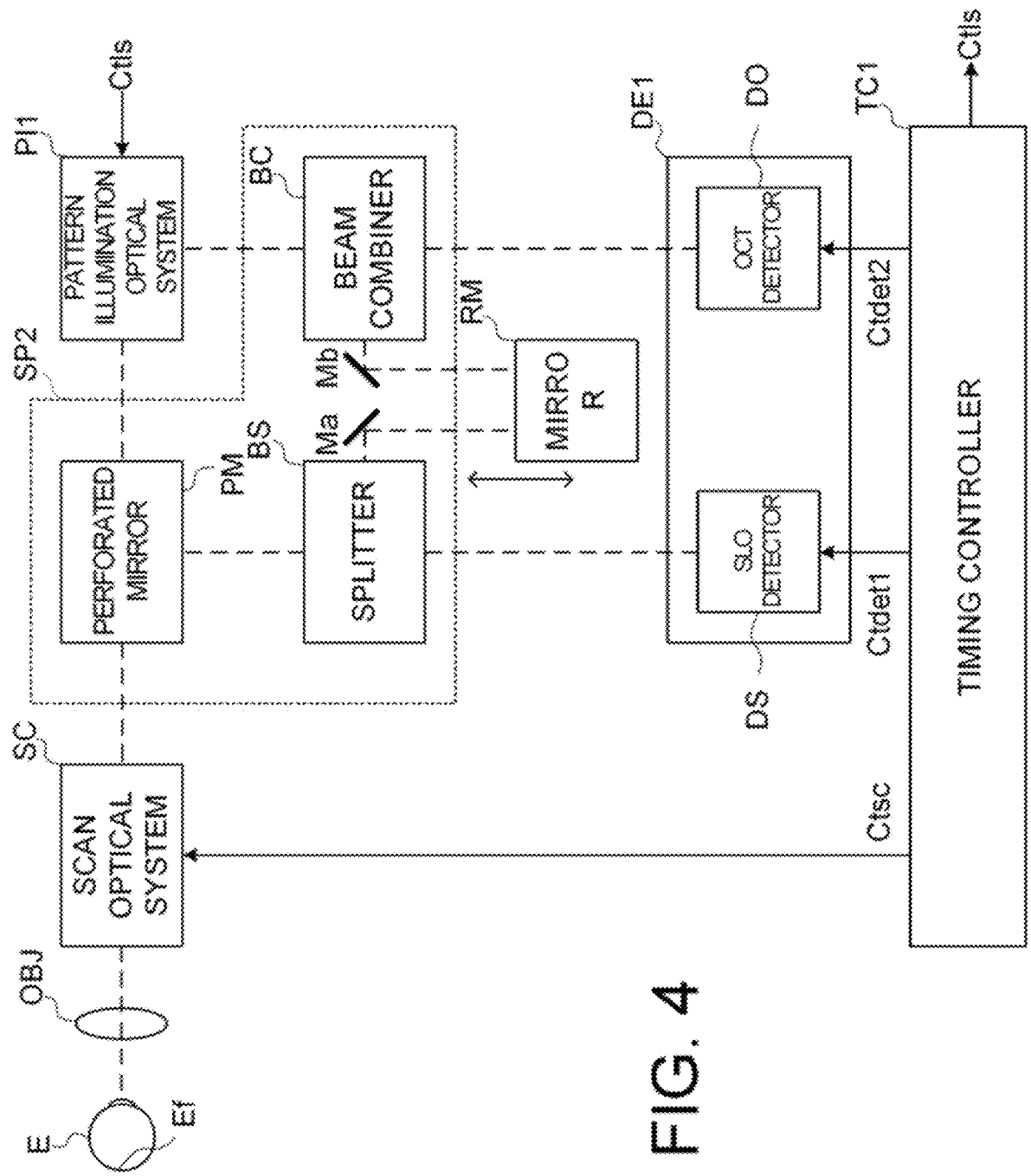
FIG. 4 is a schematic diagram illustrating an example of the configuration of the optical system of the ophthalmic apparatus according to the first embodiment.

FIG. 4 shows a block diagram of an another example of the configuration the ophthalmic apparatus 1 in FIG. 1. In FIG. 4, like reference numerals designate like parts as in FIG. 3. The same description may not be repeated. The splitter SP2 is an example of the splitter SP in FIG. 1.

The configuration of the ophthalmic apparatus 1 in FIG. 4 differs from the configuration of the ophthalmic apparatus 1 in FIG. 3 in the positions of the mirrors RM, Ma, and Mb. That is, in FIG. 3, the mirrors Ma and Mb are placed so that the mirror RM is placed in the reference optical path between the pattern illumination optical system PI1 and the beam combiner BC. In contrast, in FIG. 4, the mirrors Ma and Mb are placed so that the mirror RM is placed in the illumination optical path (measurement optical path) between the splitter BS and the beam combiner BC.

That is, in FIG. 4, the first returning light split by the splitter BS is guided to the detector DE1 (SLO detector DS), and the second returning light split by the splitter BS is guided to the mirror Ma. The second returning light is reflected by the mirror Ma, and then is guided to the mirror RM. The second returning light reflected by the mirror RM is reflected by the mirror Mb, and then is guided to the beam combiner BC.

The beam combiner BC generates the interference light between the reference light from the pattern illumination optical system PI1 and the second returning light reflected by the mirror Mb. The interference light generated by the beam combiner BC is guided to the detector DE1 (OCT detector DO).

In FIG. 4, the mirrors Ma and Mb, and the mirror RM are an example of the "first optical path length changing unit" according to the embodiments.

In the ophthalmic apparatus 1 according to the first embodiment, the illumination light is generated using a wavelength swept light source. In the following, a case where the mirror RM is arranged as shown in FIG. 3 in the ophthalmic apparatus 1 will be described. However, the mirror RM is arranged as shown in FIG. 4, in the ophthalmic apparatus 1.

Figure 5:
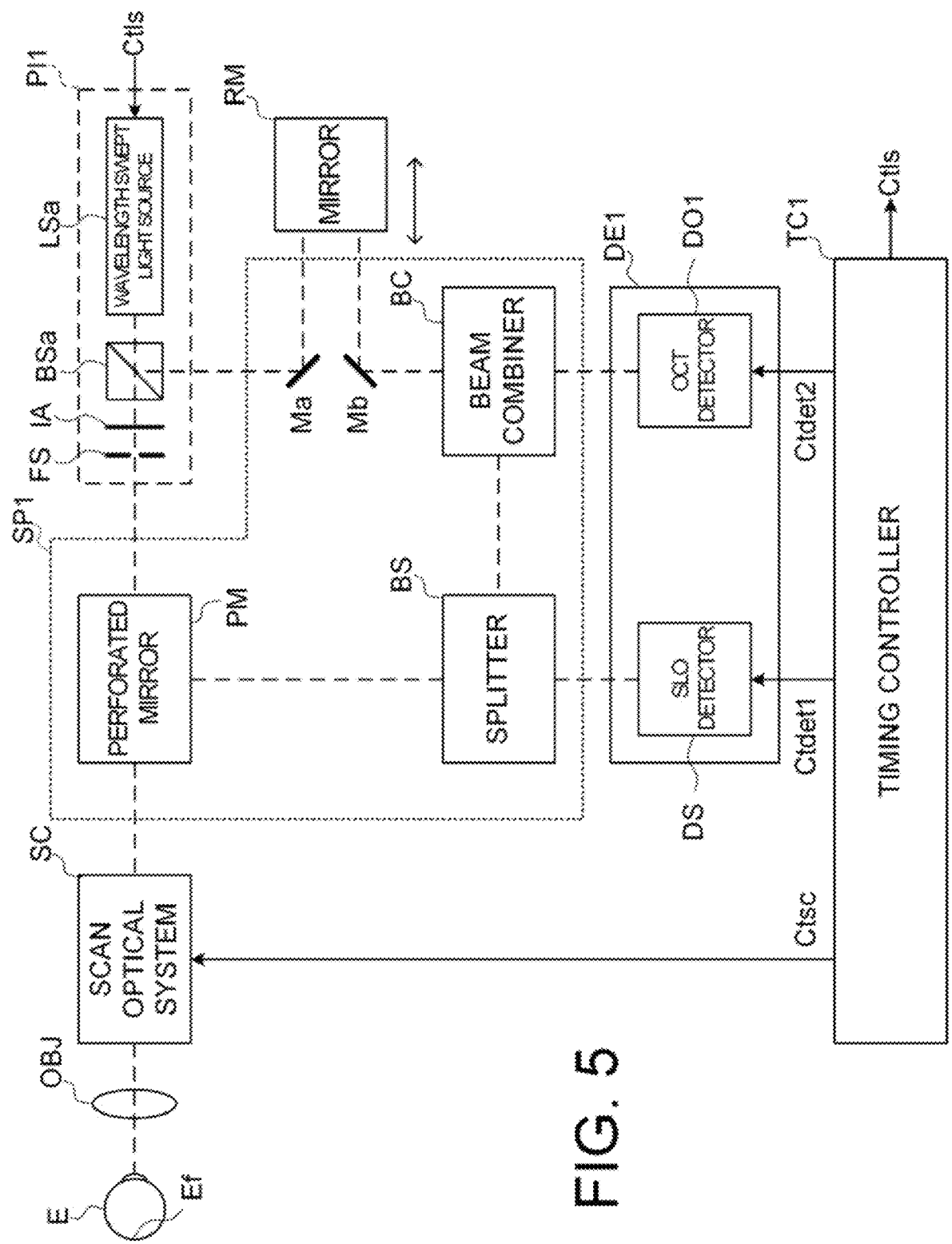
FIG. 5 is a schematic diagram illustrating an example of the configuration of the optical system of the ophthalmic apparatus according to the first embodiment.

FIG. 5 shows a block diagram of an example of the configuration of the ophthalmic apparatus 1 in FIG. 3. In FIG. 5, like reference numerals designate like parts as in FIG. 3. The same description may not be repeated.

The pattern illumination optical system PI1 includes a wavelength swept light source LSa, a beam splitter BSa, an iris aperture IA, and a slit FS.

The wavelength swept light source LSa temporally changes the wavelength of the emitted light within a predetermined wavelength range. The wavelength swept light source LSa may be a known wavelength swept light source used in the Swept Source OCT.

The beam splitter BSa splits light from the wavelength swept light source LSa into the illumination light and the reference light. The illumination light split by the beam splitter BSa is guided to the iris aperture IA. The reference light split by the beam splitter BSa is guided to the mirror Ma in the splitter SP1. In some embodiments, the function of the beam splitter BSa is realized by temporally splitting the light from the wavelength swept light source LSa into the illumination light and the reference light using an optical path switching element such as a flip mirror.

The iris aperture IA is arranged at a position substantially conjugate optically to the iris of the subject's eye E. In the iris aperture IA, an aperture is formed at a position away from the optical axis, for example. The illumination light passing through the aperture formed in the iris aperture IA is guided to the slit FS.

The slit FS is arranged at a position substantially conjugate optically to a measurement site in the subject's eye E. In the slit FS, an aperture that defines an irradiated shape on the measurement site of the subject's eye E is formed. The illumination light passing through the aperture formed in the slit FS is guided to the perforated mirror PM in the splitter SP1.

It should be noted that the OCT detector DO1 used in the swept source type OCT is used as the OCT detector DO, in the detector DE1.

Hereinafter, a specific configuration example of the ophthalmic apparatus 1 according to the first embodiment will be described.

[Configuration of Optical System]

Figure 6:
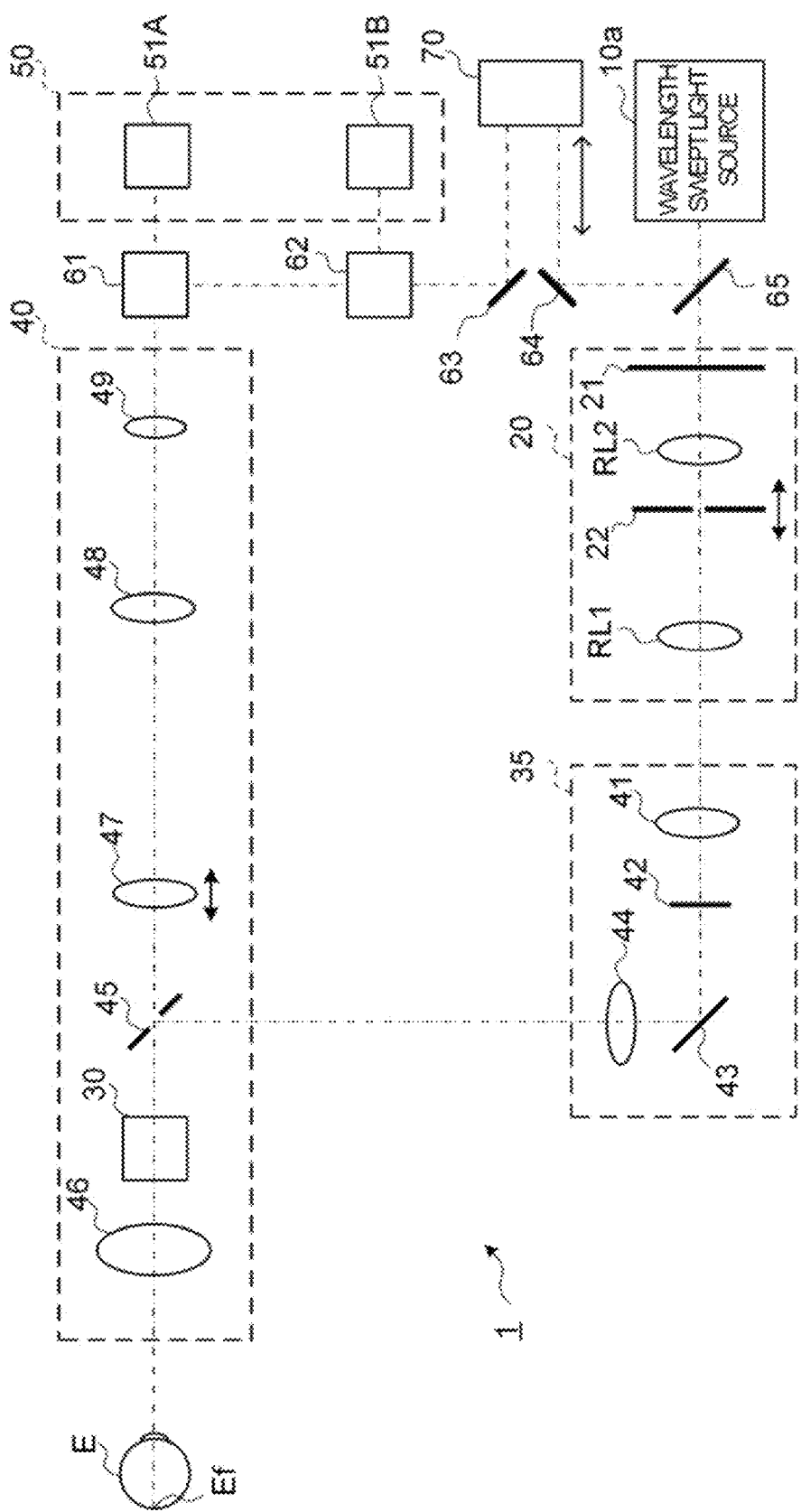
FIG. 6 is a diagram illustrating an example of the configuration of the optical system of the ophthalmic apparatus according to the first embodiment.
Figure 7:
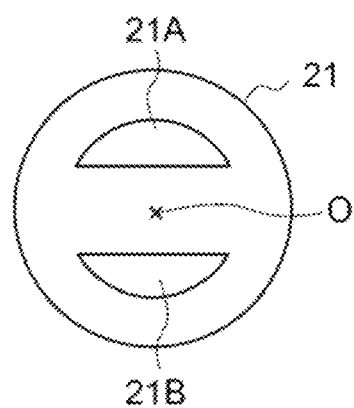
FIG. 7 is an explanatory diagram of an example of the configuration of the optical system of the ophthalmic apparatus according to the first embodiment.
Figure 8:
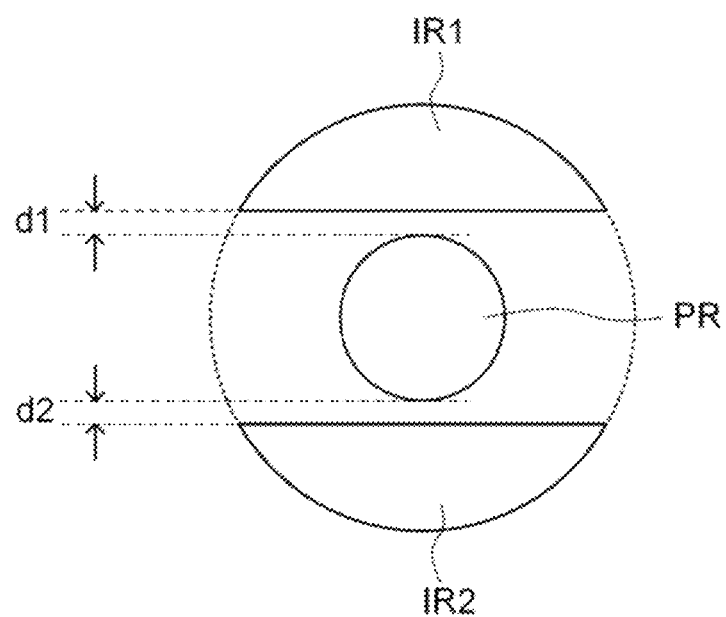
FIG. 8 is an explanatory diagram of an example of the configuration of the optical system of the ophthalmic apparatus according to the first embodiment.
Figure 9:
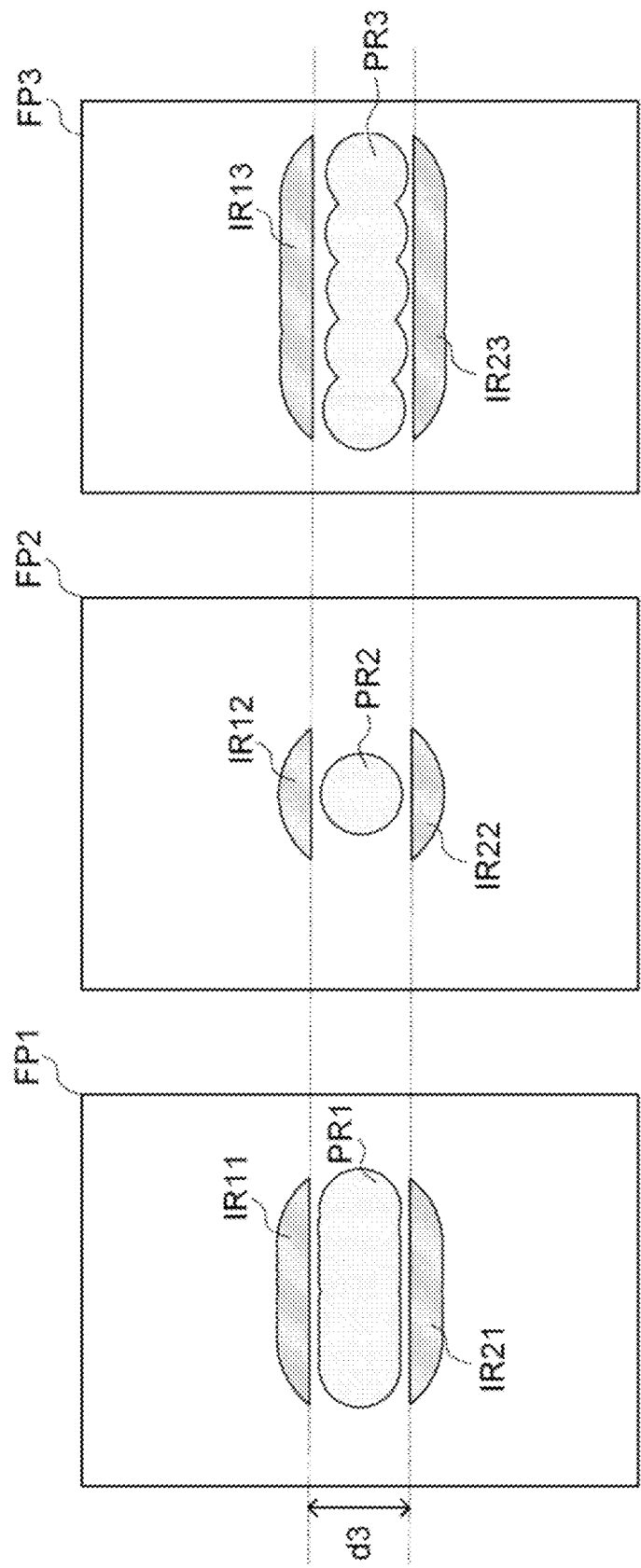
FIG. 9 is an explanatory diagram of an operation of the ophthalmic apparatus according to the first embodiment.
Figure 10:
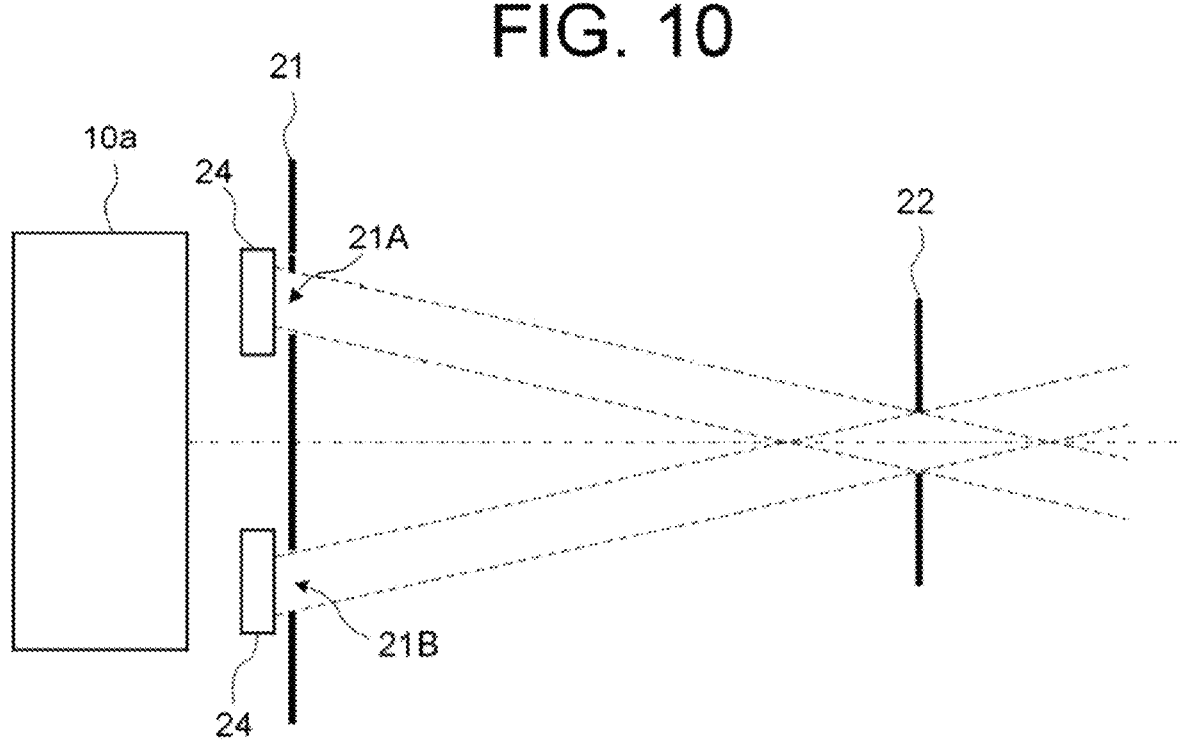
FIG. 10 is an explanatory diagram of an operation of the ophthalmic apparatus according to the first embodiment.
Figure 11:
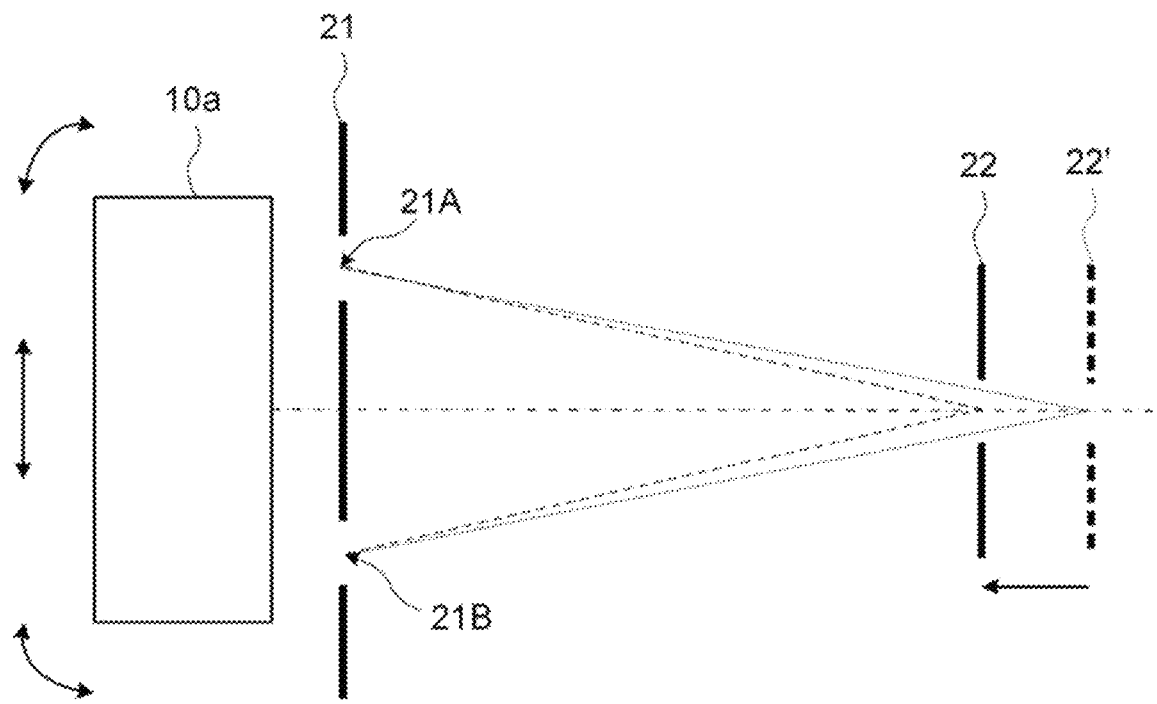
FIG. 11 is an explanatory diagram of an operation of the ophthalmic apparatus according to the first embodiment.
Figure 12:
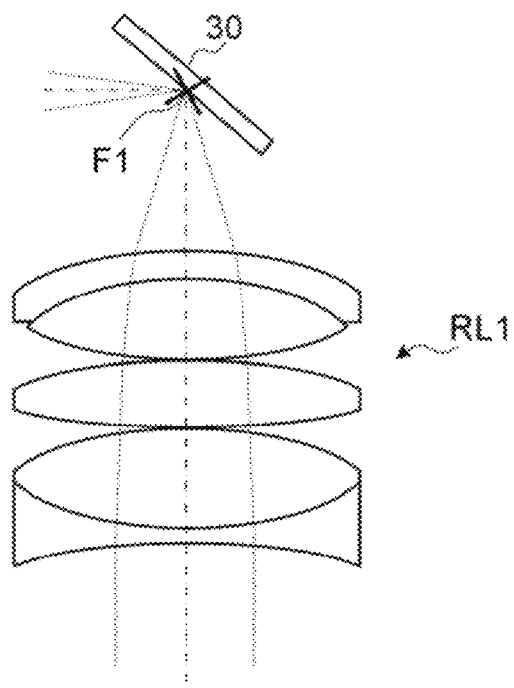
FIG. 12 is an explanatory diagram of an example of the configuration of the optical system of the ophthalmic apparatus according to the first embodiment.
Figure 13:
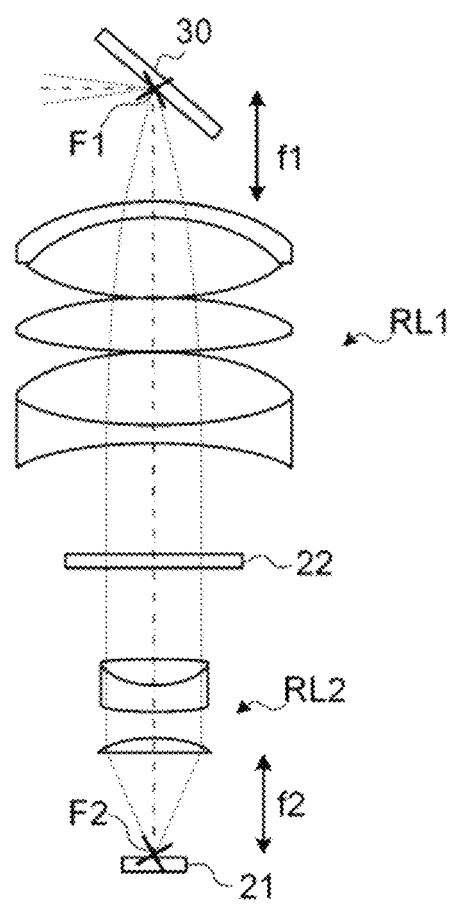
FIG. 13 is an explanatory diagram of an example of the configuration of the optical system of the ophthalmic apparatus according to the first embodiment.

FIGS. 6 to 13 show examples of the configuration of the ophthalmic apparatus according to the first embodiment. FIG. 6 represents an example of the configuration of an optical system of the ophthalmic apparatus 1 according to the first embodiment. FIG. 7 schematically represents an example of the configuration of the iris aperture 21 in FIG. 6 when viewed from a direction of an optical axis O. FIG. 8 schematically represents a shape of luminous flux cross section of the illumination light. FIG. 9 represents a diagram describing the iris aperture 21 in FIG. 6. FIG. 10 represents an example of the configuration of the iris aperture 21 in FIG. 6 and the slit 22 in FIG. 6 when viewed from the side or top. FIG. 11 represents a diagram for explaining the wavelength swept light source 10a. In FIG. 6. FIG. 12 represents an example of the configuration of a relay lens system RL1 in FIG. 6. FIG. 13 represents an example of the configuration of a relay lens system RL2 in FIG. 6. In FIGS. 12 and 13, a case where the relay lens system RL1 includes three lenses is shown, however the number of lenses that make up the relay lens system RL1 is not limited. Further, in FIG. 13, a case where the relay lens system RL2 includes two lenses is shown, however the number of lenses that make up the relay lens system RL2 is not limited. In FIGS. 6 to 13, like parts are designated by like reference numerals as in repetitious description of such parts may not be provided.

The ophthalmic apparatus 1 includes the wavelength swept light source 10a, an illumination optical system 20, the optical scanner 30, a projection optical system 35, and an imaging optical system 40, and imaging device 50. In FIG. 6, the imaging optical system 40 includes the optical scanner 30. In some embodiments, the optical scanner 30 (and an objective lens 46) is (are) provided outside the imaging optical system 40. In some embodiments, the illumination optical system 20 includes at least one of the wavelength swept light source 10a and the projection optical system 35. In some embodiments, the imaging optical system 40 includes the imaging device 50.

(Wavelength Swept Light Source 10a)

The wavelength swept light source 10a includes a laser light source including a resonator, and temporally changes the wavelength of the emitted light within a predetermined wavelength range. For example, the wavelength swept light source 10a includes s a near-infrared tunable laser that changes a center wavelength within the wavelength range of 1000 nm to 1100 nm at high speed, for example.

Light from the wavelength swept light source 10a is split into the illumination light and the reference light by the beam splitter 65. The illumination light split by the beam splitter 65 is guided to the illumination optical system 20. The reference light split by the beam splitter 65 is guided to the mirror 64. It should be noted that the beam splitter 65 may be arranged at an arbitrary position between the illumination optical system 20 and the perforated mirror 45.

In some embodiments, a flip mirror is placed in place of the beam splitter 65. The flip mirror alternately switches the optical path of the light from the wavelength swept light source 10a at each predetermined switching timing to guide the light from the wavelength swept light source 10a to the illumination optical system 20 as the illumination light or to the mirror 64 as the reference light.

(Illumination Optical System 20)

The illumination optical system 20 generates slit-shaped illumination light using the light from the illumination light split by the beam splitter 65. The illumination optical system 20 guides the generated illumination light to the projection optical system 35.

The illumination optical system 20 includes the iris aperture 21, the slit 22, and the relay lens systems RL1 and RL2. The relay lens system RL1 is arranged between the relay lens 41 in the projection optical system 35 and the slit 22. The relay lens system RL2 is arranged between the iris aperture 21 and the slit 22.

The iris aperture 21 (specifically, aperture(s) described below) can be arranged at a position substantially conjugate optically to the iris (pupil) of the subject's eye E. In the iris aperture 21, one or more apertures are formed at positions away from the optical axis O.

The relay lens system RL2 includes one or more lenses, and guides the illumination light passing through the aperture(s) formed in the iris aperture 21 to the slit 22.

The slit 22 (specifically, aperture(s) described below) can be arranged at a position substantially conjugate optically to the fundus Ef of the subject's eye E. For example, in the slit 22, the aperture is formed in a direction corresponding to a line direction (row direction) that is read out from the image sensor 51A or the image sensor 51B described below using the rolling shutter method.

The relay lens system RL1 includes one or more lenses, and guides the illumination light passing through the aperture(s) formed in the slit 22 to the projection optical system 35.

As described above, in the illumination optical system 20, the illumination light transmitted through the beam splitter 65 passes through the aperture(s) formed in the iris aperture 21, is transmitted through the relay lens system RL2, passed through the aperture(s) formed in the slit 22, and is transmitted through the relay lens system RL1. The light transmitted through the relay lens system RL1 is guided to the projection optical system 35.

(Projection Optical System 35)

The projection optical system 35 guides the illumination light formed in a slit shape to the fundus Ef of the subject's eye E. In the embodiments, the projection optical system 35 guides the illumination light to the fundus Ef through an optical path that is coupled with the optical path of the imaging optical system 40 by the perforated mirror 45 as the optical path coupling member described below.

The projection optical system 35 includes the relay lens 41, a black point plate 42, a reflective mirror 43, and a relay lens 44. Each of the relay lenses 41 and 44 includes one or more lenses.

(Black Point Plate 42)

The black point plate 42 is arranged at a position substantially conjugate optically to a lens surface of the objective lens 46 or the vicinity of the lens surface of the objective lens 46. This prevents the reflected light from the lens surface of the objective lens 46 from being guided to the wavelength swept light source 10a.

In the projection optical system 35 with this configuration, the illumination light formed in a slit shape is transmitted through the relay lens 41, passes through the black point plate 42, is reflected by the reflective mirror 43, is transmitted through the relay lens 44 to be guided to the perforated mirror 45.

(Imaging Optical System 40)

The imaging optical system 40 guides the illumination light that has been guided through the projection optical system 35 to the fundus Ef of the subject's eye E, and also guides the returning light of the illumination light from the fundus Ef to the imaging device 50.

In the imaging optical system 40, an optical path of the illumination light from the projection optical system 35 and an optical path of the returning light of the illumination light from the fundus Ef are coupled. By using the perforated mirror 45 as an optical path coupling member to couple these optical paths, it enables pupil division between the illumination light and the returning light of the illumination light.

The imaging optical system 40 includes the perforated mirror 45, the objective lens 46, a focusing lens 47, a relay lens 48, and an imaging lens 49. The relay lens 48 includes one or more lenses. In the embodiments, the imaging optical system 40 includes the optical scanner 30 placed between the perforated mirror 45 and the objective lens 46.

In the perforated mirror 45, the hole is formed. The hole is arranged on the optical axis of the imaging optical system 40. The hole in the perforated mirror 45 is arranged at a position substantially conjugate optically to the iris of the subject's eye E. The perforated mirror 45 reflects the illumination light from the projection optical system 35 toward the objective lens 46, on the peripheral region of the hole. The perforated mirror 45 like this functions as a photographic stop.

That is, the perforated mirror 45 is configured to combine the optical path of the illumination optical system 20 (projection optical system 35) and the optical path of the imaging optical system 40 arranged in a direction of the optical axis passing through the hole, and also to guide the illumination light reflected on the peripheral region of the hole to the fundus Ef.

The optical scanner 30 is disposed at a position substantially conjugate optically to the iris of the subject's eye E. The optical scanner 30 deflects the slit-shaped illumination light reflected by the perforated mirror 45 (slit-shaped light passing through the aperture(s) formed in the slit 22). Specifically, the optical scanner 30 deflects the slit-shaped illumination light for sequentially illuminating a predetermined irradiated region of the fundus Ef to guide the illumination light to the objective lens 46, while changing the deflection angle within a predetermined deflection angle range with the iris or the vicinity of the iris of the subject's eye E as a scan center position. The optical scanner 30 can deflect the illuminating light one-dimensionally or two-dimensionally.

In case that the optical scanner 30 deflects the illumination light one-dimensionally, the optical scanner 30 includes a galvano scanner that deflects the illuminating light within a predetermined deflection angle range with reference to a predetermined deflection direction. In case that the optical scanner 30 deflects the illumination light two-dimensionally, the optical scanner 30 includes a first galvano scanner and a second galvano scanner. The first galvano scanner deflects the illumination light so as to move the irradiated position of the illumination light in a horizontal direction orthogonal to the optical axis of the imaging optical system 40 (illumination optical system 20). The second galvano scanner deflects the illuminating light deflected by the first galvano scanner so as to move the irradiated position of the illumination light in a vertical direction orthogonal to the optical axis of the imaging optical system 40 (illumination optical system 20). Examples of scan mode for moving the irradiated position of the illumination light using the optical scanner 30 include a horizontal scan, a vertical scan, a cross scan, a radial scan, a circle scan, a concentric scan, and a helical (spiral) scan.

The focusing lens 47 can be moved in an optical axis direction of the imaging optical system 40 using a movement mechanism (not shown). The movement mechanism moves the focusing lens 47 in the optical axis direction under the control from the controller 100 described below. This allows to image the returning light of the illumination light passing through the hole of the perforated mirror 45 on the light receiving surface of the image sensor 51A or the image sensor 51B in the imaging device 50.

In the imaging optical system 40 with this configuration, the illumination light from the projection optical system 35 is reflected on the peripheral region of the hole formed in the perforated mirror 45 toward the optical scanner 30. The illumination light reflected on the peripheral region of perforated mirror 45 is deflected by the optical scanner 30, is refracted by the objective lens 46, enters into the eye through the pupil of the subject's eye E, and illuminates the fundus Ef of the subject's eye E.

The returning light of the illumination light from the fundus Ef is refracted by the objective lens 46, passes through the optical scanner 30, passes through the hole of the perforated mirror 45, is transmitted through the focusing lens 47, is transmitted through the relay lens 48, is guided to the imaging device 50 through the imaging lens 49.

(Imaging Device 50)

The imaging device 50 includes image sensors 51A and 51B. The image sensor 51A includes a CMOS image sensor arranged one-dimensionally or two-dimensionally, for example. The image sensor 51B includes one or more balanced photodiodes, for example. Each of the image sensors 51A and 51B realizes the function as pixelated photodetectors. The light receiving surface (detecting surface, imaging surface) of each the image sensors 51A and 51B can be arranged at a position substantially conjugate optically to the fundus Ef as an imaging site.

The beam splitter 61 and the beam combiner 62 are arranged between the imaging optical system 40 and the imaging device 50. In some embodiments, the imaging device 50 includes at least one of the beam splitter 61 and the beam combiner 62. In some embodiments, the imaging optical system 40 includes at least one of the beam splitter 61 and the beam combiner 62.

The returning light of the illumination light from the subject's eye E transmitted through the imaging lens 49 is split by the beam splitter 61 into the first returning light and the second returning light. The first returning light is received by the image sensor 51A. The light receiving results obtained by the image sensor 51A are read out using the rolling shutter method, under the control from the controller 100 described below, for example. The second returning light is guided to the beam combiner 62.

In some embodiments, a flip mirror is placed in place of the beam splitter 61. The flip mirror switches the optical path of the returning light, and guides the returning light to the image sensor 51A as the first return light, or guides the returning light to the beam combiner 62 as the second returning light.

In contrast, the reference light (split light) split by the beam splitter 65 is guided to the retroreflector 70 by the mirror 64. The retroreflector 70 reflects the incident light in the direction parallel to and opposite to the incident direction. The retroreflector 70 can be moved along the incident direction of the incident light, under the control from the controller 100 described below. The reference light reflected by the retroreflector 70 is guided to the beam combiner 62 by the mirror 63.

The beam combiner 62 generates the interference light between the second returning light from the beam splitter 61 and the reference light from the mirror 63. The function of the beam combiner 62 is realized by a fiber coupler. In some embodiments, the beam combiner 62 is realized by a first mirror that deflects the second returning light and a second mirror that deflects the reference light. The interference light generated by the beam combiner 62 is received by the image sensor 51B. The light receiving results obtained by the image sensor 51B are read out using the rolling shutter method, under the control from the controller 100 described below, for example.

In FIG. 6, the wavelength swept light source 10a corresponds to the wavelength swept light source LSa. The wavelength swept light source 10a and illumination optical system 20 correspond to the pattern illumination optical system PI or pattern illumination optical system PI1. The beam splitter BSa corresponds to the beam splitter 65. The perforated mirror 45 corresponds to the perforated mirror PM. The beam splitter 61 corresponds to the splitter BS. The beam combiner 62 corresponds to the beam combiner BC. The mirrors 64 and 63, and the retroreflector 70 are mirrors Ma and Mb, and RM. The image sensor 51A corresponds to the SLO detector DS. Image sensor 51B corresponds to the OCT detector DO or the OCT detector DO1. The optical scanner 30 corresponds to the scan optical system SC.

(Iris Aperture 21)

Here, the iris aperture 21 will be described. In the iris aperture 21, the aperture that defines an incident position (incident shape) of the illumination light on the iris of the subject's eye E is formed.

For example, by forming the apertures in the iris aperture 21 as shown in FIG. 7, the illumination light can enter into the eye from positions deviated from the pupil center (specifically, point-symmetrical positions centered on the pupil center) when the pupil center of the subject's eye E is arranged on the optical axis O.

In the iris aperture 21, one or more apertures are formed so that a luminous flux cross section of the illumination light (illumination luminous flux cross section) and a luminous flux cross section of returning light from the subject's eye E (fundus Ef) (imaging luminous flux cross section) are separated on a reflective site in the path of the illumination light in the subject's eye E. The shape of the aperture(s) formed in the iris aperture is not limited, as long as the illumination luminous flux cross section and the imaging luminous flux cross section are separated at the reflective site described above. Examples of the reflective site include a cornea (anterior surface of cornea, posterior surface of cornea), an anterior surface of lens, and a posterior surface of lens.

For example, one or more apertures 21A and 21B are formed in the iris aperture 21, as shown in FIG. 7. The apertures 21A and 21B are formed line-symmetrically with respect to a straight line extending through the position of the optical axis O in a direction corresponding to a longitudinal direction of the slit 22.

Each of the apertures 21A and 21B has a circular segment shape. The circular segment is the region bounded by the inferior arc of a circle or ellipse and the chord of this inferior arc. A direction of the chord of the circular segment shape is approximately parallel to a direction corresponding to the longitudinal direction of the aperture(s) formed in slit 22.

In case of illuminating the subject's eye E using the iris aperture 21, the luminous flux cross section is formed on the pupil of the subject's eye E as shown in FIG. 8, for example.

In FIG. 8, light passing through the apertures 21A and 21B formed in the iris aperture 21 enters into the eye so as to form the luminous flux cross sections IR1 and IR2 on the pupil, for example. The luminous flux cross section IR1 is a luminous flux cross section of the light passing through the aperture 21A, for example. The luminous flux cross section IR2 is a luminous flux cross section of the light passing through the aperture 21B, for example.

The returning light (imaging light) that enters into the eye and is reflected on the fundus Ef forms the luminous flux cross section PR on the pupil, for example, and is guided to the imaging optical system 40.

In this case, the apertures 21A and 21B are formed so as to separate the luminous flux cross sections IR1 and IR2 of the illumination light and the luminous flux cross section PR of the imaging light.

The illumination luminous flux cross section and the imaging luminous flux cross section at each part of the eye of the subject's eye are formed as shown in FIG. 9. FIG. 9 schematically represents footprints FP1 to FP3 when the optical scanner 30 deflects with a predetermined deflection angle. The footprint FP1 represents the luminous flux cross section on the surface of the cornea. The footprint FP2 represents the luminous flux cross section on the anterior surface of lens (surface of the iris) (or surface of the photographic stop). The footprint FP3 represents the luminous flux cross section on the posterior surface of lens.

The anterior surface of lens (iris surface) (or surface of the photographic stop) is arranged at a position substantially conjugate optically to the iris aperture 21. Thereby, as shown in the footprint FP2, the same illumination luminous flux cross sections IR12 and IR22 and the imaging luminous flux cross section PR2 as in FIG. 9 are formed. The respective shapes of the illumination luminous flux cross sections IR12 and IR22 are almost the same as the respective shapes of the apertures 21A and 21B formed in the iris aperture 21. The shape of the imaging luminous flux cross section PR2 is almost the same as the shape of the photographic stop (aperture formed in the perforated mirror 45). At the position, which is substantially conjugate optically to the iris aperture 21, the illumination luminous flux cross section and the imaging luminous flux cross section are separated, as in the footprint FP2.

On the corneal surface, which is non-conjugate optically to the iris aperture 21, the illumination luminous flux cross sections IR11 and IR21 and the imaging luminous flux cross section PR1 spread in the direction corresponding to the longitudinal direction of the slit 22 (footprint FP1). Meanwhile, the relative relationship between the illumination luminous flux cross sections IR11 and IR21 and the imaging luminous flux cross section PR1 in the direction corresponding to the shorter direction of the slit 22 does not change.

In the same way, on the posterior surface of lens, which is non-conjugate optically to the iris aperture 21, the illumination luminous flux cross sections IR13 and IR23 and the imaging luminous flux cross section PR3 spread in the direction corresponding to the longitudinal direction of the slit 22 (footprint FP3). Meanwhile, the relative relationship between the illumination luminous flux cross sections IR13 and IR23 and the imaging luminous flux cross section PR3 in the direction corresponding to the shorter direction of the slit 22 does not change.

At the position, which is non-conjugate optically to the iris aperture 21, when the deflection angle of the illumination light is changed by the optical scanner 30, the positions of the illumination luminous flux cross section and the imaging luminous flux cross section move in the direction corresponding to the shorter direction of the slit 22. Even if the deflection angle changes, the relative relationship between the illumination luminous flux cross section and the imaging luminous flux cross section as shown in footprints FP1 and FP3 is maintained.

Therefore, the aperture 21A formed in the iris aperture 21 is required to be formed so that the distance d1 (distance in the direction corresponding to the shorter direction of the slit 22) between the lower end of the illumination luminous flux cross section (luminous flux cross section IR1) and the upper end of the imaging luminous flux cross section (luminous flux cross section PR) is greater than or equal to a predetermined first distance, as shown in FIG. 9. In the same way, the aperture 21B formed in the iris aperture 21 is required to be formed so that the distance d2 between the upper end of the illumination luminous flux cross section (luminous flux cross section IR2) and the lower end of the imaging luminous flux cross section (luminous flux cross section PR) is greater than or equal to a predetermined second distance, as shown in FIG. 8. Here, the first distance may be equal to the second distance. Further, the apertures 21A and 21B formed in the iris aperture 21 are required to be formed so that the distance d3 in the direction corresponding to the shorter direction of the slit 22 is greater than or equal to a predetermined third distance, as shown in FIG. 9.

That is, the shapes of the inner diameters of the apertures 21A and 21B does not contribute to the shapes of the illumination luminous flux cross section and the shape of the imaging luminous flux cross section.

As described above, the apertures 21A and 21B are formed in the iris aperture 21 so that the illumination luminous flux cross section and the imaging luminous flux cross section are separated at the cornea, the anterior surface of lens, and the posterior surface of lens of the subject's eye E. Thereby, without being affected by unnecessary scattered light, high quality images of the fundus Ef with strong contrast can be acquired using a simple configuration.

In particular, by shaping the apertures 21A and 21B as shown in FIG. 7, the light amount of the illumination light can be increased, making it possible to acquire images with higher image quality.

In addition, as shown in FIG. 10, the optical element 24 is arranged between the wavelength swept light source 10a (beam splitter 65) and the iris aperture 21. The optical element 24 can be arranged at a position substantially conjugate optically to the iris. The optical element 24 deflects the illumination light that have been transmitted through the beam splitter 65. The optical element 24 deflects the illumination light so that the light amount distribution in a direction connecting the aperture 21A (or aperture 21B) formed in the iris aperture 21 and the aperture formed in the slit 22 is maximized. Examples of such optical element include a prism, a microlens array, or a Fresnel lens. In FIG. 10, the optical element 24 is provided for each aperture formed in the iris aperture 21. However, a single element may be configured to deflect the light passing through the apertures 21A and 21B in the iris aperture 21.

Further, the light amount distribution of the light passing through the aperture formed in the iris aperture 21 can be changed by changing a relative position between the wavelength swept light source 10a and the aperture formed in the iris aperture 21.

(Slit 22)

Next, the slit 22 will be described. In the slit 22, the aperture that defines an irradiation pattern of the illumination light on the fundus Ef of the subject's eye E is formed.

The slit 22 can be moved in the optical axis direction of the illumination optical system 20 using a movement mechanism (movement mechanism 22D described below). The movement mechanism moves the slit 22 in the optical axis direction, under the control from the controller 100 described below. For example, the controller 100 controls the movement mechanism in accordance with the state of the subject's eye E. This allows to move the position of the slit 22 in accordance with the state of the subject's eye E (specifically, the dioptric power or the shape of the fundus Ef).

In some embodiments, the slit 22 is configured so that at least one of the position of the aperture and the shape of the aperture can be changed in accordance with the state of the subject's eye E without being moved in the optical axis direction. The function of the slit 22 like this is realized, for example, by a liquid crystal shutter.

(Relay Lens System RL1)

In FIG. 6, the optical system is configured according to Badal's principle. Specifically, the relay lens system RL1, relay lenses 41 and 44, and the objective lens 46 constitute a Badal optical system. This allows to keep the size of the slit image at the fundus Ef constant, regardless the dioptric power of the subject's eye E.

As shown in FIG. 12, a back focal position F1 of the relay lens system RL1 is arranged at a position substantially conjugate optically to the iris of the subject's eye E.

That is, the optical scanner 30, which is arranged at a position substantially conjugate optically to the iris of the subject's eye E as described above, is arranged at the back focal position F1 of the relay lens system RL1 or the vicinity of the back focal position F1. Therefore, even when the slit 22 is moved in the optical axis direction in accordance with the dioptric power of the subject's eye E, the size of the slit image (image formed by the light passing through the aperture formed in the slit 22) projected onto the fundus Ef does not change. This means that the projection magnification of the slit image onto the fundus Ef does not change even when the slit 22 moves in the optical axis direction.

As described above, according to the first embodiment, by arranging the optical scanner 30 at the back focal position F1 of the relay lens system RL1 (or the vicinity of the back focal position F1), the Badal optical system is configured with the relay lens system RL1, the relay lenses 41 and 42, and the objective lens 46.

This allows to keep the projected angle of view (projection magnification) of the slit image with reference to the visual axis of the subject's eye E (longitudinal and shorter directions of the slit 22) constant, regardless the dioptric power of the subject's eye E. As a result, the size of the slit image does not change regardless of the dioptric power of the subject's eye E. This allows to keep the deflection operation speed of the optical scanner 30 constant, and to simplify the control of the optical scanner 30.

In addition, since the projected angle of view (projection magnification) of the slit image with reference to the visual axis of the subject's eye E is constant regardless of the dioptric power of the subject's eye E, the illumination intensity of the slit image at the fundus Ef can be kept constant regardless of the dioptric power of the subject's eye E.

Further, in case of acquiring images at a predetermined imaging angle of view in the ophthalmic apparatus, since the projection magnification is constant as described above, this eliminates the need for a margin of the length in the longitudinal length of the slit 22 provided to acquire a slit image of a predetermined size.

(Relay Lens System RL2)

In addition, as shown in FIG. 6, the relay lens system RL2 is arranged between the slit 22 and the iris aperture 21.

As shown in FIG. 13, the iris aperture 21 is arranged at a front focal position F2 of the relay lens system RL2 or the vicinity of the front focal position F2.

That is, the back focal position F1 of the relay lens system RL1 is the position substantially conjugate optically to the iris aperture 21, and the iris aperture 21 is arranged at the front focal position F2 of the relay lens system RL2. Therefore, the projection magnification from the iris aperture 21 to the optical scanner 30 (arranged at the back focal position F1) is determined by a focal distance f1 of the relay lens system RL1 and a focal distance f2 of the relay lens system RL2. In this case, the projection magnification is (f1/f2).

The ophthalmic apparatus according to the embodiments is required to form images of the iris aperture 21 with a predetermined size on the iris of the subject's eye E. When the projection magnification from the iris of the subject's eye E to the optical scanner 30 via the objective lens 46 is a known projection magnification, an image of the iris aperture 21 of a predetermined size should be projected on the optical scanner 30. In this case, the projection magnification from the iris aperture 21 to the optical scanner 30 is determined by the focal distance f1 of the relay lens system RL1 and the focal distance f2 of the relay lens system RL2. Therefore, by changing at least one of the focal distances f1 and f2, the image of the iris aperture 21 can be easily formed on the iris of the subject's eye E with a predetermined size. In some embodiments, while the focal distance f1 remains fixed, the focal distance f2 is changed alone.

The focal distance f1 is a composite focal distance of the relay lens system RL1. In some embodiments, the relay lens system RL1 includes a plurality of the lenses with different dioptric powers, and changes the focal distance f1 by changing at least one of the lenses constituting the relay lens system RL1. In some embodiments, at least one of the lenses constituting the relay lens system RL1 is a lens whose dioptric power can be changed. Examples of the lens whose dioptric power can be changed include a liquid crystal lens, a liquid lens, and an Alvarez lens. Even when the focal distance f1 is changed, the back focal position of the relay lens system RL1 is arranged at a position substantially conjugate optically to the iris (pupil conjugate position) of the subject's eye E.

The focal distance f2 is a composite focal distance of the relay lens system RL2. In some embodiments, the relay lens system RL2 includes a plurality of the lenses with different dioptric powers, and changes the focal distance f2 by changing at least one of the lenses constituting the relay lens system RL2. In some embodiments, at least one of the lenses constituting the relay lens system RL2 is a lens whose dioptric power can be changed. Even when the focal distance f2 is changed, the front focal position of the relay lens system RL2 is arranged at a position substantially conjugate optically to the iris (pupil conjugate position) of the subject's eye E.

In addition, for imaging the fundus Ef, it is desirable to use a light source that emits a high-intensity light. However, light sources available for general use (light sources that are mass-produced) are limited in the size of the emitting surface (luminous area, output luminous flux cross section size). Thereby, the image of the iris aperture 21 should be projected onto the optical scanner 30 with a projection magnification corresponding to the size of the emitting surface of the light source.

According to this embodiment, by changing at least one of the focal distances f1 and f2, the projecting magnification from the iris aperture 21 to the optical scanner 30 can be changed. Thereby, the image of the iris aperture 21 with any size can be projected onto the optical scanner 30 with the desired size. This allows to project the image of the iris aperture 21 with a desired size onto the optical scanner 30 by simply changing at least one of the focal distances f1 and f2 even when the size of the emitting surface of the light source is different and to improve the degree of freedom in designing optical systems. In particular, this allows to fix the movement amount of the slit 22 in response to changes in the dioptric power of the subject's eye E (sensitivity of the movement of the slit 22 in response to changes in the dioptric power) by fixing the focal distance f1 and changing the focal distance f2 alone, and to further improve the degree of freedom in designing optical systems.

Further, according to the embodiments, the effective diameter of one or more lenses constituting the relay lens system RL1 can be reduced.

The reason for this is that the slit 22, which is arranged at a position substantially conjugate optically to the fundus Ef of the subject's eye E, is arranged between the optical scanner 30 and the iris aperture 21. The slit 22 can be moved in the optical axis direction in accordance with the dioptric power of the subject's eye E. Here, the projection magnification from the iris aperture 21 to the optical scanner 30 is determined by the first distance, which is a distance between the optical scanner 30 and the relay lens system RL1, and the second distance, which is a distance between the iris aperture 21 and the relay lens system RL1. Thereby, when the first distance is shortened, the second distance should also be shortened. However, since it is necessary to maintain the conjugate relationship with the iris and the conjugate relationship with the fundus Ef while securing the space for movement of the slit 22 in the optical axis direction, the first distance becomes longer and the effective diameter of the relay lens system RL1 becomes larger. According to this embodiment, by providing the relay lens system RL2, the projection magnification can be adjusted using the relay lens system RL2 even if the first distance is shortened. This allows to shorten the first distance while maintaining the conjugate relationship with the iris and the conjugate relationship with the fundus Ef and securing the space for movement of the slit 22 in the optical axis direction, and to reduce the effective diameter of the one or more lenses constituting the relay lens system RL1.

Further, since the effective diameter of the one or more lenses constituting the relay lens system RL1 can be reduced, the length of the optical system from the optical scanner 30 to the wavelength swept light source 10a can be reduced.

[Configuration of Control System]

Figure 14:
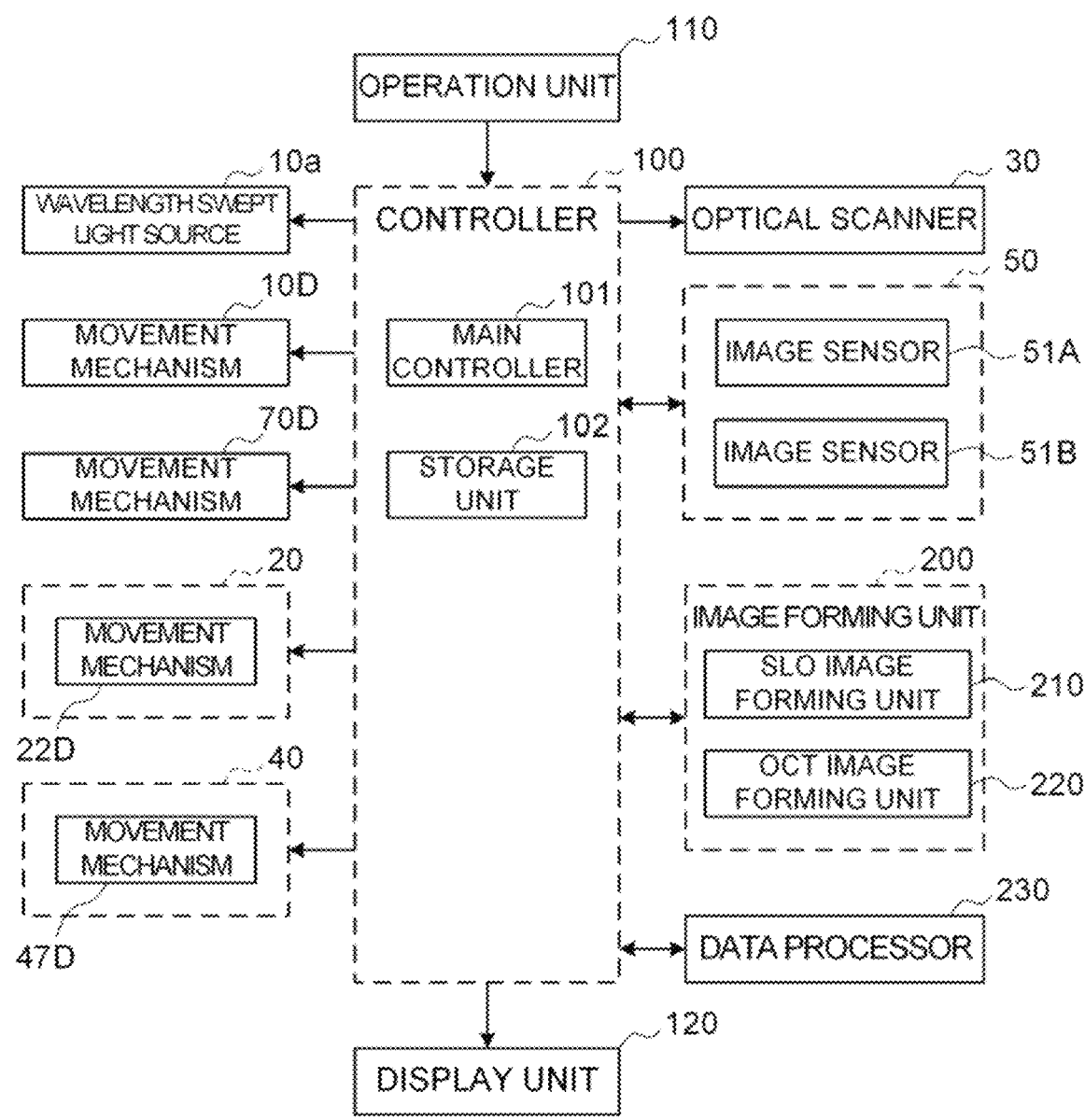
FIG. 14 is a diagram illustrating an example of the configuration of the control system of the ophthalmic apparatus according to the first embodiment.

FIG. 14 shows a block diagram of an example of the configuration of the control system of the ophthalmic apparatus 1 according to the first embodiment. In FIG. 14, like reference numerals designate like parts as in FIG. 2 or FIG. 6. The same description may not be repeated.

As shown in FIG. 14, the control system of the ophthalmic apparatus 1 is configured with a controller 100 as a center. It should be noted at least part of the configuration of the control system may be included in the optical system in the ophthalmic apparatus 1.

(Controller 100)

The controller 100 controls each part of the ophthalmic apparatus 1. The controller 100 includes a main controller 101 and a storage unit 102. The controller 100 realizes the functions of the timing controllers TC and TC1. The main controller 101 includes a processor and executes the control processing of each part of the ophthalmic apparatus 1 by executing processing according to the program(s) stored in the storage unit 102.

(Main Controller 101)

The main controller 101 performs control for the wavelength swept light source 10a, movement mechanisms 10D and 70D, control for the illumination optical system 20, control for the optical scanner 30, control for the imaging optical system 40, control for the imaging device 50, control for the image forming unit 200, and control for the data processor 230.

Examples of the control for the wavelength swept light source 10a include switching the light source on and off, switching the wavelength region of the emitted light of the light source, and changing the light amount of the light source.

The movement mechanism 10D changes at least one of the position of the wavelength swept light source 10a and the orientation of the wavelength swept light source 10a using a known mechanism, under the control from the controller 100. The main controller 101 can change at least one of the relative position of the wavelength swept light source 10a to the iris aperture 21 and the slit 22, and the relative orientation of the wavelength swept light source 10a to the iris aperture 21 and the slit 22.

The movement mechanism 70D moves the retroreflector 70 along the optical path of the reference light using a known mechanism, under the control from the controller 100. Thereby, the optical path length of the reference light is changed. Therefore, the difference between the optical path length of the measurement light and that of the reference light can be changed. This allows to arrange the site of interest in the OCT image generated based on the interference light generated by the beam combiner 62 at a desired position in the frame.

The control for the illumination optical system 20 includes control for the movement mechanism 22D. The movement mechanism 22D moves the slit 22 in the optical axis direction of the illumination optical system 20. The main controller 101 controls the movement mechanism 22D in accordance with the state of the subject's eye E to arrange the slit 22 at the position corresponding to the state of the subject's eye E. Examples of the state of the subject's eye E includes a shape of the fundus Ef, a dioptric power, and an axial length. The dioptric power can be obtained from a known eye refractive power measurement apparatus as disclosed in Japanese Unexamined Patent Application No. 61-293430 or Japanese Unexamined Patent Application Publication No. 2010-259495, for example. The axial length can be obtained from a known axial length measurement apparatus or a measurement value acquired by an optical coherence tomography.

For example, the storage unit 102 stores first control information. In the first control information, the positions of the slit 22 on the optical axis of the illumination optical system 20 are associated with the dioptric powers in advance. The main controller 101 specifies the position of the slit 22 corresponding to the dioptric power by referring to the first control information, and controls the movement mechanism 22D so as to arrange the slit 22 at the specified position.

Here, as the slit 22 moves, the light amount distribution of the light passing through the aperture formed in the slit 22 changes. In this case, as described above, the main controller 101 can control the movement mechanism 10D to change at least one of the position and the orientation of the wavelength swept light source 10a.

For example, as shown in FIG. 11, the position of the slit 22 is moved from the position of the slit 22' before the movement according to the state of the subject's eye E. Thereby, the light amount distribution of the light passing through the aperture formed in the slit 22 changes.

In this case, the main controller 101 controls the movement mechanism 10D to change the relative position between the iris aperture 21 and the wavelength swept light source 10a. By changing the relative position between the apertures 21A and 21B, which are formed in the iris aperture 21, and the wavelength swept light source 10a, the light amount distribution of the light passing through the apertures 21A and 21B is changed. Further, the light amount distribution of the light, which passes through the apertures 21A and 21B formed in the iris aperture 21, at the aperture formed in the slit 22 is changed.

The main controller 101 can control the movement mechanism 10D based on the dioptric power of the subject's eye E as the state of the subject's eye E and the position of the slit 22 after the movement (or movement direction and movement amount of the slit 22 with reference to a reference position).

For example, the storage unit 102 stores second control information. In the second control information, at least one of the positions and the orientations of the wavelength swept light source 10a are associated with the dioptric powers and the positions of the slit 22 after the movement (or the movement directions and movement amounts of the slit 22 with reference to the reference position) in advance. The main controller 101 specifies at least one of the position and the orientation of the wavelength swept light source 10a corresponding to the dioptric power or the position of the slit 22 after the movement by referring to the second control information, and controls the movement mechanism 10D so that the wavelength swept light source 10a is arranged at the specified position or in the specified orientation.

In FIG. 14, the control for the optical scanner 30 includes control of the scan range (scan start position and scan end position) and the scan speed. In some embodiments, in performing swept source type OCT, the controller 100 controls the optical scanner 30 so that the irradiated position of the illumination light deflected by the optical scanner 30 stays at least for a time sweeping a predetermined wavelength swept range.

The control for the imaging optical system 40 includes control for a movement mechanism 47D. The movement mechanism 47D moves the focusing lens 47 in the optical axis direction of the imaging optical system 40. The main controller 101 can control the movement mechanism 47D based on an analysis result of the image acquired using the image sensor 51A or the image sensor 51B. Further, the main controller 101 can control the movement mechanism 47D based on a content of operation of the user using an operation unit 110 described below.

Examples of the control for the imaging device 50 include a control for the image sensors 51A and 51B (rolling shutter control). Examples of the control for the image sensors 51A and 51B include reset control, exposure control, charge transfer control, and output control that are described below. Further, time Tr required for the reset control, time (exposure time) Te required for the exposure control, time Tc required for the charge transfer control, and time Tout required for the output control, etc., can be changed.

In the following, the rolling shutter control according to the embodiments will be described, using the image sensor 51A as an example.

The image sensor 51A includes the CMOS image sensor, as described above. In this case, the image sensor 51A includes a plurality of pixels (light receiving elements) arranged in a plurality of pixel groups in a column direction, the pixel groups being arranged in a row direction. Specifically, the image sensor 51A includes a plurality of pixels arranged two-dimensionally, a plurality of vertical signal lines, and a horizontal signal line. Each pixel includes a photodiode (light receiving element), and a capacitor. The vertical signal line is provided for each pixel group in the column direction (vertical direction) orthogonal to the row direction (horizontal direction). Each of the vertical signal lines is selectively electrically connected to the pixel group in which the electrical charge corresponding to the result of light reception is accumulated. The horizontal signal line is selectively electrically connected to the vertical signal lines. Each of the pixels accumulates the electrical charge corresponding to the light receiving result of the returning light. The accumulated electrical charge is read out sequentially for each pixel group in the row direction, for example. For example, for each line in the row direction, a voltage corresponding to the electrical charge accumulated in each pixel is supplied to the vertical signal line. The vertical signal lines are selectively electrically connected to the horizontal signal line. By performing readout operation for each line in the row direction described above sequentially in the vertical direction, the light receiving results of the plurality of pixels arranged two-dimensionally can be read out.

By capturing (reading out) the light receiving results of the return light using the rolling shutter method for this type of image sensor 51A, the light receiving image corresponding to the desired virtual aperture shape extending in the row direction is acquired. Such control is disclosed in, for example, U.S. Pat. No. 8,237,835.

Figure 15:
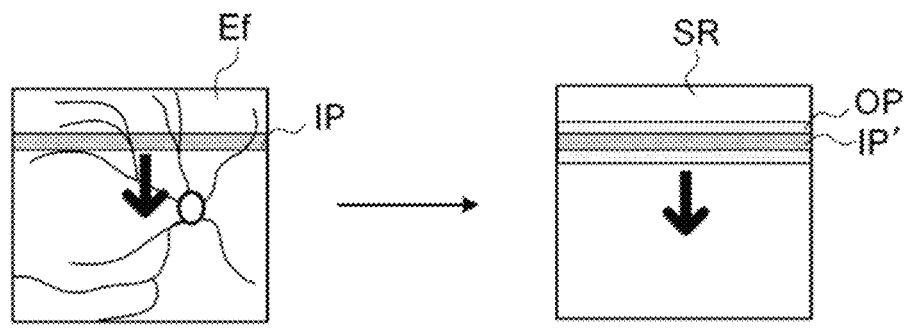
FIG. 15 is an explanatory diagram of an operation of the ophthalmic apparatus according to the first embodiment.

FIG. 15 shows a diagram explaining the operation of the ophthalmic apparatus 1 according to the embodiments. FIG. 15 schematically represents an irradiated range IP of the slit-shaped illumination light irradiated on the fundus Ef and a virtual opening range OP on the light receiving surface SR of the image sensor 51A.

For example, the controller 100 deflects the slit-shaped illumination light formed by the illumination optical system 20, using the optical scanner 30. Thereby, the irradiated range IP of the slit-shaped illumination light is sequentially moved in a direction (for example, the vertical direction) orthogonal to the slit direction (for example, the row direction, the horizontal direction) on the fundus Ef.

On the light receiving surface SR of the image sensor 51A, by changing the pixels to be read out by the controller 100 in units of lines, the virtual opening range OP is set. The opening range OP is preferable to be the light receiving range IP' of the returning light of the illumination light on the light receiving surface SR or wider than the light receiving range IP'. The controller 100 performs the movement control of the opening range OP in synchronization with the movement control of the irradiated range IP of the illumination light. Thereby, without being affected by unnecessary scattered light, high quality images of the fundus Ef with strong contrast can be acquired using a simple configuration.

Figure 16:
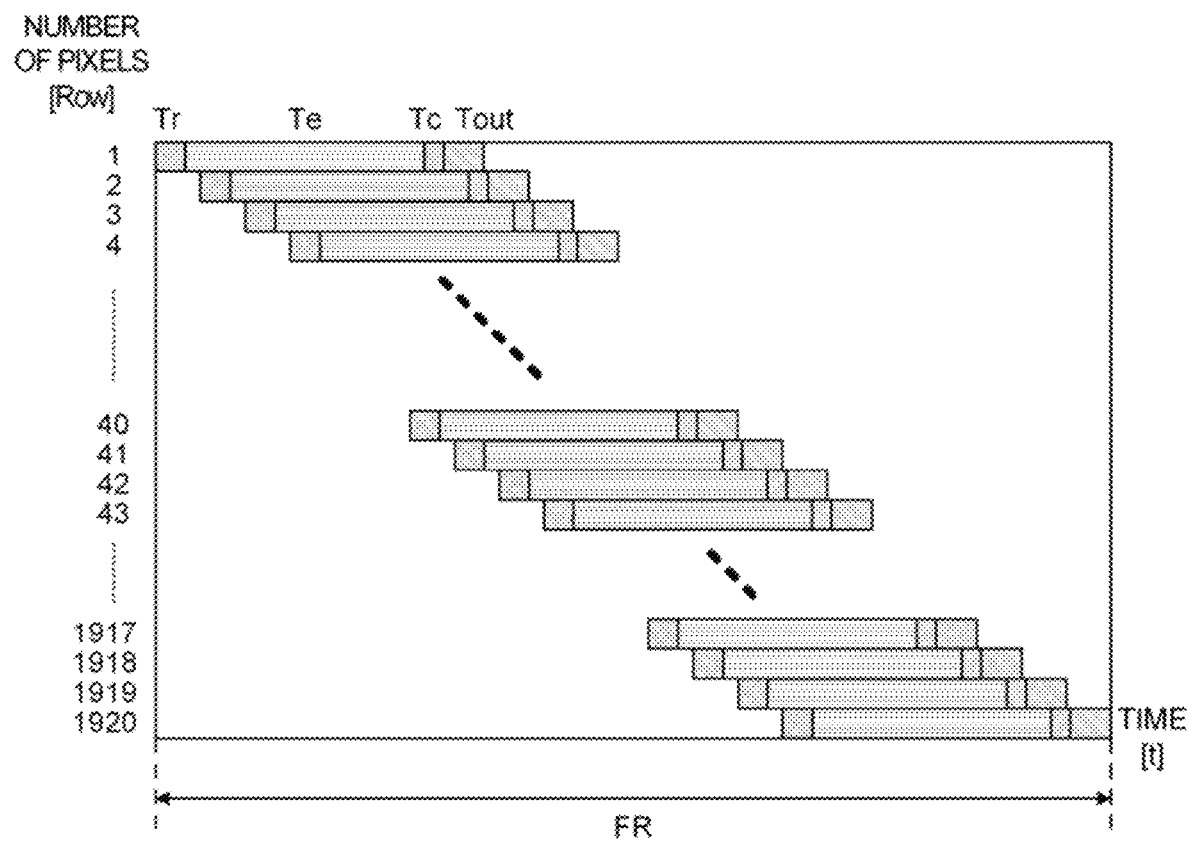
FIG. 16 is an explanatory diagram of an operation of the ophthalmic apparatus according to the first embodiment.
Figure 17:
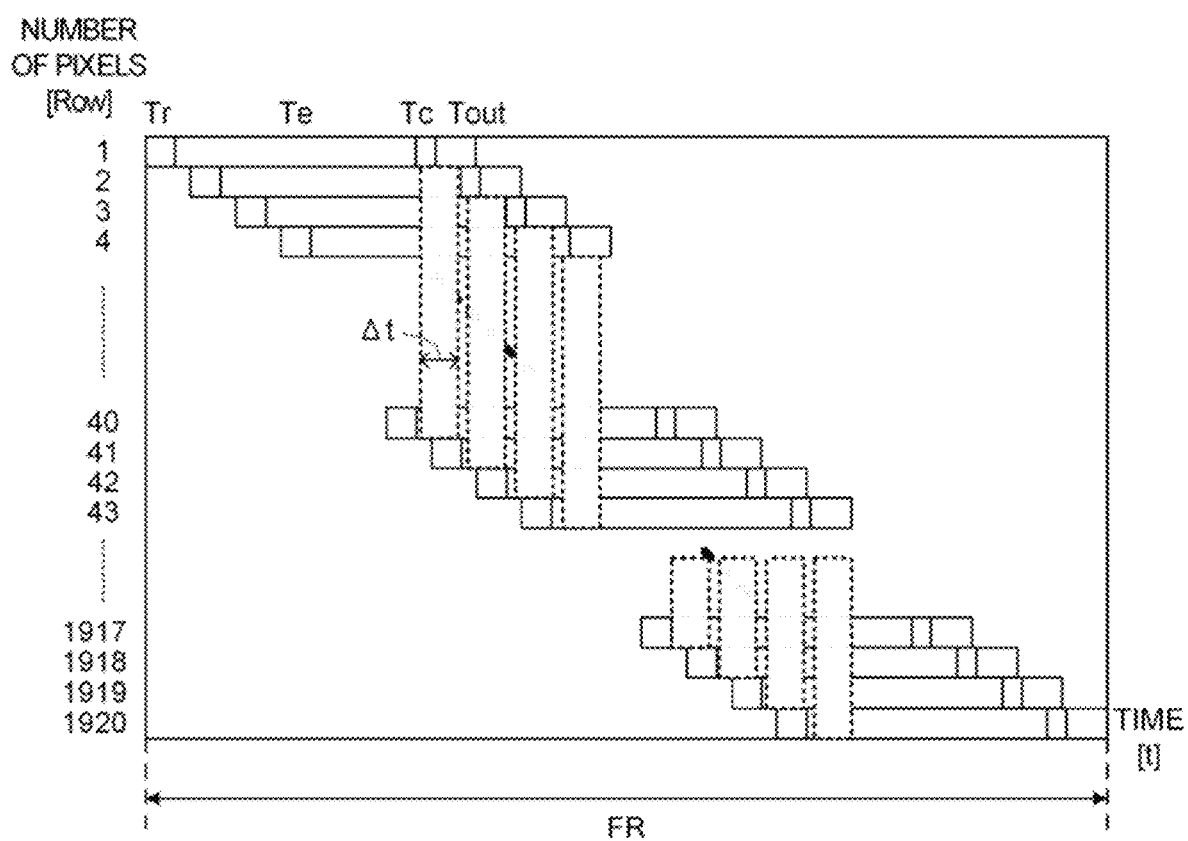
FIG. 17 is an explanatory diagram of an operation of the ophthalmic apparatus according to the first embodiment.

FIGS. 16 and 17 schematically show examples of the control timing of the rolling shutter method for the image sensor 51A. FIG. 16 represents an example of the timing of the readout control for the image sensor 51A. FIG. 17 represents the timing of the movement control for the irradiated range IP (the light receiving range IP') superimposed on the timing of the readout control in FIG. 16. In FIGS. 16 and 17, the horizontal axis represents the number of rows in the image sensor 51A, and the vertical axis represents time.

In addition, in FIGS. 16 and 17, for convenience of explanation, it is assumed that the number of rows in the image sensor 51A is 1920. However, the configuration according to the embodiments is not limited to the number of rows. Further, in FIG. 17, for convenience of explanation, it is assumed that the slit width (width in the row direction) of the slit-shaped illumination light is 40 rows.

The readout control in the row direction includes the reset control, the exposure control, the charge transfer control, and the output control. The reset control is a control that initializes the amount of electrical charge accumulated in the pixels in the row direction. The exposure control is a control that illuminates light on the photodiode and accumulates the electrical charge corresponding to the amount of received light in the capacitor. The charge transfer control is a control that transfers the amount of the electrical charge accumulated in the pixel to the vertical signal line. The output control is a control that outputs the amount of the electrical charge accumulated in the plurality of vertical signal lines via the horizontal signal line. That is, as shown in FIG. 16, the readout time T for reading out the electrical charge accumulated in the pixels in the row direction is the sum of the time Tr required for the reset control, the time Te required for the exposure control (exposure time), the time Tc required for the charge transfer control, and the time Tour required for the output control.

In FIG. 16, by shifting the readout start timing (start timing of time Tc) in units of rows, the light reception results (amount of electrical charge) accumulated in the pixels in the desired range in the image sensor 51A are acquired. For example, in case that the pixel range shown in FIG. 16 is for a single frame of the image, the frame rate FR is determined uniquely.

In this embodiment, the irradiated position of the illumination light on the fundus Ef, the illumination light having a slit width of a plurality of rows, is sequentially shifted in a direction corresponding to the column direction on the fundus Ef.

For example, as shown in FIG. 17, at each predetermined shift time Δt, the irradiated position of the illumination light on the fundus Ef is shifted in row units in the direction corresponding to the column direction. The shift time Δt is obtained by dividing the exposure time Te of the pixel in the image sensor 51A by the slit width of the illumination light (e.g., 40) (Δt=Te/40). Synchronized with this movement timing of this irradiated position, the readout start timing of each row of pixels is delayed and is started for each row in units of shift time Δt. This allows to acquired high quality images of the fundus Ef with strong contrast in a short time with a simple control.

In some embodiments, the image sensor 51A is configured using one or more line sensors.

In some embodiments, rolling shutter control is also performed for image sensor 51B as well as image sensor 51A.

In FIG. 14, the control for the image forming unit 200 includes a control that forms a light receiving image corresponding to an arbitrary opening range based on the light reception result(s) read out from the imaging device 50 using the rolling shutter method.

The image forming unit 200 forms the light receiving image corresponding to the arbitrary opening range based on the light reception result(s) read out from the image sensor 51A or the image sensor 51B using the rolling shutter method under the control from the main controller 101 (controller 100). The image forming unit 200 can sequentially form light receiving light images corresponding to the opening ranges and form an image of the subject's eye E from a plurality of formed light receiving images.

The image forming unit 200 includes the SLO image forming unit 210 and the OCT image forming unit 220.

The SLO image forming unit 210 forms a front image (SLO image, for example fundus image) of the subject's eye E based on a light receiving result acquired using the image sensor 51A. The SLO image forming unit 210 forms the front image based on the light receiving result(s) and the pixel position signal(s).

The OCT image forming unit 220 forms a tomographic image (OCT image) of the subject's eye E based on the light receiving result(s) of the interference light acquired using the image sensor 51B. For example, the light receiving results output from image sensor 51B are sampled based on a clock generated in synchronization with the output timing of each wavelength swept within a predetermined wavelength range by the wavelength swept light source 10a. The OCT image forming unit 220 can apply Fourier transform and the like to the spectral distribution based on the sampling data, for example, every series of wavelength scans (every A-line) to form the reflection intensity profile in each A-line. The OCT image forming unit 220 can form a tomographic image by imaging the reflection intensity profile in each A-line.

The image forming unit 200 includes one or more processors and executes the function described above by performing processing corresponding to the program(s) stored in the storage unit or the like.

Example of the control for the data processor 230 include various kinds of image processing and various kinds of analysis processing on the light receiving results acquired from the imaging device 50. Examples of the image processing include noise removal processing on the light receiving results, brightness correction processing for easily identifying a predetermined site depicted in the light receiving image based on the light receiving results. Examples of the analysis processing include a specifying processing of the in-focus state.

The data processor 230 executes various kind of data processing. Examples of the data processing include data processing on the image formed by the image forming unit 200. Examples of this processing include image processing, image analyzing, image evaluation, diagnosis support, and the like. For example, the data processor 230 performs correction processing such as brightness correction of images and/or dispersion correction of images. Further, the data processor 230 performs various kinds of image processing and various kinds of analysis processing on the front image and the tomographic image. The data processor 230 can form volume data (voxel data) of the subject's eye E by performing known image processing such as interpolation processing for interpolating pixels between cross sectional images. In the case of displaying an image based on the volume data, the data processor 230 performs rendering processing on the volume data so as to form a pseudo three-dimensional image viewed from a specific line-of-sight direction.

In addition, the data processor 230 can form a C-mode image, a projection image, a shadowgram, or the like from the volume data. The C-mode image is formed by selecting pixels (voxels) on a designated cross section from the three-dimensional data set. The projection image is formed by projecting the three-dimensional data set in a predetermined direction (Z direction, depth direction, axial direction). The shadowgram is formed by projecting a part of the three-dimensional data set (for example, partial data corresponding to a specific layer) in a predetermined direction.

The data processor 230 includes one or more processors and executes the function described above by performing processing corresponding to the program(s) stored in the storage unit or the like.

In some embodiments, at least one of the position of the optical element 24 and the orientation of the optical element 24 with respect to the aperture(s) formed in the iris aperture 21 can be changed. For example, the main controller 101 can change the at least one of the position of the optical element 24 and the orientation of the optical element 24 by controlling the movement mechanism that moves the optical element 24.

(Storage Unit 102)

The storage unit 102 stores various computer programs and data. The computer programs include an arithmetic program and a control program for controlling the ophthalmic apparatus 1.

(Operation Unit 110)

The operation unit 110 includes an operation device or an input device. The operation unit 110 includes buttons and switches (e.g., operation handle, operation knob, etc.) and operation devices (e.g., mouse, keyboard, etc.) provided in the ophthalmic apparatus 1. In addition, the operation unit 110 may include any operation device or any input device, such as a trackball, a control panel, a switch, a button, a dial, etc.

(Display Unit 120)

The display unit 120 displays the image of the subject's eye E generated by the image forming unit 200. The display unit 120 is configured to include a display device such as a flat panel display such as an LCD (Liquid Crystal Display). In addition, the display unit 120 may include various types of display devices such as a touch panel and the like provided in the housing of the ophthalmic apparatus 1.

It should be noted that the operation unit 110 and the display unit 120 do not need to be configured to be separate devices. For example, a device like a touch panel, which has a display function integrated with an operation function, can be used. In this case, the operation unit 110 includes the touch panel and a computer program. The content of an operation performed using the operation unit 110 is fed to the controller 100 as an electrical signal. Moreover, operations and inputs of information may be performed using a graphical user interface (GUI) displayed on the display unit 120 and the operation unit 110. In some embodiments, the functions of the display unit 120 and the operation unit 110 are realized a touch screen.

(Other Configurations)

In some embodiments, the ophthalmic apparatus 1 further includes a fixation projection system. Further, an optical path of the fixation projection system is coupled with the optical path of the imaging optical system 40 in the configuration of the optical system shown in FIG. 1. The fixation projection system can present internal fixation targets or external fixation targets to the subject's eye E. In case of presenting the internal fixation target to the subject's eye E, the fixation projection system includes an LCD that displays the internal fixation target under the control from the controller 100, and projects a fixation light flux output from the LCD onto the fundus Ef of the subject's eye E. The LCD is configured to be capable of changing the display position of the fixation target on the screen of the LCD. By changing the display position of the fixation target on the screen of the LCD, the projected position of the fixation target on the fundus of the subject's eye E can be changed. The display position of the fixation target on the LCD can be designated using the operation unit 110 by the user.

In some embodiments, the ophthalmic apparatus 1 includes an alignment system. In some embodiments, the alignment system includes an XY alignment system and a Z alignment system. The XY alignment system is used for position matching between the optical system of the apparatus and the subject's eye E in a direction intersecting the optical axis of the optical system of the apparatus (objective lens 46). The Z alignment system is used for position matching between the optical system of the apparatus and the subject's eye E in a direction of the optical axis of the ophthalmic apparatus 1 (objective lens 46).

For example, the XY alignment system projects a bright spot (bright spot in the infrared region or near-infrared region) onto subject's eye E. The data processor 230 acquires an anterior segment image of the subject's eye E on which the bright spot is projected, and obtains the displacement between the bright spot image drawn on the acquired anterior segment image and an alignment reference position. The controller 100 relatively moves the optical system of the apparatus and the subject's eye E in the direction intersecting the direction of the optical axis so as to cancel the obtained displacement, using the movement mechanism.

For example, the Z alignment system projects alignment light in infrared region or the near-infrared region from a position away from the optical axis of the optical system of the apparatus, and receives the alignment light reflected on the anterior segment of the subject's eye E. The data processor 230 specifies a distance to the subject's eye E with respect to the optical system of the apparatus, from the light receiving position of the alignment light that changes in accordance with the distance to the subject's eye E with respect to the optical system of the apparatus. The controller 100 relatively moves the optical system of the apparatus and the subject's eye E in the direction of the optical axis using the movement mechanism (not shown) so that the specified distance becomes a predetermined working distance.

In some embodiments, the function of the alignment system is realized by two or more anterior segment cameras arranged at positions away from the optical axis of the optical system of the apparatus. For example, as disclosed in Japanese Unexamined Patent Application Publication No. 2013-248376, the data processor 230 analyzes data processor segment images of subject's eye E substantially simultaneously acquired using the two or more anterior segment cameras, and specifies a three-dimensional position of the subject's eye E using known trigonometry. The controller 100 controls the movement mechanism (not shown) to relatively move the optical system of the apparatus and the subject's eye E three-dimensionally so that the optical axis of the optical system of the apparatus substantially coincides with an axis of the subject's eye E and the distance of the optical system of the apparatus with respect to the subject's eye E is a predetermined working distance.

In the first embodiment, a case where the light receiving results are captured by the rolling shutter method using at least one of the image sensors 51A and 51B has been described. However, the configuration according to the embodiments is not limited thereto. In the first embodiment, for example, the light receiving results may be captured by the global shutter method or the TDI method using at least one of the image sensors 51A and 51B.

The relay lens system RL1 is an example of the "first relay lens system" according to the embodiments. The relay lens system RL2 is an example of the "second relay lens system" according to the embodiments. The movement mechanism 22D is an example of the "first movement mechanism" according to the embodiments. The movement mechanism 10D is an example of the "second movement mechanism" according to the embodiments. A movement mechanism (not shown) that changes at least one of the position of the optical element 24 and the orientation of the optical element 24 is an example of the "third movement mechanism" according to the embodiments.

[Operation]

Next, the operation of the ophthalmic apparatus 1 will be described.

Figure 18:
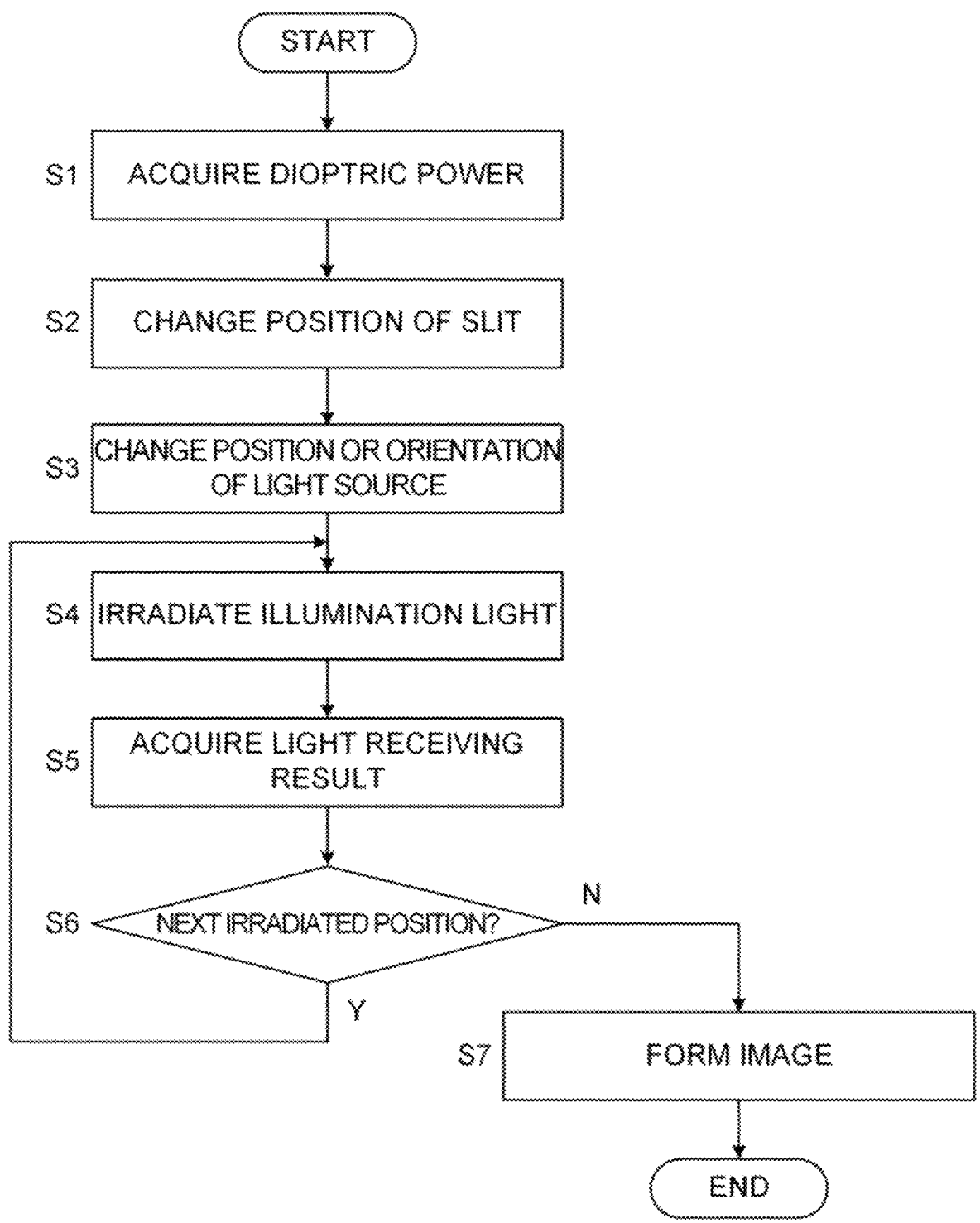
FIG. 18 is a flowchart illustrating an example of an operation of the ophthalmic apparatus according to the first embodiment.

FIG. 18 shows a flowchart of an example of the operation of the ophthalmic apparatus 1 according to the first embodiment. The storage unit 102 stores a computer program for realizing the processing shown in FIG. 18. The main controller 101 operates according to the computer program, and thereby the main controller 101 performs the processing shown in FIG. 18.

Here, it is assumed that the alignment of the optical system of the apparatus with respect the subject's eye E using the alignment system (not shown) is completed, and that the fixation target is projected onto the fundus of the subject's eye E to guide the subject's eye E to a desired fixation position using the fixation projection system (not shown).

(S1: Acquire Dioptric Power)

First, the main controller 101 acquires the dioptric power of the subject's eye E from an external ophthalmic measurement apparatus or an electronic medical record.

(S2: Change Position of Slit)

Next, the main controller 101 changes the position of the slit 22 on the optical axis of the illumination optical system 20 in accordance with the dioptric power of the subject's eye E acquired in step S1.

Specifically, the main controller 101 specifies the position of the slit 22 corresponding to the dioptric power by referring to the first control information stored in the storage unit 102, and controls the movement mechanism 22D so as to arrange the slit 22 at the specified position.

(S3: Change Position or Orientation of Light Source)

Subsequently, the main controller 101 changes at least one of the position of the wavelength swept light source 10*a* and the orientation of the wavelength swept light source 10*a* in accordance with the new position of the slit 22 whose position on the optical axis has been changed in step S2.

Specifically, the main controller 101 specifies at least one of the position and the orientation of the wavelength swept light source 10*a* corresponding to the dioptric power or the position of the slit 22 after movement, by referring to the second control information stored in the storage unit 102. And then, the main controller 101 controls the movement mechanism 10D so that the wavelength swept light source 10*a* is arranged at the specified position or in the specified orientation.

(S4: Irradiate Illumination Light)

Next, the main controller 101 controls the wavelength swept light source 10*a* and the illumination optical system 20 to generate the slit-shaped illumination light, and to start the deflection control of the optical scanner 30 to start irradiating the illumination light onto the desired irradiated region on the fundus Ef. When the irradiation of the illumination light is started, the slit-shaped illumination light is sequentially irradiated within the desired irradiated range as described above.

(S5: Acquire Light Receiving Result)

The main controller 101 acquires the light receiving results of the pixels in the opening range of the image sensors 51A and 51B corresponding to the irradiated range of the illumination light on the fundus Ef performed in step S4, as described above.

(S6: Next Irradiated Position?)

The main controller 101 determines whether or not the next irradiated position is to be irradiated with the illumination light. The main controller 101 can determine whether or not the next irradiated position is to be irradiated with the illumination light, by determining whether or not the irradiated range of the illumination light that is moved sequentially has covered a predetermined imaging range of the fundus Ef.

When it is determined that the next irradiated position is to be irradiated with the illumination light (S6: Y), the operation of the ophthalmic apparatus 1 proceeds to step S4. When it is determined that the next irradiated position is not to be irradiated with the illumination light (S6: N), the operation of the ophthalmic apparatus 1 proceeds to step S7.

(S7: Form Image)

In step S6, when it is determined that the next irradiated position is not to be irradiated with the illumination light (S6: N), the main controller 101 controls the image forming unit 200 to form the image of the subject's eye E from the light receiving results acquired repeatedly while changing the irradiated range of the illumination light in step S5.

For example, the image forming unit 200 performs the forming of the front image and the forming of the tomographic image in parallel. In this case, the SLO image forming unit 210 syntheses a plurality of light receiving results with different irradiated ranges (opening ranges on the light receiving surface SR of the image sensor 51A) of the illumination light for the number of times repeating the process in step S4 to S6, based on the order of the movement of the irradiated range. Thereby, the fundus image of the fundus Ef for one frame is formed. In addition, the OCT image forming unit 220 syntheses a plurality of light receiving results with different irradiated ranges of the illumination light for the number of times repeating the process in step S4 to S6, based on the order of the movement of the irradiated range. Thereby, the tomographic image of the fundus Ef is formed.

In some embodiments, in step S7, the image forming unit 200 forms one of the front image and the tomographic image, and then forms the other. In some embodiments, in step S7, the image forming unit 200 forms any one of the front image and the tomographic image.

In some embodiments, in step S4, the illumination light is irradiated on the irradiated range set so as to have an overlapping region with the adjacent irradiated range. Thereby in step S7, the fundus image for one frame is formed by synthesizing the overlapping regions so as to overlap with each other.

This terminates the operation of the ophthalmic apparatus 1 (END).

As described above, according to the first embodiment, the front image and the tomographic image of the subject's eye E are formed based on the returning light of the illumination light and the interference light, while sharing the light source, the scan optical system, and the detector. This allows to observe the subject's eye in detail with a simple configuration. In particular, by separately providing the SLO detector and the OCT detector, the front image and the tomographic image of the subject's eye E can be formed while receiving the returning light and the interference light simultaneously.

Further, the light source and the like for acquiring the front image and the tomographic image are shared. This allows to perform position matching between the acquired front image and the acquired tomographic image of the subject's eye E with high accuracy. As a result, the site of interest of the subject's eye E can be observed in detail.

Further, at least the scan optical system and the detector are synchronized using the rolling shutter method. This allows to acquire high quality images with a simple configuration.

Modification Example of First Embodiment

The configuration of the ophthalmic apparatus according to the embodiments is not limited to the configuration described in the first embodiment. For example, the SLO detector DS may be configured to separately receive the returning light of two or more wavelength regions different from each other.

Figure 19:
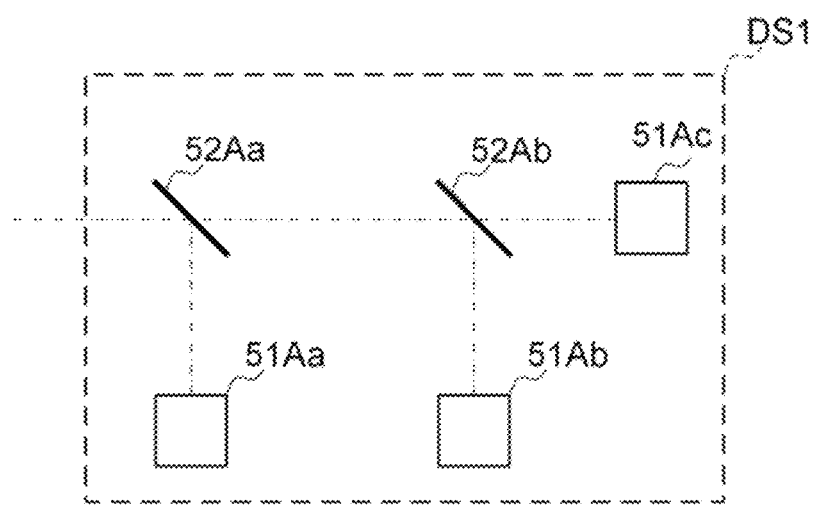
FIG. 19 is a schematic diagram illustrating an example of the configuration of the optical system of the ophthalmic apparatus according to a modification example of the first embodiment.

FIG. 19 shows a block diagram of an example of the configuration of the SLO detector according to a modification example of the first embodiment. An ophthalmic apparatus according to the modification example of the first embodiment includes an SLO detector DS1 according to the present modification example instead of the SLO detector DS or the image sensor 51A.

The SLO detector DS1 includes image sensors 51Aa, 51Ab, and 51Ac, and dichroic beam splitters 52Aa and 52Ab. The dichroic beam splitter 52Aa guides light in a first wavelength region of the returning light of the illumination light to the image sensor 51Aa, and transmits light in a second wavelength region different from the first wavelength region. The dichroic beam splitter 52Ab guides light in a third wavelength region of the light in the second wavelength region to the image sensor 51Ab, and transmits light in a fourth wavelength region different from the third wavelength region. Thereby, the image sensors 51Aa, 51Ab, and 51Ac receive light in different wavelength regions from each other.

The SLO image forming unit 210 forms a first front image based on the light receiving results acquired by the image sensor 51Aa, forms a second front image based on the light receiving results acquired by the image sensor 51Ab, and forms a third front image based on the light receiving results acquired by the image sensor 51Ac. The SLO image forming unit 210 can form a synthetic image by synthesizing two or more images among the first front image, the second front image, and the third front image.

In some embodiments, a front image of each RGB color component is formed by generating the illumination light using light from a white light source.

Second Embodiment

The configuration according to the embodiments can be applied to an ophthalmic apparatus using other types of OCT (spectral domain type OCT or time domain OCT) other than the swept source type described in the first embodiment.

In the following, the second embodiment will be described with a focus on differences from the first embodiment.

Figure 20:
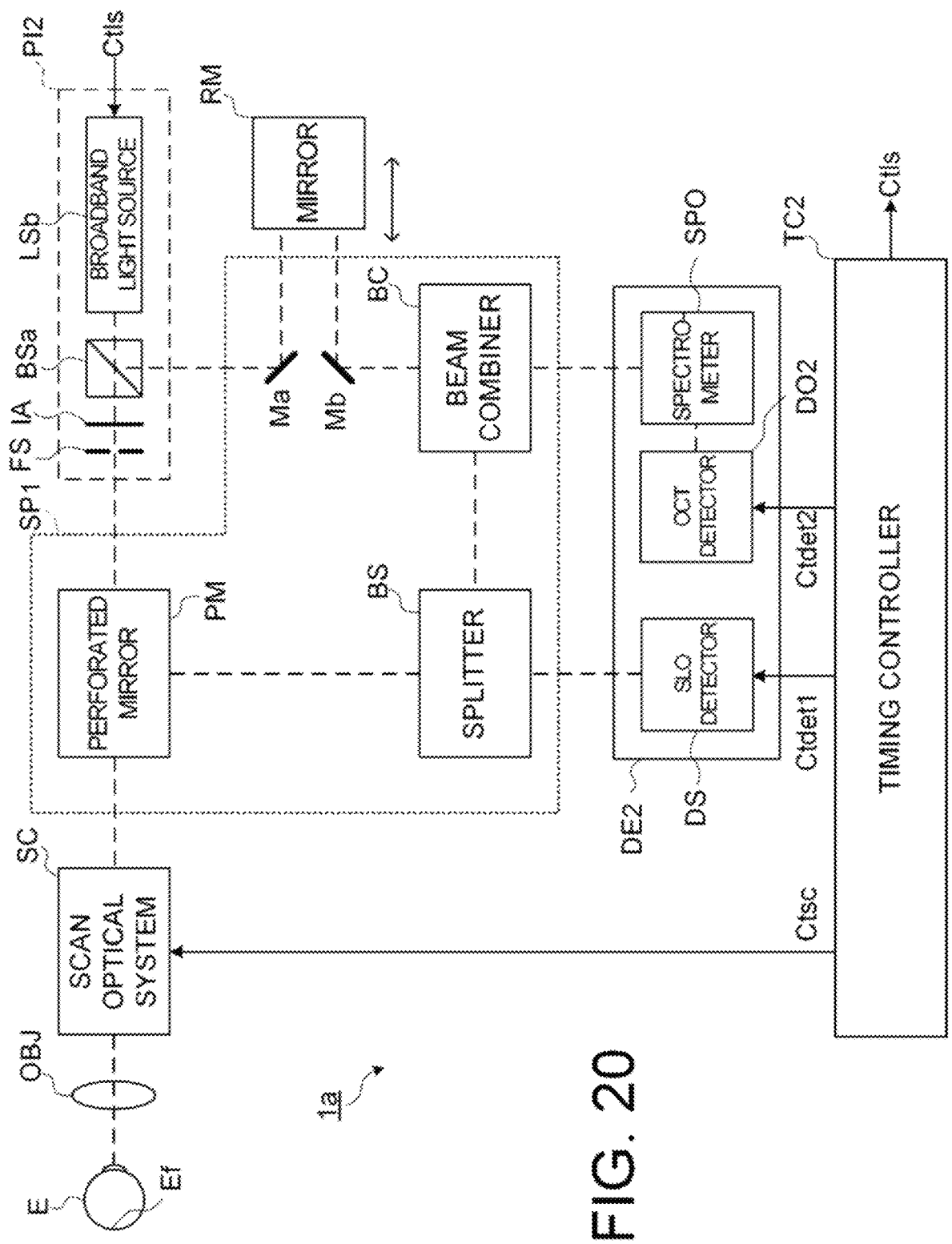
FIG. 20 is a schematic diagram illustrating an example of a configuration of an optical system of an ophthalmic apparatus according to a second embodiment.

FIG. 20 shows a block diagram of an example of a configuration of an ophthalmic apparatus 1a according to the second embodiment. In FIG. 20, like reference numerals designate like parts as in FIG. 5. The same description may not be repeated.

The difference between the configuration of the ophthalmic apparatus 1a and the configuration of the ophthalmic apparatus 1 shown in FIG. 5 is mainly that a pattern illumination optical system PI2 is provided instead of the pattern illumination optical system PI1 that a detector DE2 is provided instead of the detector DE1, and that a timing controller TC2 is provided instead of the timing controller TC1.

The difference between the configuration of the pattern illumination optical system PI2 and the configuration of the pattern illumination optical system PI1 shown in FIG. 5 is that a broadband light source LSb is provided instead of the wavelength swept light source LSa. The broadband light source includes, for example, a super luminescent diode (SLD) or a light emitting diode (LED). The broadband light source has, for example, a near-infrared wavelength and a temporal coherence length of about several tens of micrometers.

The configuration of the detector DE2 differs from the configuration of the detector DE1 shown in FIG. 5 in that a spectrometer SPO and an OCT detector DO2 are provided instead of the OCT detector DO1.

The spectrometer SPO disperses the interference light generated by the beam combiner BC. For example, the spectrometer SPO decomposes the interference light into spectral components using a diffraction grating. The interference light decomposed into spectral components by the spectrometer SPO is received by the OCT detector DO2.

The timing controller TC2 controls each part to perform the known spectral domain type OCT.

Hereinafter, a specific configuration example of the ophthalmic apparatus 1a according to the second embodiment will be described.

Figure 21:
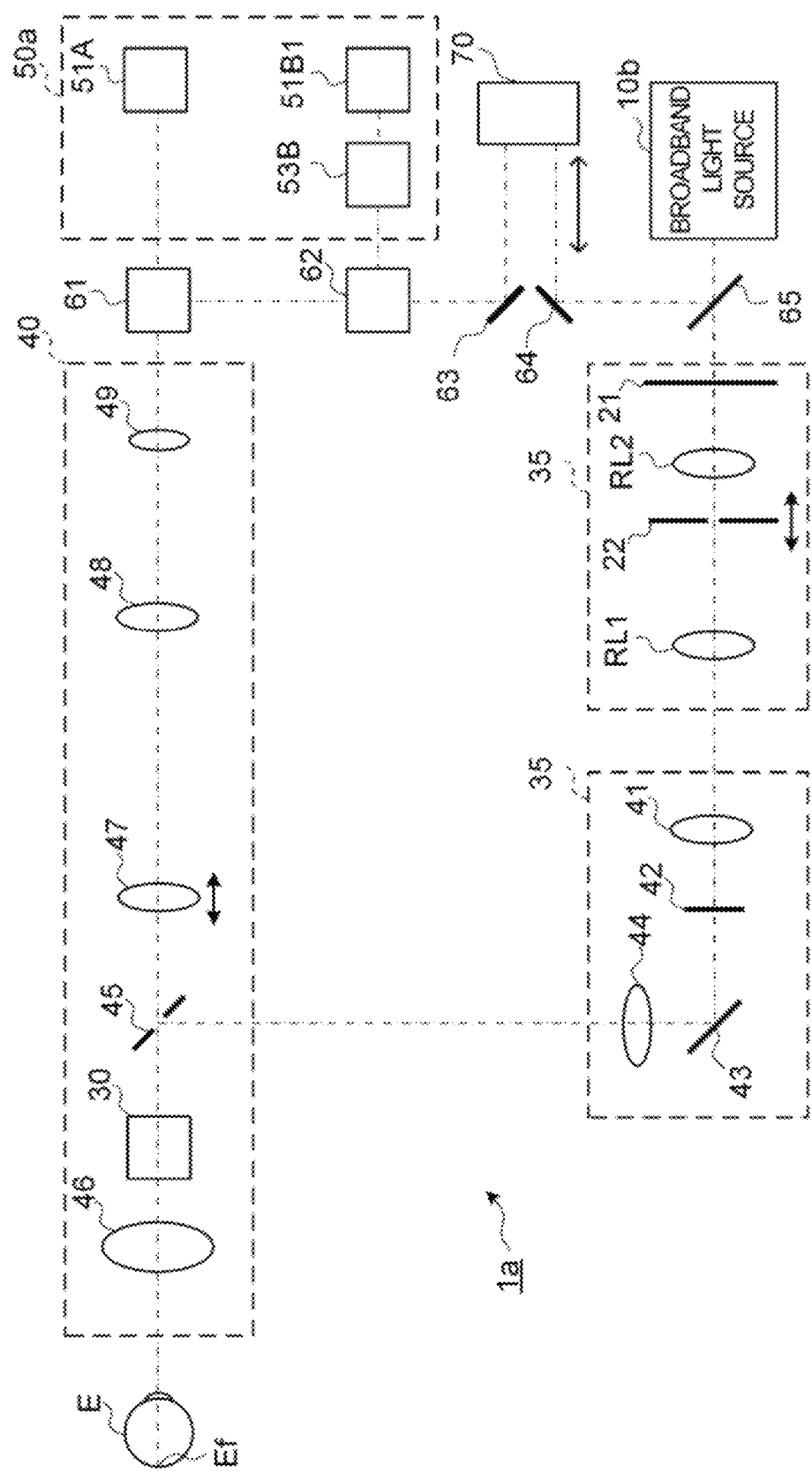
FIG. 21 is a diagram illustrating an example of the configuration of the optical system of the ophthalmic apparatus according to the second embodiment.

FIG. 21 shows an example of the configuration of an optical system of the ophthalmic apparatus 1a according to the second embodiment. In FIG. 21, parts similar to those in FIG. 6 are denoted by the same reference symbols, and description thereof is appropriate.

In FIG. 21, a broadband light source 10b is provided instead of the wavelength swept light source 10a in FIG. 6. Further, an imaging device 50a is provided instead of the imaging device 50 in FIG. 6. The imaging device 50a includes the image sensor 51A, a spectrometer 53B, and an image sensor 51B1.

In other words, the broadband light source 10b corresponds to the broadband light source LSb in FIG. 20. The first returning light split by the beam splitter 61 is received by the image sensor 51A. The spectrometer 53B decomposes the interference light generated by the beam combiner 62 into spectral components using the diffraction grating. The image sensor 51B1 receives the interference light decomposed into the spectral components by the spectrometer 53B. The image sensor 51B1 is, for example, a line sensor, and detects the spectral components of the interference light to generate an electric signal (that is, a detection signal).

In the second embodiment, a case where the configuration shown in FIG. 20, which changes the optical path length of the reference light, has been described as an example. However, the configuration of the second embodiment can be applied to the configuration shown in FIG. 4, which changes the optical path length of the illumination light.

According to the second embodiment, the same effects as in the first embodiment can be achieved.

Third Embodiment

In the above embodiments, cases where the subject's eye E is irradiated with the illumination light by deflecting the illumination light incident through the splitter SP. However, the configuration according to the embodiments is not limited thereto. In a third embodiment, the illumination light deflected by the scan optical system SC is irradiated onto the subject's eye E through the splitter SP.

In the following, the third embodiment will be described with a focus on differences from the first embodiment.

Figure 22:
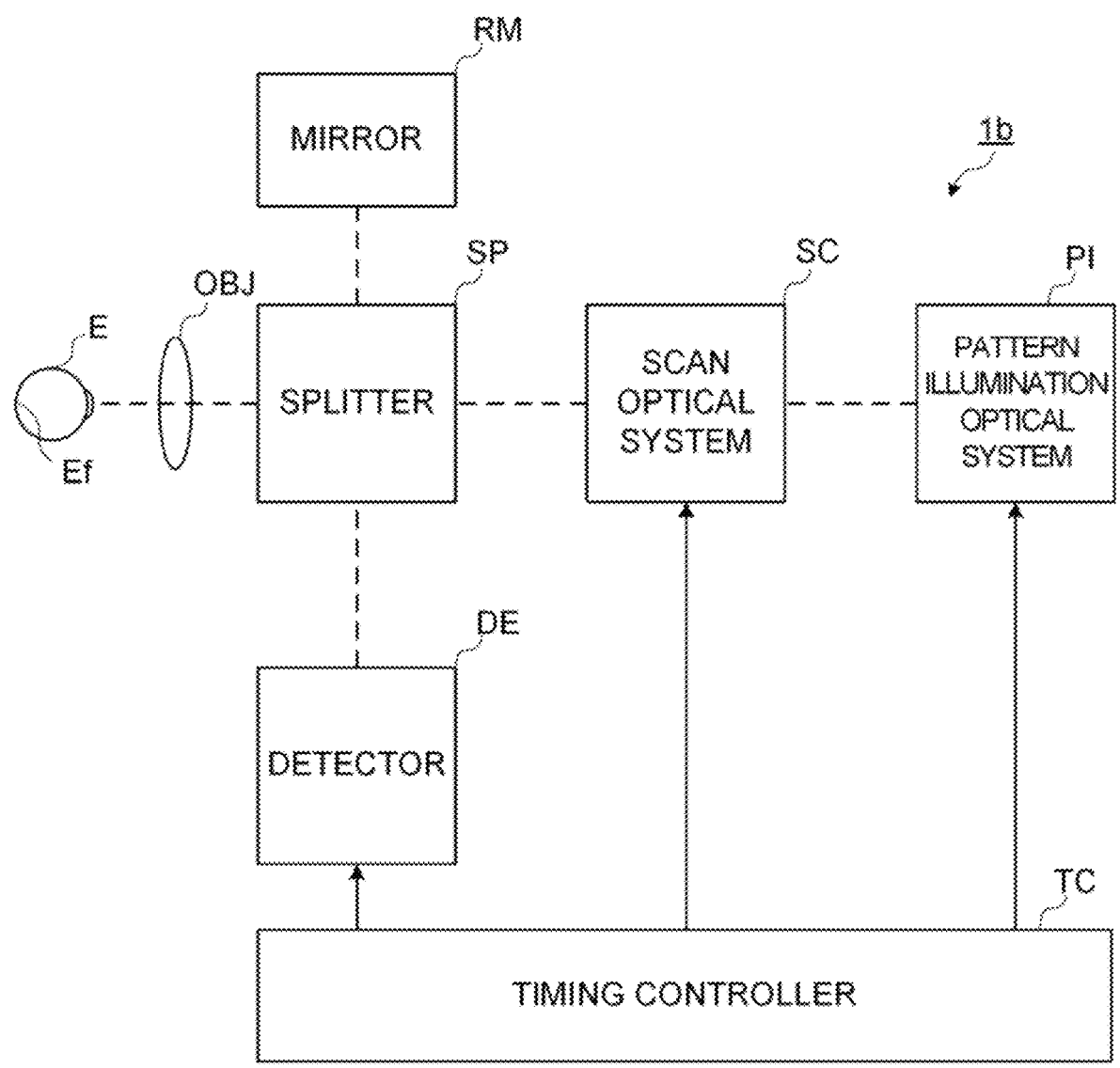
FIG. 22 is a schematic diagram illustrating an example of the configuration of the ophthalmic apparatus according to the second embodiment.

FIG. 22 shows a block diagram of an example of a configuration of an ophthalmic apparatus according to the third embodiment. In FIG. 22, like reference numerals designate like parts as in FIG. 1. The same description may not be repeated.

The ophthalmic apparatus 1b according to the third embodiment includes the pattern illumination optical system PI, the scan optical system SC, the splitter SP, the mirror RM, the objective lens OBJ, the detector DE, and the timing controller TC, as in the ophthalmic apparatus 1 according to the first embodiment.

The configuration of the ophthalmic apparatus 1b differs from the configuration of the ophthalmic apparatus 1 shown in FIG. 1 in the arrangement of the scan optical system SC and the splitter SP. That is, in the ophthalmic apparatus 1b, the illumination light generated by the pattern illumination optical system PI is deflected by the scan optical system SC, and the deflected illumination light is split into light guided to be objective lens OBJ and light guided to the mirror RM by the splitter SP.

Specifically, the pattern illumination optical system PI generates the illumination light and the reference light using light from the light source. The illumination light generated by the pattern illumination optical system PI enters into the scan optical system SC. The scan optical system SC deflects the illumination light from the pattern illumination optical system PI, and guides the deflected illumination light to the splitter SP. The splitter SP guides the illumination light deflected by scan optical system SC into the illumination optical path (measurement optical path), and guides the reference light into the reference optical path. The objective lens OBJ is arranged in the illumination optical path. The mirror RM is arranged in the reference optical path The illumination light transmitted through the splitter SP is refracted by the objective lens OBJ, enters into the eye through the pupil of the subject's eye E, and is irradiated onto the fundus Ef of the subject's eye E. The returning light of the illumination light irradiated onto the fundus Ef passes through the objective lens OBJ, and enters the splitter SP.

The reference that has been guided to the reference optical path is reflected by the mirror RM, and returns to the splitter SP.

The splitter SP generates the interference light (combined light) between the returning light of the illumination light from the subject's eye E passing through the illumination optical path and the reference light passing through the reference optical path. That is, the splitter SP guides the illumination light from the pattern illumination optical system PI to the subject's eye E, and generates the interference light between the reference light and the returning light of the illumination light from the subject's eye E.

The detector DE detects the returning light of the illumination light from the subject's eye E passing through the illumination optical path and the interference light generated by the splitter SP, via the splitter SP. The detector DE can output the light receiving result using the rolling shutter method, the global shutter method, or the TDI method under the control from the timing controller TC, in the same way as in the first embodiment.

Figure 23:
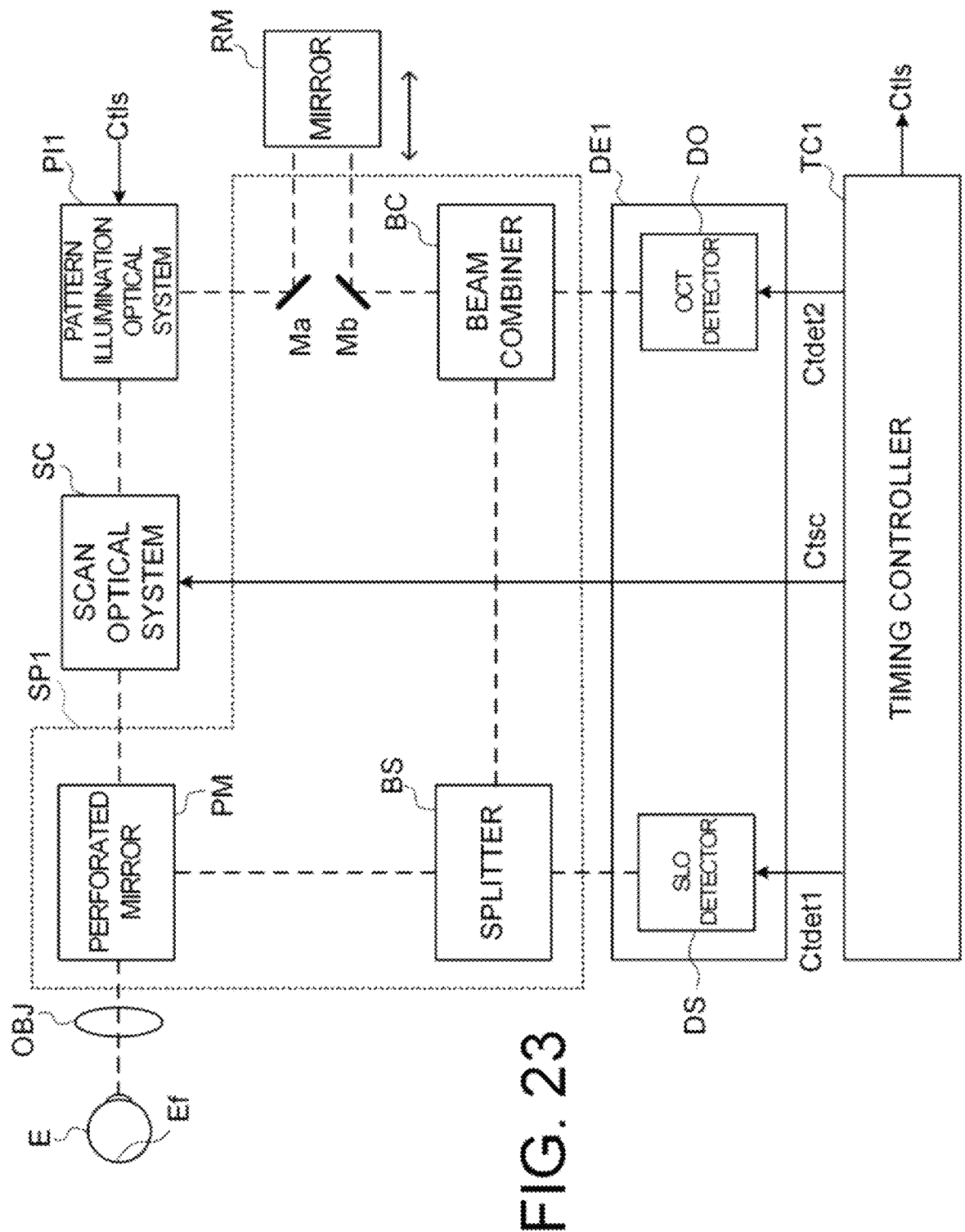
FIG. 23 is a schematic diagram illustrating an example of a configuration of an optical system of an ophthalmic apparatus according to a third embodiment.

FIG. 23 shows a block diagram of an example of the configuration of the ophthalmic apparatus 1b in FIG. 22. In FIG. 23, like reference numerals designate like parts as in FIG. 3 or FIG. 22. The same description may not be repeated.

In the perforated mirror PM, a hole, through which the illumination light or the returning light of the illumination light, is formed. The perforated mirror PM separates the optical path of the returning light of the illumination light from the subject's eye E from the optical path of the illumination light deflected by the scan optical system SC.

In some embodiments, the illumination light deflected by the scan optical system SC passes through the hole formed in the perforated mirror PM, and the returning light of the illumination light is reflected on the peripheral region of the hole to be guided to the splitter BS.

In some embodiments, the illumination light deflected by the scan optical system SC is reflected on the peripheral region of the hole to be guided to the objective lens OBJ, and the returning light of the illumination light passes through the hole to be guided to the splitter BS.

The splitter BS splits the returning light of the illumination light from the perforated mirror PM into the first returning light and the second returning light.

The first returning light split by the splitter BS is received by the detector DE1 (SLO detector DS). The second returning light split by the splitter BS is guided to the beam combiner BC.

In contrast, the reference light generated by the pattern illumination optical system PI1 also enters the splitter SP1. The reference light entering the splitter SP1 is reflected by the mirror Ma and is guided to the mirror RM. The mirror RM reflects the incident light in a direction opposite to the traveling direction of the incident light. The reference light reflected by the mirror RM is reflected by the mirror Mb to be guided to the beam combiner BC.

The beam combiner BC generates interference light between the second returning light split by the splitter BS and the reference light reflected by the mirror Mb. The interference light generated by the beam combiner BC is received by the detector DE1 (OCT detector DO).

The timing controller TC1 outputs the control signal Ctsc to the scan optical system SC, outputs the control signal Ctdet1 to the SLO detector DS, outputs the control signal Ctdet2 to the OCT detector DO, and outputs the control signal Ctls to the pattern illumination optical system PI1. As a result, the light receiving results are read out from the light receiving elements at the light receiving positions of the second returning light and the interference light corresponding to the irradiated positions of the illumination light, in synchronization with the movement timing of the irradiated positions of the illumination light on the subject's eye E.

Figure 24:
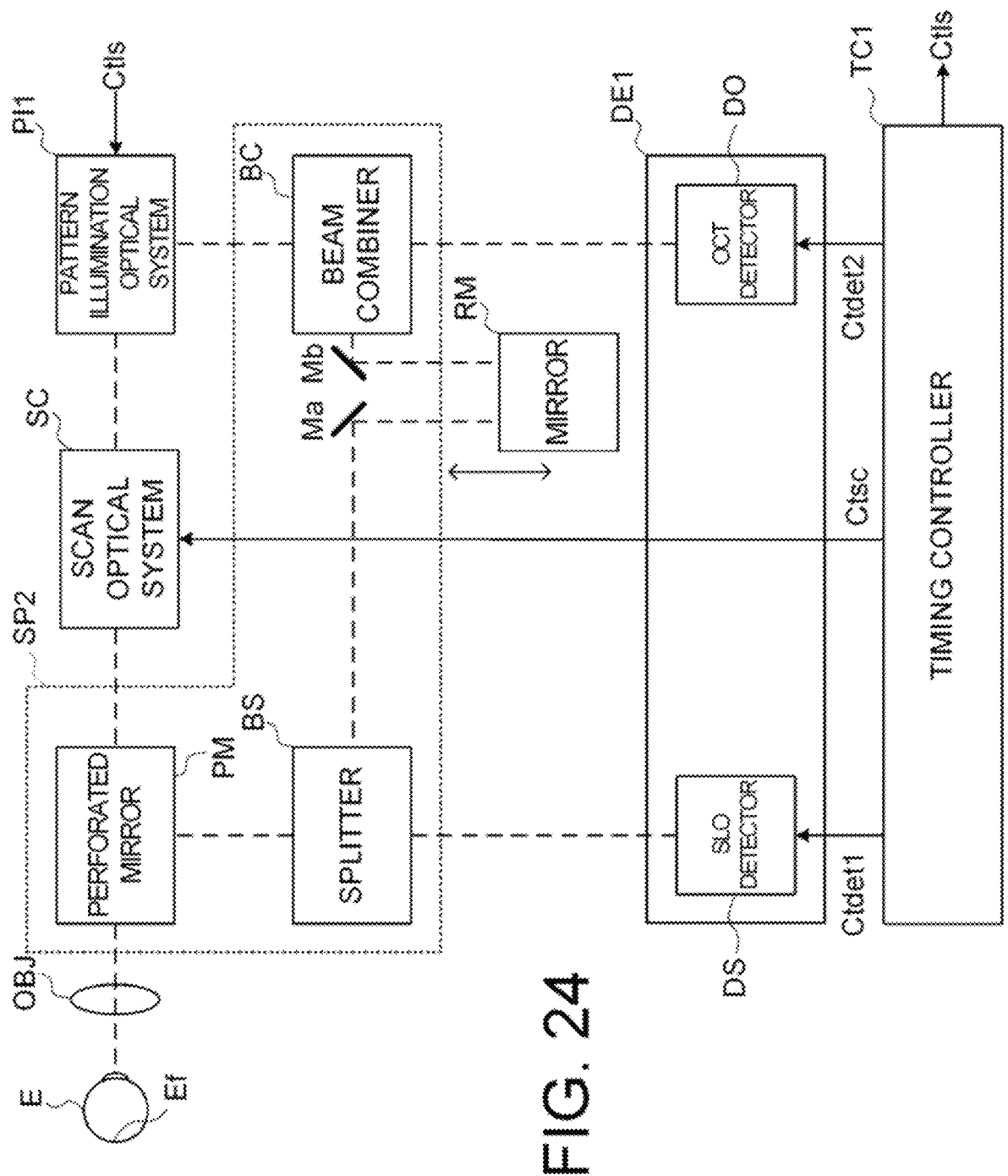
FIG. 24 is a schematic diagram illustrating an example of the configuration of the optical system of the ophthalmic apparatus according to the third embodiment.

FIG. 24 shows a block diagram of an another example of the configuration of the ophthalmic apparatus 1b in FIG. 22.

In FIG. 24, like reference numerals designate like parts as in FIG. 4 or FIG. 23. The same description may not be repeated.

The configuration of the ophthalmic apparatus 1b in FIG. 24 differs from the configuration of the ophthalmic apparatus 1b shown in FIG. 23 in the positions of the mirrors RM, Ma, and Mb, as in FIG. 4.

That is, in FIG. 24, the first returning light split by the splitter BS is guided to the detector DE1 (SLO detector DS), and the second returning light split by the splitter BS is guided to the mirror Ma. The second returning light is reflected by the mirror Ma, and then is guided to the mirror RM. The second returning light reflected by the mirror RM is reflected by the mirror Mb, and then is guided to the beam combiner BC.

The beam combiner BC generates the interference light between the reference light from the pattern illumination optical system PI1 and the second returning light reflected by the mirror Mb. The interference light generated by the beam combiner BC is guided to the detector DE1 (OCT detector DO).

In the ophthalmic apparatus 1b according to the third embodiment, the illumination light is generated using the wavelength swept light source, in the same manner as the first embodiment. In the following, a case where the mirror RM is arranged in the ophthalmic apparatus 1b as shown in FIG. 23 has been described. However, the mirror RM may be arranged in the ophthalmic apparatus 1, as shown in FIG. 24.

Figure 25:
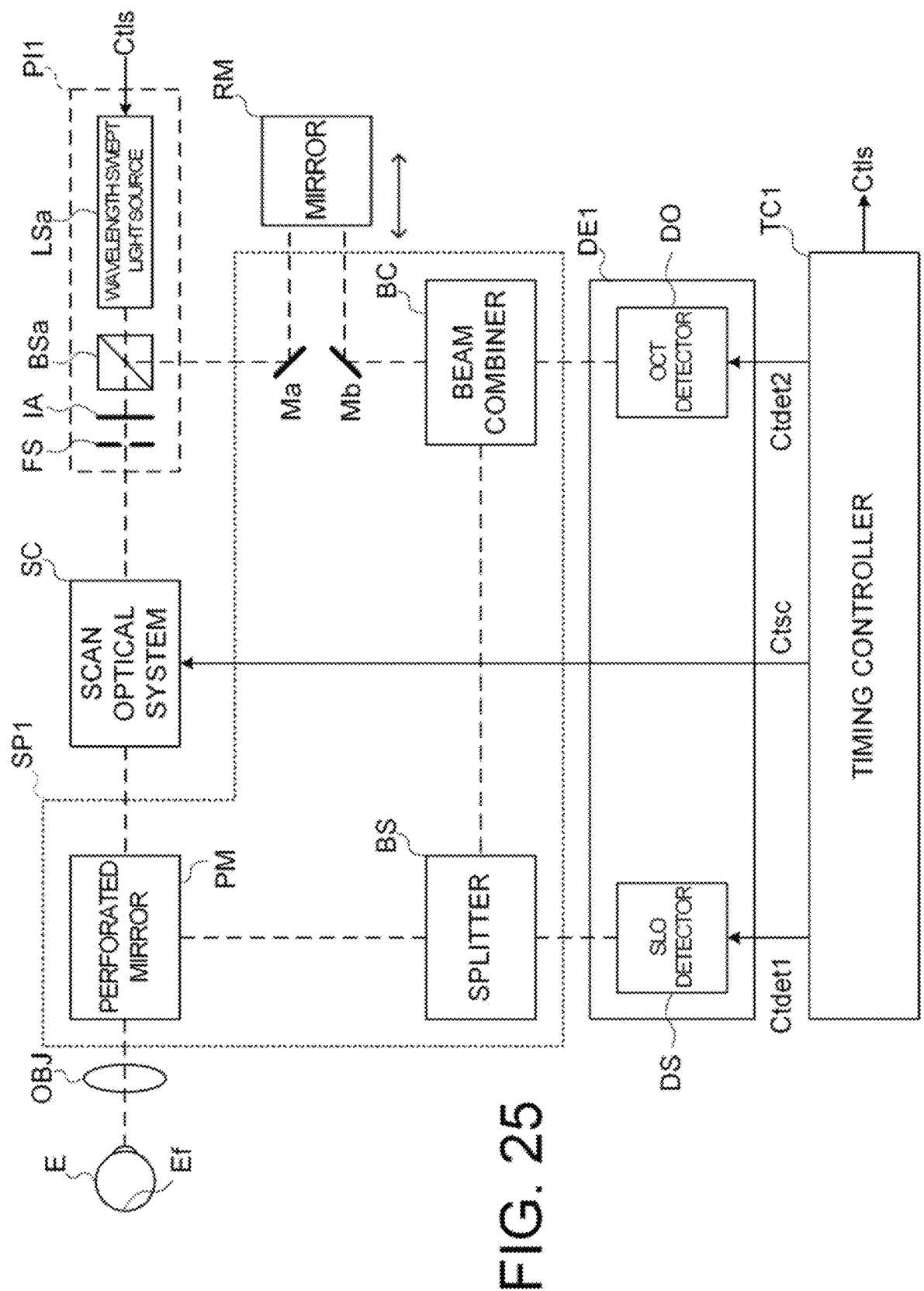
FIG. 25 is a schematic diagram illustrating an example of the configuration of the optical system of the ophthalmic apparatus according to the third embodiment.

FIG. 25 shows a block diagram of an example of the configuration of the ophthalmic apparatus 1b in FIG. 23. In FIG. 25, like reference numerals designate like parts as in FIG. 5 or FIG. 23. The same description may not be repeated.

As shown in FIG. 25, in the third embodiment, the optical system is configured with the wavelength swept light source, as in FIG. 5.

Hereinafter, a specific configuration example of the ophthalmic apparatus 1b according to the third embodiment will be described.

Figure 26:
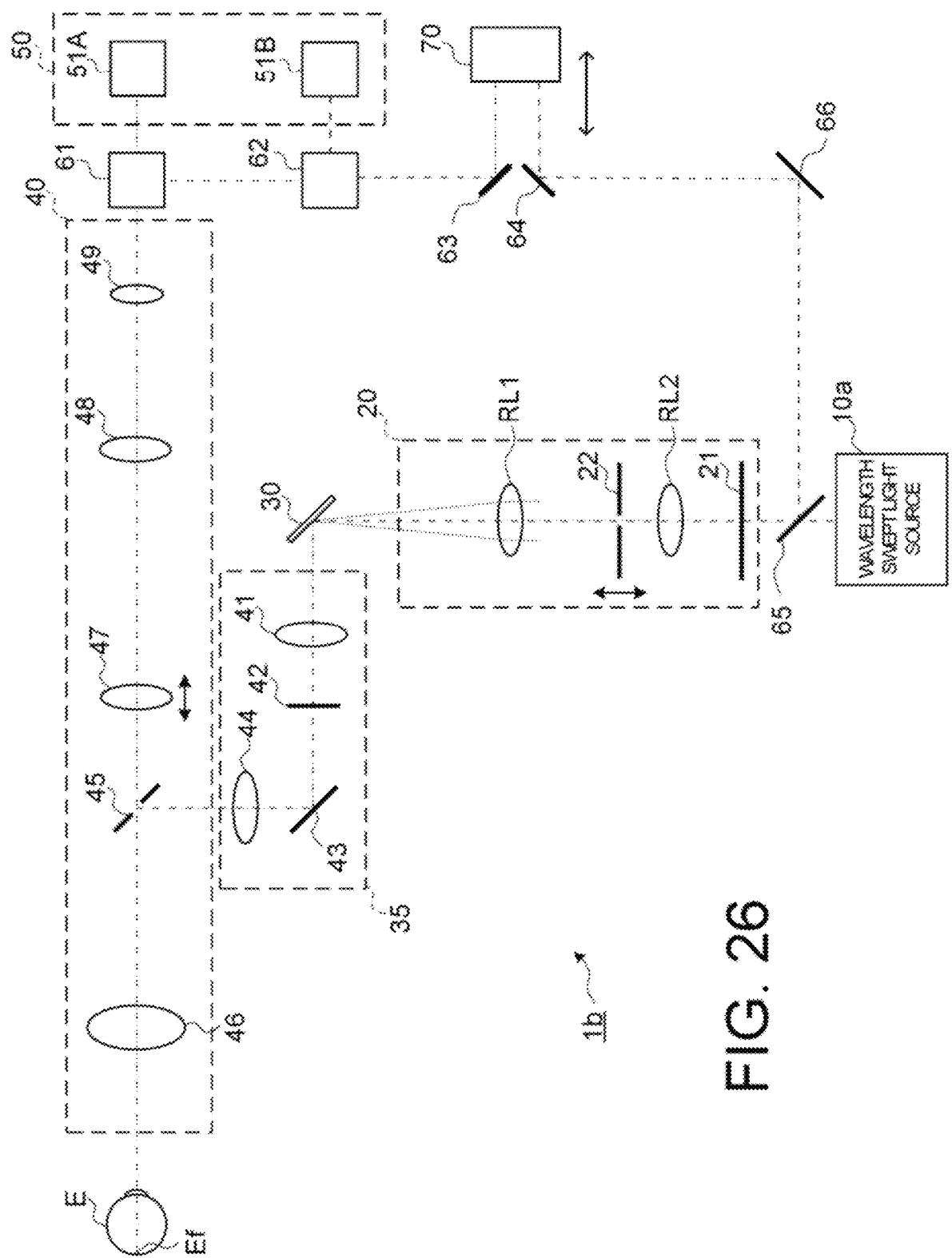
FIG. 26 is a diagram illustrating an example of the configuration of the optical system of the ophthalmic apparatus according to the third embodiment.

FIG. 26 shows an example of the configuration of an optical system of the ophthalmic apparatus 1b according to the third embodiment. In FIG. 26, like reference numerals designate like parts as in FIG. 6. The same description may not be repeated.

The configuration of the optical system shown in FIG. 26 is different from the configuration of the optical system shown in FIG. 6 in that the arrangement position of the optical scanner 30 and that the mirror 66 is arranged between the beam splitter 65 and the mirror 64. Specifically, the optical scanner 30 is arranged between the projection optical system 35 and the illumination optical system 20.

In the illumination optical system 20, the illumination light transmitted through the beam splitter 65 passes through the aperture(s) formed in the iris aperture 21, is transmitted through the relay lens system RL2, passed through the aperture(s) formed in the slit 22, and is transmitted through the relay lens system RL1. The light transmitted through the relay lens system RL1 is deflected by the optical scanner 30, and is guided to the projection optical system 35. Here, in the same way as in the first embodiment, a back focal position of the relay lens system RL1 is arranged at a position substantially conjugate optically to the iris of the subject's eye E. Thereby, the optical scanner 30 (deflected surface) is arranged at the back focal position of the relay lens system RL1 or the vicinity of the back focal position.

In the projection optical system 35, the illumination light deflected by the optical scanner 30 is transmitted through the relay lens 41, passes through the black point plate 42, is reflected by the reflective mirror 43, is transmitted through the relay lens 44, and is guided to the perforated mirror 45.

In the imaging optical system 40, the illumination light from the projection optical system 35 is reflected on the peripheral region formed in the perforated mirror 45 toward the objective lens 46. The illumination light reflected on the peripheral region of perforated mirror 45 is refracted by the objective lens 46, enters into the eye through the pupil of the subject's eye E, and illuminates the fundus Ef of the subject's eye E.

The returning light of the illumination light from the fundus Ef is refracted by the objective lens 46, passes through the hole of the perforated mirror 45, is transmitted through the focusing lens 47, is transmitted through the relay lens 48, passes through the imaging lens 49, is split into the first returning light and the second returning light by the beam splitter 61. The first returning light is received by the image sensor 51A in the imaging device 50. The second returning light is guided to the beam combiner 62. The beam combiner 62 generates the interference light between the second returning light and the reference light. The generated interference light is received by the image sensor 51B in the imaging device 50.

The operation of the ophthalmic apparatus 1b according to the third embodiment is the same as that of the first embodiment, and therefore the description is not repeated here.

As described above, according to the third embodiment, the same effects as in the first embodiment can be achieved.

Fourth Embodiment

The configuration according to the embodiments can be applied to an ophthalmic apparatus using other types of OCT (spectral domain type OCT or time domain OCT) other than the swept source type described in the third embodiment.

In the following, the fourth embodiment will be described with a focus on differences from the third embodiment.

Figure 27:
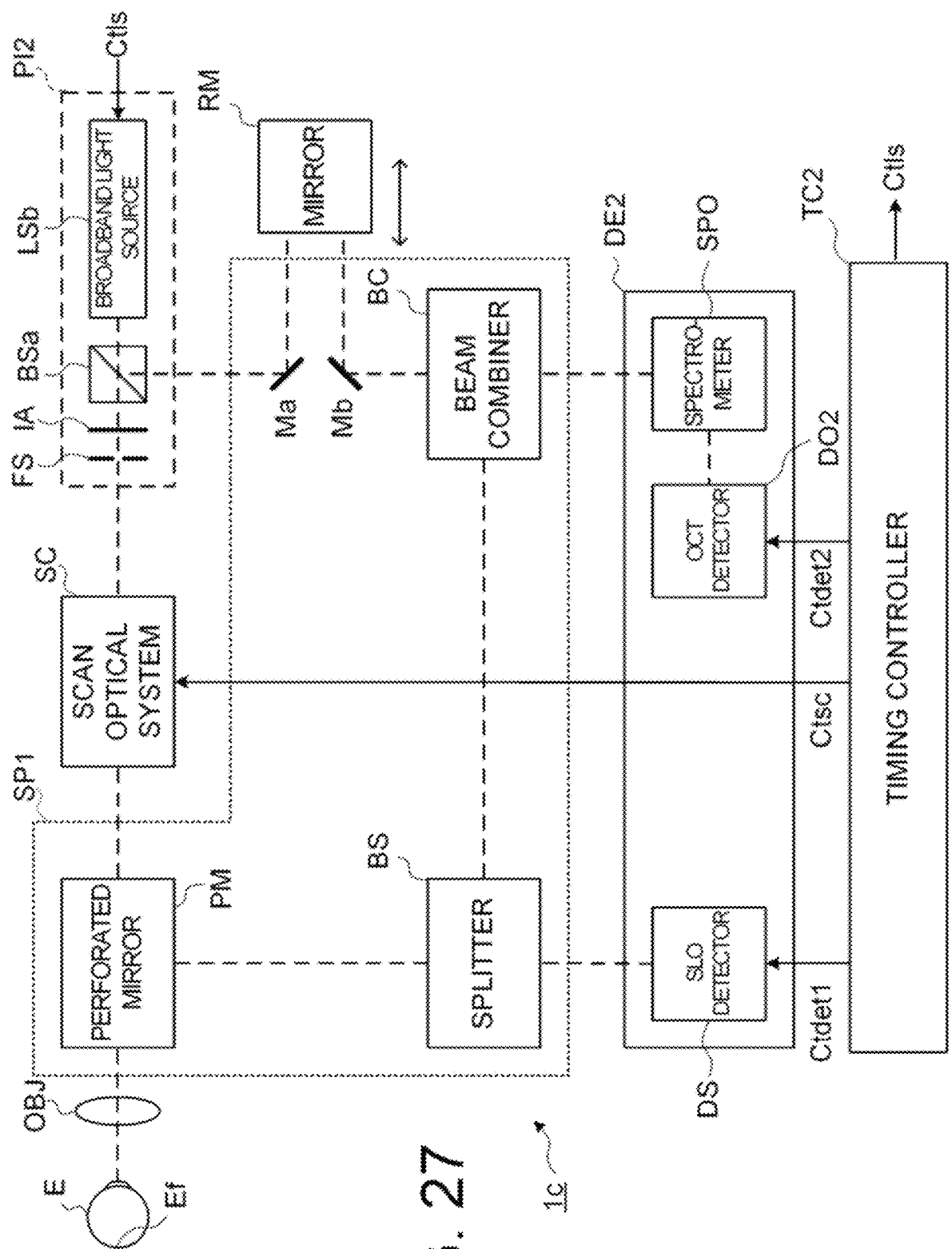
FIG. 27 is a schematic diagram illustrating an example of an configuration of an optical system of an ophthalmic apparatus according to a fourth embodiment.

FIG. 27 shows a block diagram of an example of a configuration of an ophthalmic apparatus according to the fourth embodiment. In FIG. 27, like reference numerals designate like parts as in FIG. 20 or FIG. 25. The same description may not be repeated.

The difference between the configuration of the ophthalmic apparatus 1c according to the fourth embodiment and the configuration of the ophthalmic apparatus 1b shown in FIG. 25 is mainly that a pattern illumination optical system PI2 is provided instead of the pattern illumination optical system PI1 that a detector DE2 is provided instead of the detector DE1, and that a timing controller TC2 is provided instead of the timing controller TC1.

The difference between the configuration of the pattern illumination optical system PI2 and the configuration of the pattern illumination optical system PI1 shown in FIG. 25 is that the broadband light source LSb is provided instead of the wavelength swept light source LSa.

The configuration of the detector DE2 differs from the configuration of the detector DE1 shown in FIG. 25 in that a spectrometer SPO and an OCT detector DO2 are provided instead of the OCT detector DO1.

The spectrometer SPO disperses the interference light generated by the beam combiner BC. For example, the spectrometer SPO decomposes the interference light into spectral components using a diffraction grating. The interference light decomposed into spectral components by the spectrometer SPO is received by the OCT detector DO2.

The timing controller TC2 controls each part to perform the known spectral domain type OCT.

In the fourth embodiment, a case where the configuration shown in FIG. 27, which changes the optical path length of the reference light, has been described as an example. However, the configuration of the fourth embodiment can be applied to the configuration shown in FIG. 4, which changes the optical path length of the illumination light.

According to the fourth embodiment, the same effects as in the first embodiment can be achieved.

Fifth Embodiment

The configuration of the ophthalmic apparatus according to the embodiments is not limited to the configurations described in the above embodiments. In the fifth embodiment, by performing light-shielding control for the reference light, a single detector can be used to detect the returning light of the illumination light from the subject's eye E and the interference light.

In the following, the fifth embodiment will be described with a focus on differences from the first embodiment.

Figure 28:
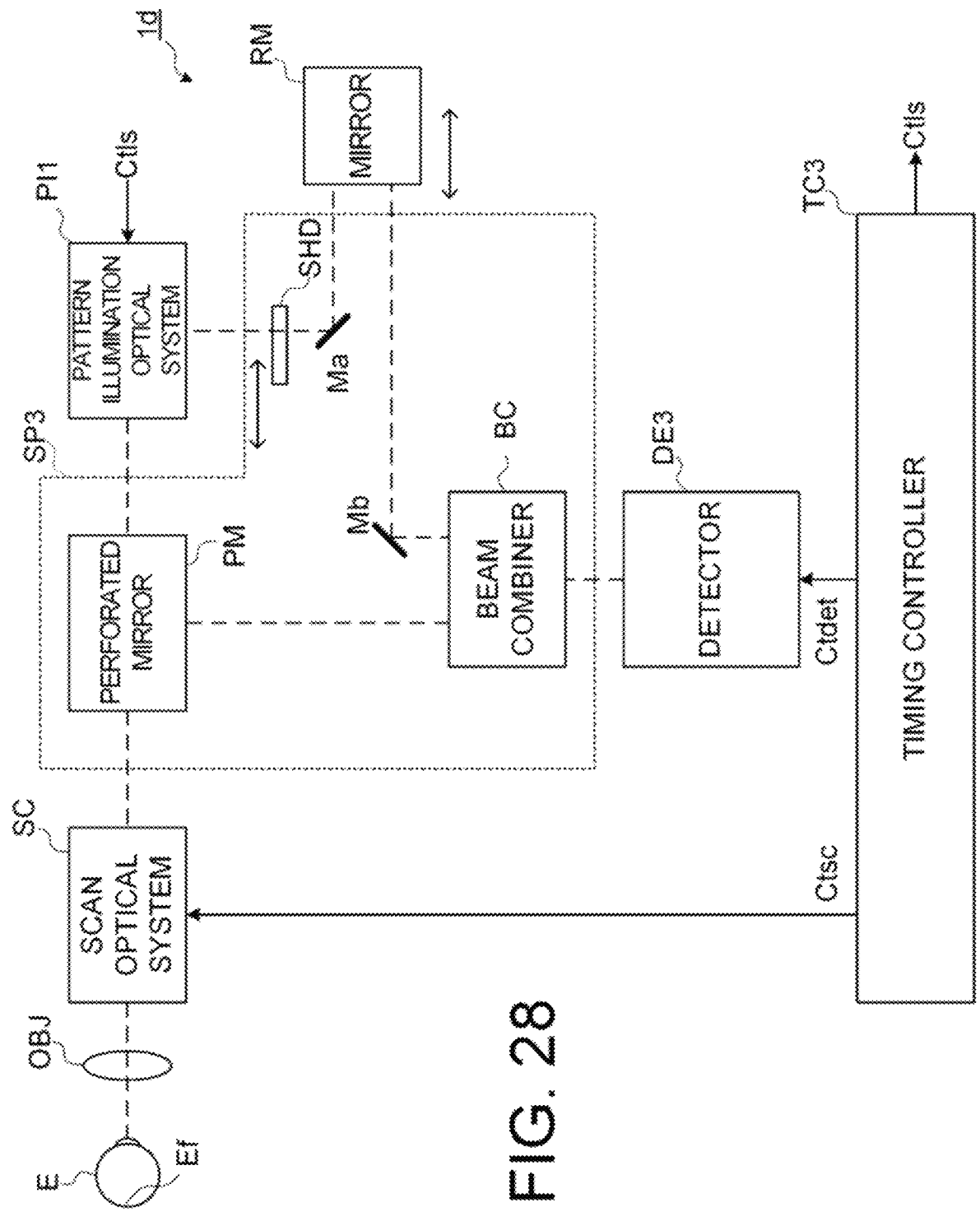
FIG. 28 is a schematic diagram illustrating an example of the configuration of an optical system of an ophthalmic apparatus according to a fifth embodiment.

FIG. 28 shows a block diagram of an example of a configuration of an ophthalmic apparatus according to the fifth embodiment. In FIG. 28, like reference numerals designate like parts as in FIG. 3. The same description may not be repeated.

The difference between the configuration of the ophthalmic apparatus 1d according to the fifth embodiment and the configuration of the ophthalmic apparatus 1 shown in FIG. 3 is mainly that a splitter SP3 is provided instead of splitter SP1, that a detector DE3 is provided instead of the detector DE1, and that a timing controller TC3 is provided instead of the timing controller TC1.

The splitter SP3 includes the perforated mirror PM, the beam combiner BC, the mirrors Ma and Mb, and a light-shielding plate SHD.

The perforated mirror PM separates the optical path of the returning light of the illumination light from the subject's eye E from the optical path of the illumination light generated by the pattern illumination optical system PI1. The hole formed in the perforated mirror PM is arranged at a position conjugate optically to the iris of the subject's eye E.

In some embodiments, the illumination light from the pattern illumination optical system PI1 passes through the hole formed in the perforated mirror PM, and the returning light of the illumination light is reflected on the peripheral region of the hole to be guided to the beam combiner BC.

In some embodiments, the illumination light from the pattern illumination optical system PI1 is reflected on the peripheral region of the hole to be guided to the scan optical system SC, and the returning light of the illumination light passes through the hole to be guided to the beam combiner BC.

The reference light generated by the pattern illumination optical system PI1 also enters the splitter SP3. The reference light entering the splitter SP3 is reflected by the mirror Ma and is guided to the mirror RM. The mirror RM reflects the incident light in a direction opposite to the traveling direction of the incident light. The reference light reflected by the mirror RM is reflected by the mirror Mb to be guided to the beam combiner BC.

The light-shielding plate SHD is provided so as to be capable of being inserted into and removed from the optical path of the reference light. In FIG. 28, the light-shielding plate SHD is provided so as to be capable of being inserted into and removed from the optical path of the reference light between the pattern illumination optical system PI1 and the mirror Ma. The light-shielding plate SHD shields the reference light when the light-shielding plate SHD is placed in the optical path of the reference light. The function of the light-shielding plate SHD may be realized by a mirror that deflects the reference light so that it does not reach the mirror Ma.

The beam combiner BC generates the interference light between the returning light of the illumination light from the perforated mirror PM and the reference light reflected by the mirror Mb. The interference light generated by the beam combiner BC is received by the detector DE3. The detector DE3 may be a detector used in the known OCT.

As a result, when the light-shielding plate SHD is arranged in the optical path of the reference light, the returning light alone enters the beam combiner BC. Thereby, the beam combiner BC guides the returning light of the illumination light from the subject's eye E to the detector DE3. Further, when the light-shielding plate SHD is removed from the optical path of the reference light, the beam combiner BC generates the interference light between the returning light and the reference light, and guides the generated interference light to the detector DE3.

The timing controller TC3 outputs the control signal Ctsc to the scan optical system SC, outputs the control signal Ctdet to the detector DE3, outputs the control signal Ctls to the pattern illumination optical system PI1. As a result, the light receiving results are read out from the light receiving elements at the light receiving positions of the returning light and the interference light corresponding to the irradiated positions of the illumination light, in synchronization with the movement timing of the irradiated positions of the illumination light on the subject's eye E.

Figure 29:
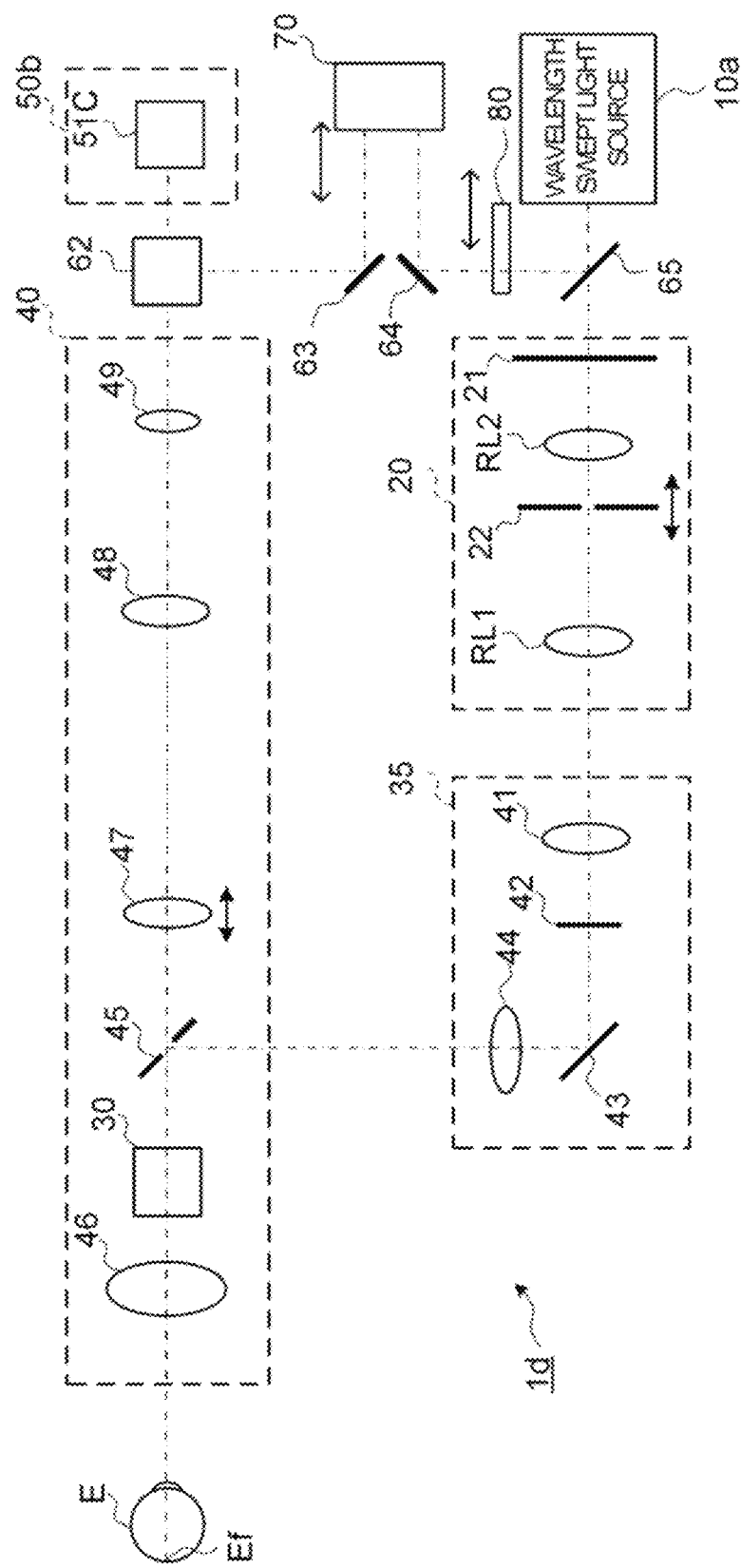
FIG. 29 is a diagram illustrating an example of the configuration of the optical system of the ophthalmic apparatus according to the fifth embodiment.

FIG. 29 shows an example of the configuration of an optical system of the ophthalmic apparatus 1d according to the fifth embodiment. In FIG. 29, like reference numerals designate like parts as in FIG. 6. The same description may not be repeated.

The configuration of the optical system shown in FIG. 29 is different from the configuration of the optical system shown in FIG. 6 in the light-shielding plate 80 and the imaging device 50b.

The light-shielding plate 80 can be inserted into or removed from the optical path of the reference light split by the beam splitter 65 using a known movement mechanism.

The imaging device 50b includes an image sensor 51C. The image sensor 51C may include one or more balanced photodiodes arranged in a one-dimensional or two-dimensional manner, in the same way as in the image sensor 51B.

Figure 30:
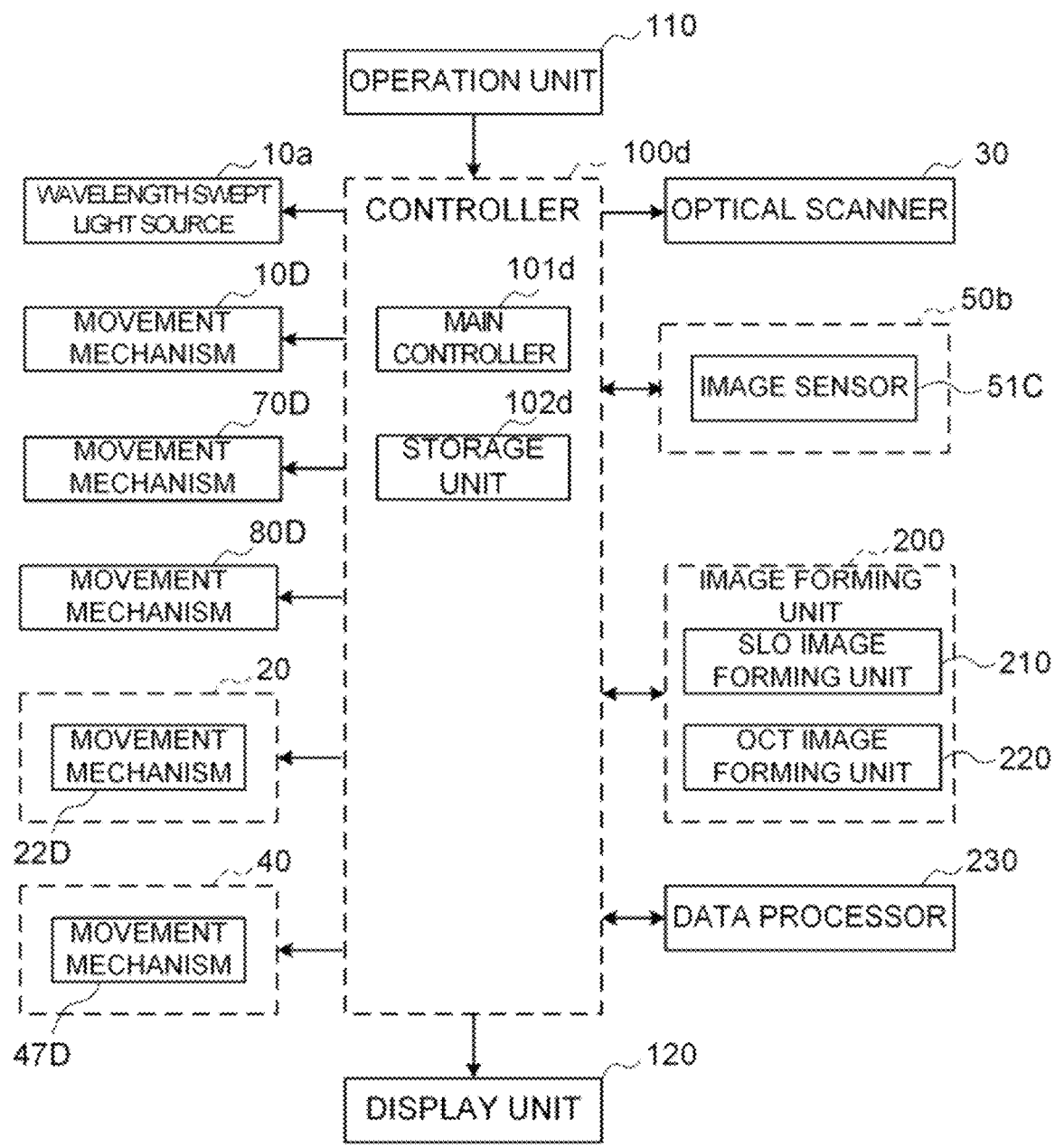
FIG. 30 is a schematic diagram illustrating an example of a configuration of a control system of the ophthalmic apparatus according to the fifth embodiment.

FIG. 30 shows a block diagram of an example of the configuration of a control system of the ophthalmic apparatus 1d according to the fifth embodiment. In FIG. 30, like reference numerals designate like parts as in FIG. 14. The same description may not be repeated.

As shown in FIG. 30, the control system of the ophthalmic apparatus 1d is configured with a controller 100d as a center. It should be noted at least part of the configuration of the control system may be included in the optical system in the ophthalmic apparatus 1d.

(Controller 100d)

The controller 100d controls each part of the ophthalmic apparatus 1d. The controller 100d includes a main controller 101d and a storage unit 102d. The controller 100d realizes the functions of the timing controller TC3. The main controller 101d includes a processor and executes the control processing of each part of the ophthalmic apparatus 1*d* by executing processing according to the program(s) stored in the storage unit 102*d*.

(Main Controller 101*d*)

The main controller 101*d* performs control for the wavelength swept light source 10*a*, the movement mechanisms 10D, 70D, and 80D, control for the illumination optical system 20, control for the optical scanner 30, control for the imaging optical system 40, control for the imaging device 50*b*, control for the image forming unit 200, and control for the data processor 230.

The configuration of the control system shown in FIG. 30 is different from the configuration of the control system shown in FIG. 14 in that the control is performed for the movement mechanism 80D, and that the control is performed for the imaging device 50*b* instead of the imaging device 50.

The movement mechanism 80D moves the light-shielding plate 80 so as to be inserted into and removed from the optical path of the reference light using a known mechanism, under control from the controller 100*d*. In some embodiments, the movement mechanism 80D moves the light-shielding plate 80 in a direction intersecting the optical path of the reference light. In some embodiments, the movement mechanism 80D rotates a turret plate around a rotary axis substantially parallel to the optical path of the reference light. In the turret plate, holes are formed on its circumference around the rotary axis.

Examples of the control for the imaging device 50*b* include a control for the image sensor 51C (rolling shutter control). Examples of the control for the image sensor 51C include the reset control, the exposure control, the charge transfer control, and the output control. Further, time Tr required for the reset control, time (exposure time) Te required for the exposure control, time Tc required for the charge transfer control, and time Tout required for the output control, etc., can be changed.

Next, the operation of the ophthalmic apparatus 1*d* will be described.

Figure 31:
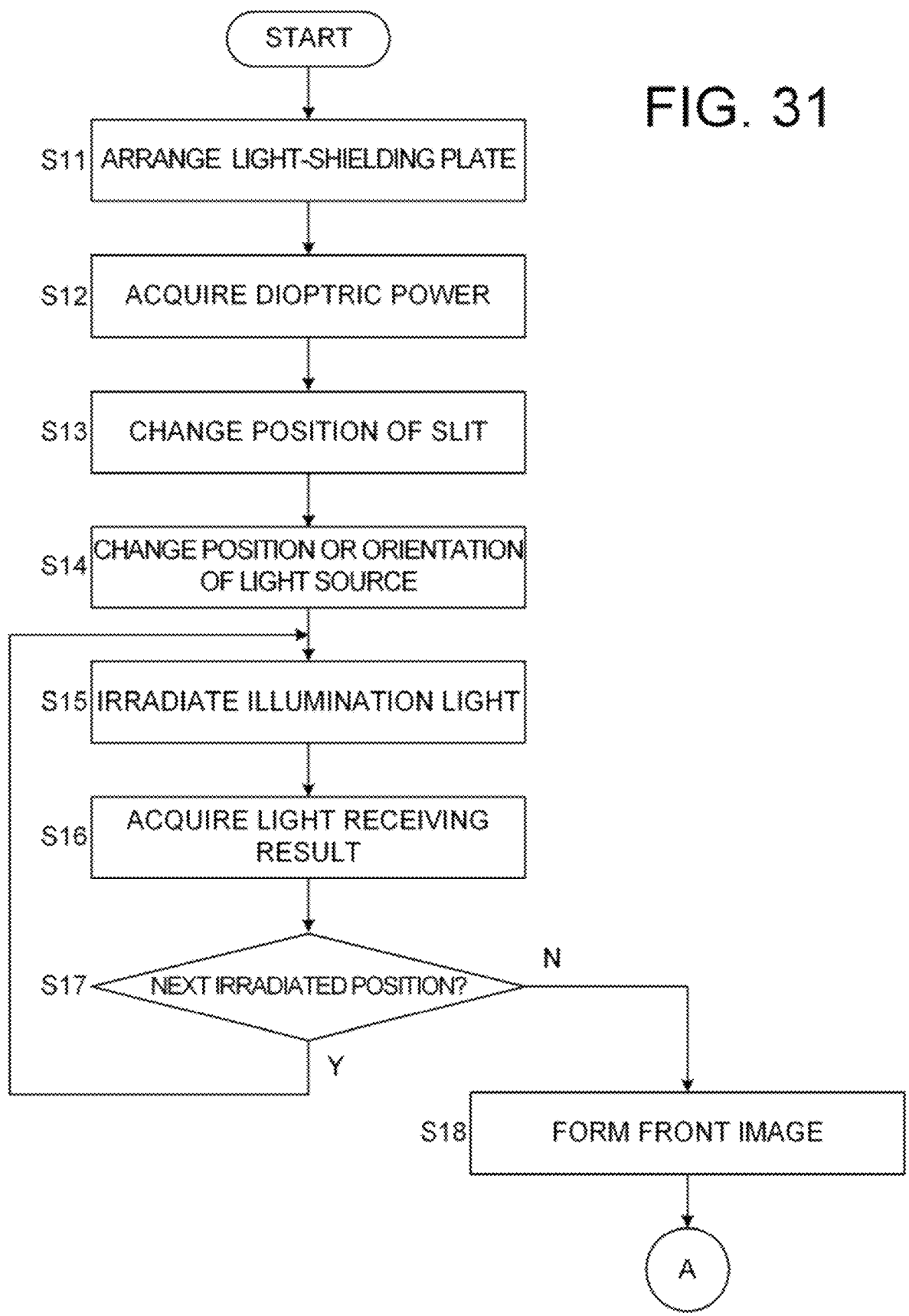
FIG. 31 is a flowchart illustrating an example of an operation of the ophthalmic apparatus according to the fifth embodiment.
Figure 32:
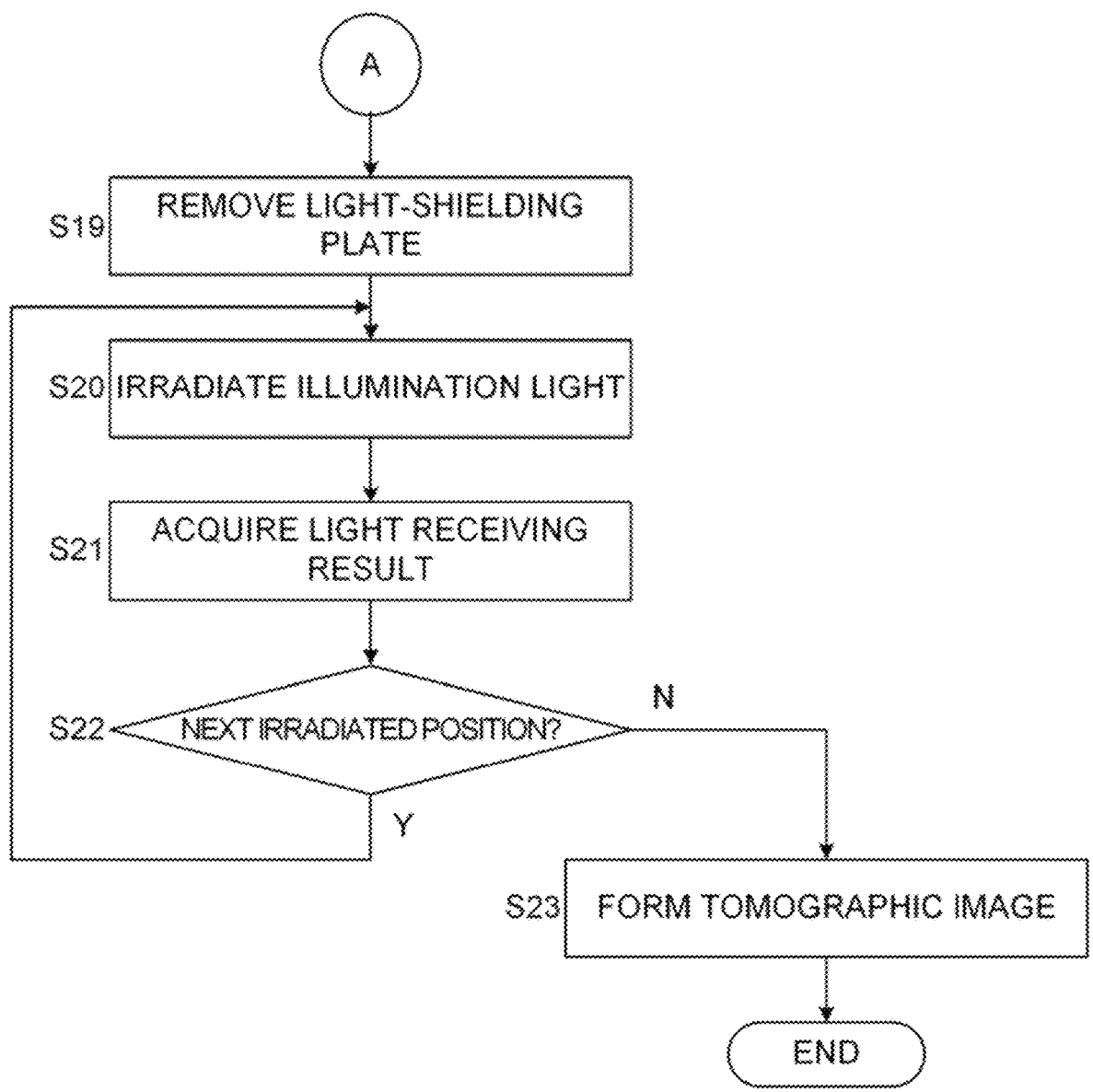
FIG. 32 is a flowchart illustrating an example of an operation of the ophthalmic apparatus according to the fifth embodiment.

FIGS. 31 to 32 show flowcharts of examples of the operation of the ophthalmic apparatus 1*d* according to the fifth embodiment. The storage unit 102*d* stores computer programs for realizing the processing shown in FIG. 31 and FIG. 32. The main controller 101*d* operates according to the computer programs, and thereby the main controller 101*d* performs the processing shown in FIG. 31 and FIG. 32.

Here, it is assumed that the alignment of the optical system of the apparatus with respect the subject's eye E using the alignment system (not shown) is completed, and that the fixation target is projected onto the fundus of the subject's eye E to guide the subject's eye E to a desired fixation position using the fixation projection system, in the same way as in FIG. 18.

(S11: Arrange Light-Shielding Plate)

First, the main controller 101*d* controls the movement mechanism 80D to arrange the light-shielding plate 80 in the optical path of the reference light.

(S12: Acquire Dioptric Power)

Next, the main controller 101*d* acquires the dioptric power of the subject's eye E from an external ophthalmic measurement apparatus or an electronic medical record, in the same way as in step S1.

(S13: Change Position of Slit)

Subsequently, the main controller 101*d* changes the position of the slit 22 on the optical axis of the illumination optical system 20 in accordance with the dioptric power of the subject's eye E acquired in step S12, in the same way as in step S2.

Specifically, the main controller 101*d* specifies the position of the slit 22 corresponding to the dioptric power by referring to the first control information stored in the storage unit 102*d*, and controls the movement mechanism 22D so as to arrange the slit 22 at the specified position.

(S14: Change Position or Orientation of Light Source)

Subsequently, the main controller 101*d* changes at least one of the position of the wavelength swept light source 10*a* and the orientation of the wavelength swept light source 10*a* in accordance with the new position of the slit 22 whose position on the optical axis has been changed in step S13, in the same way as in step S3.

Specifically, the main controller 101*d* specifies at least one of the position and the orientation of the wavelength swept light source 10*a* corresponding to the dioptric power or the position of the slit 22 after movement, by referring to the second control information stored in the storage unit 102*d*. And then, the main controller 101*d* controls the movement mechanism 10D so that the wavelength swept light source 10*a* is arranged at the specified position or in the specified orientation.

(S15: Irradiate Illumination Light)

Next, the main controller 101*d* controls the illumination optical system 20 to generate the slit-shaped illumination light, and to start the deflection control of the optical scanner 30 to start irradiating the illumination light onto the desired irradiated region on the fundus Ef, in the same way as in step S4. When the irradiation of the illumination light is started, the slit-shaped illumination light is sequentially irradiated within the desired irradiated range as described above.

(S16: Acquire Light Receiving Result)

The main controller 101*d* acquires the light receiving results of the pixels in the opening range of the image sensor 51C corresponding to the irradiated range of the illumination light on the fundus Ef performed in step S15, in the same way as in step S5. In step S16, the light receiving results of the returning light of the illumination light irradiated on the subject's eye E are acquired.

(S17: Next Irradiated Position?)

The main controller 101*d* determines whether or not the next irradiated position is to be irradiated with the illumination light, in the same way as in step S6. The main controller 101*d* can determine whether or not the next irradiated position is to be irradiated with the illumination light, by determining whether or not the irradiated range of the illumination light that is moved sequentially has covered a predetermined imaging range of the fundus Ef.

When it is determined that the next irradiated position is to be irradiated with the illumination light (S17: Y), the operation of the ophthalmic apparatus 1*d* proceeds to step S15. When it is determined that the next irradiated position is not to be irradiated with the illumination light (S17: N), the operation of the ophthalmic apparatus 1*d* proceeds to step S18.

(S18: Form Front Image)

In step S17, when it is determined that the next irradiated position is not to be irradiated with the illumination light (S17: N), the main controller 101*d* controls the image forming unit 200 to form the image of the subject's eye E from the light receiving results acquired repeatedly while changing the irradiated range of the illumination light in step S16.

Specifically, the image forming unit 200 forms the front image. In this case, the SLO image forming unit 210 syntheses a plurality of light receiving results with different irradiated ranges (opening range on the light receiving surface of the image sensor 51C) of the illumination light for the number of times repeating the process in step S15 to S17, based on the order of the movement of the irradiated range. Thereby, the fundus image of the fundus Ef for one frame is formed.

(S19: Remove Light-Shielding Plate)

Subsequently, the main controller 101d controls the movement mechanism 80D to remove the light-shielding plate 80 from the optical path of the reference light.

(S20: Irradiate Illumination Light)

Next, the main controller 101d controls the illumination optical system 20 to generate the slit-shaped illumination light, and to start the deflection control of the optical scanner 30 to start irradiating the illumination light onto the desired irradiated region on the fundus Ef, in the same way as in step S15. When the irradiation of the illumination light is started, the slit-shaped illumination light is sequentially irradiated within the desired irradiated range as described above.

(S21: Acquire Light Receiving Result)

The main controller 101d acquires the light receiving results of the pixels in the opening range of the image sensor 51C corresponding to the irradiated range of the illumination light on the fundus Ef performed in step S20, in the same way as in step S16. In step S21, the light receiving results of the returning light of the illumination light and the reference light irradiated on the subject's eye E are acquired.

(S22: Next Irradiated Position?)

The main controller 101d determines whether or not the next irradiated position is to be irradiated with the illumination light, in the same way as in step S17.

When it is determined that the next irradiated position is to be irradiated with the illumination light (S22: Y), the operation of the ophthalmic apparatus 1d proceeds to step S20. When it is determined that the next irradiated position is not to be irradiated with the illumination light (S22: N), the operation of the ophthalmic apparatus 1d proceeds to step S23.

(S23: Form Front Image)

In step S22, when it is determined that the next irradiated position is not to be irradiated with the illumination light (S22: N), the main controller 101d controls the image forming unit 200 to form the image of the subject's eye E from the light receiving results acquired repeatedly while changing the irradiated range of the illumination light in step S21.

Specifically, the image forming unit 200 forms the tomographic image. In this case, the OCT image forming unit 220 syntheses a plurality of light receiving results with different irradiated ranges (opening range on the light receiving surface of the image sensor 51C) of the illumination light for the number of times repeating the process in step S20 to S22, based on the order of the movement of the irradiated range. Thereby, the tomographic image of the fundus Ef is formed.

This terminates the operation of the ophthalmic apparatus 1d (END).

As described above, according to the fifth embodiment, the front image and the tomographic image of the subject's eye E are formed based on the returning light of the illumination light and the interference light, while sharing the light source, the scan optical system, and the detector (in particular, the image sensor). This allows to observe the subject's eye in detail with a simple configuration.

Further, the light source and the like for acquiring the front image and the tomographic image are shared. This allows to perform position matching between the acquired front image and the acquired tomographic image of the subject's eye E with high accuracy. As a result, the site of interest of the subject's eye E can be observed in detail.

Further, at least the scan optical system and the detector are synchronized using the rolling shutter method. This allows to acquire high quality images with a simple configuration.

Sixth Embodiment

The configuration according to the embodiments can be applied to an ophthalmic apparatus using other types of OCT (spectral domain type OCT or time domain OCT) other than the swept source type described in the fifth embodiment.

In the following, the sixth embodiment will be described with a focus on differences from the fifth embodiment.

Figure 33:
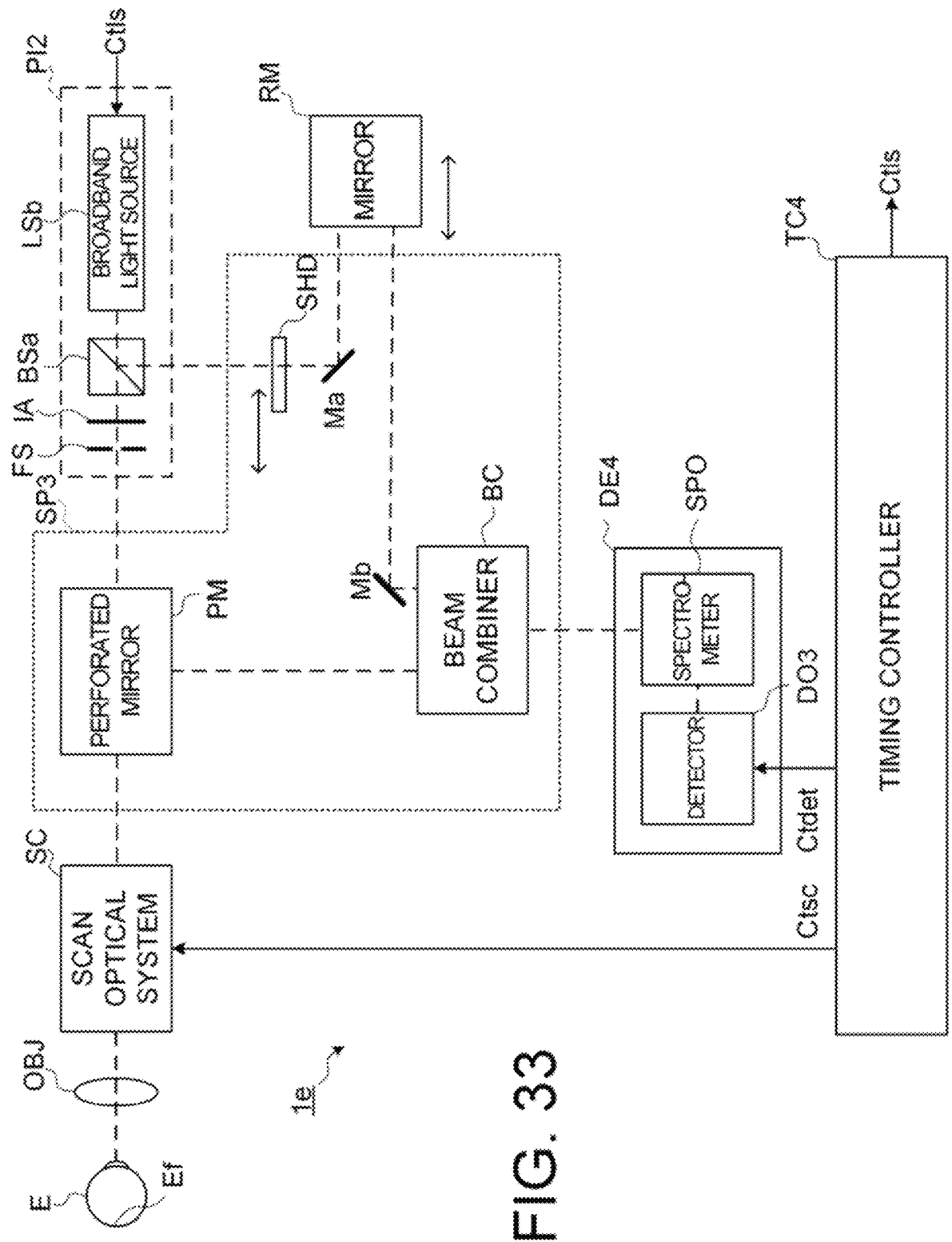
FIG. 33 is a schematic diagram illustrating an example of a configuration of an optical system of an ophthalmic apparatus according to a sixth embodiment.

FIG. 33 shows a block diagram of an example of a configuration of an ophthalmic apparatus 1e according to the sixth embodiment. In FIG. 33, like reference numerals designate like parts as in FIG. 20 or FIG. 28. The same description may not be repeated.

The difference between the configuration of the ophthalmic apparatus 1e according to the sixth embodiment and the configuration of the ophthalmic apparatus 1d shown in FIG. 28 is mainly that a pattern illumination optical system PI2 is provided instead of the pattern illumination optical system PI1, that a detector DE4 is provided instead of the detector DE3, and that a timing controller TC4 is provided instead of the timing controller TC3.

The configuration of the detector DE4 differs from the configuration of the detector DE3 shown in FIG. 28 in that a spectrometer SPO and an OCT detector DO3 are provided.

The spectrometer SPO disperses the interference light or the returning light of the illumination light from the beam combiner BC. For example, the spectrometer SPO decomposes the returning light or the interference light into spectral components using a diffraction grating. The interference light decomposed into spectral components by the spectrometer SPO is received by the detector DO3.

The timing controller TC4 controls each part to perform the known spectral domain type OCT.

Hereinafter, a specific configuration example of the ophthalmic apparatus 1e according to the sixth embodiment will be described.

Figure 34:
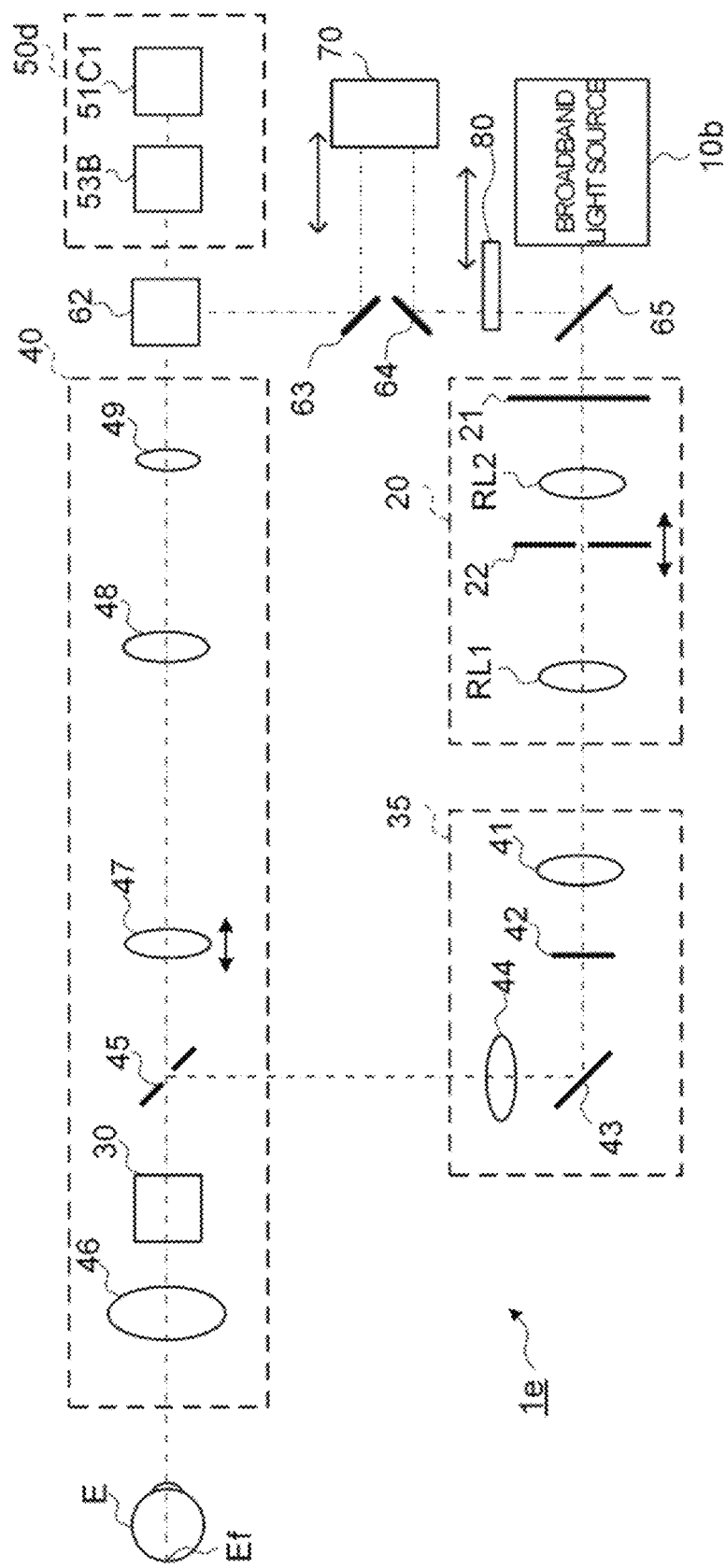
FIG. 34 is a diagram illustrating an example of the configuration of the optical system of the ophthalmic apparatus according to the sixth embodiment.

FIG. 34 shows an example of the configuration of an optical system of the ophthalmic apparatus 1e according to the sixth embodiment. In FIG. 34, like reference numerals designate like parts as in FIG. 29 or FIG. 33. The description will be given as appropriate.

In FIG. 34, the broadband light source 10b is provided instead of the wavelength swept light source 10a in FIG. 29. Further, an imaging device 50d is provided instead of the imaging device 50b in FIG. 29. The imaging device 50d includes the spectrometer 53B and an image sensor 51C1.

In other words, the broadband light source 10b corresponds to the broadband light source LSb in FIG. 29. The spectrometer 53B corresponds to the spectrometer SPO in FIG. 33. The image sensor 51C corresponds to the detector DO3 in FIG. 33.

When the light-shielding plate 80 is arranged in the optical path of the reference light, the beam combiner 62 directly guides the returning light of the illumination light from the imaging optical system 40 to the imaging device 50d. In contrast, when the light-shielding plate 80 is removed from the optical path of the reference light, the beam combiner 62 generates the interference light between the reference light from the mirror 63 and the returning light of the illumination light from the imaging optical system 40, and guides the generated interference light to the imaging device 50d.

The spectrometer 53B decomposes the returning light of the illumination light from the beam combiner BC or the interference light into spectral components using the diffraction grating. The image sensor 51C1 receives the interference light decomposed into the spectral components by the spectrometer 53B. The image sensor 51C1 is, for example, a line sensor, and detects the spectral components of the interference light to generate an electric signal (that is, a detection signal).

For example, the SLO image forming unit 210 re-composes the spectral components decomposed by the spectrometer 53B for the light receiving results obtained by the image sensor 51C1, and forms the SLO image based on the re-composed results. For example, the OCT image forming unit 220 performs Fourier transform processing, etc. on the light receiving results obtained by the image sensor 51C1, and forms the OCT image by making a picture.

In the sixth embodiment, a case where the configuration shown in FIG. 34, which changes the optical path length of the reference light, has been described as an example. However, the configuration of the sixth embodiment can be applied to the configuration shown in FIG. 4, which changes the optical path length of the illumination light.

According to the sixth embodiment, the same effects as in the fifth embodiment can be achieved.

Seventh Embodiment

In the fifth embodiment or the sixth embodiment, a case where the illumination light is irradiated onto the subject's eye E by deflecting the illumination light incident through the splitter SP has been described. However, the configuration according to the embodiments is not limited thereto. In a seventh embodiment, the illumination light deflected by the scan optical system SC is irradiated onto the subject's eye E through the splitter SP, in the same way as in the third embodiment.

In the following, the seventh embodiment will be described with a focus on differences from the fifth embodiment.

Figure 35:
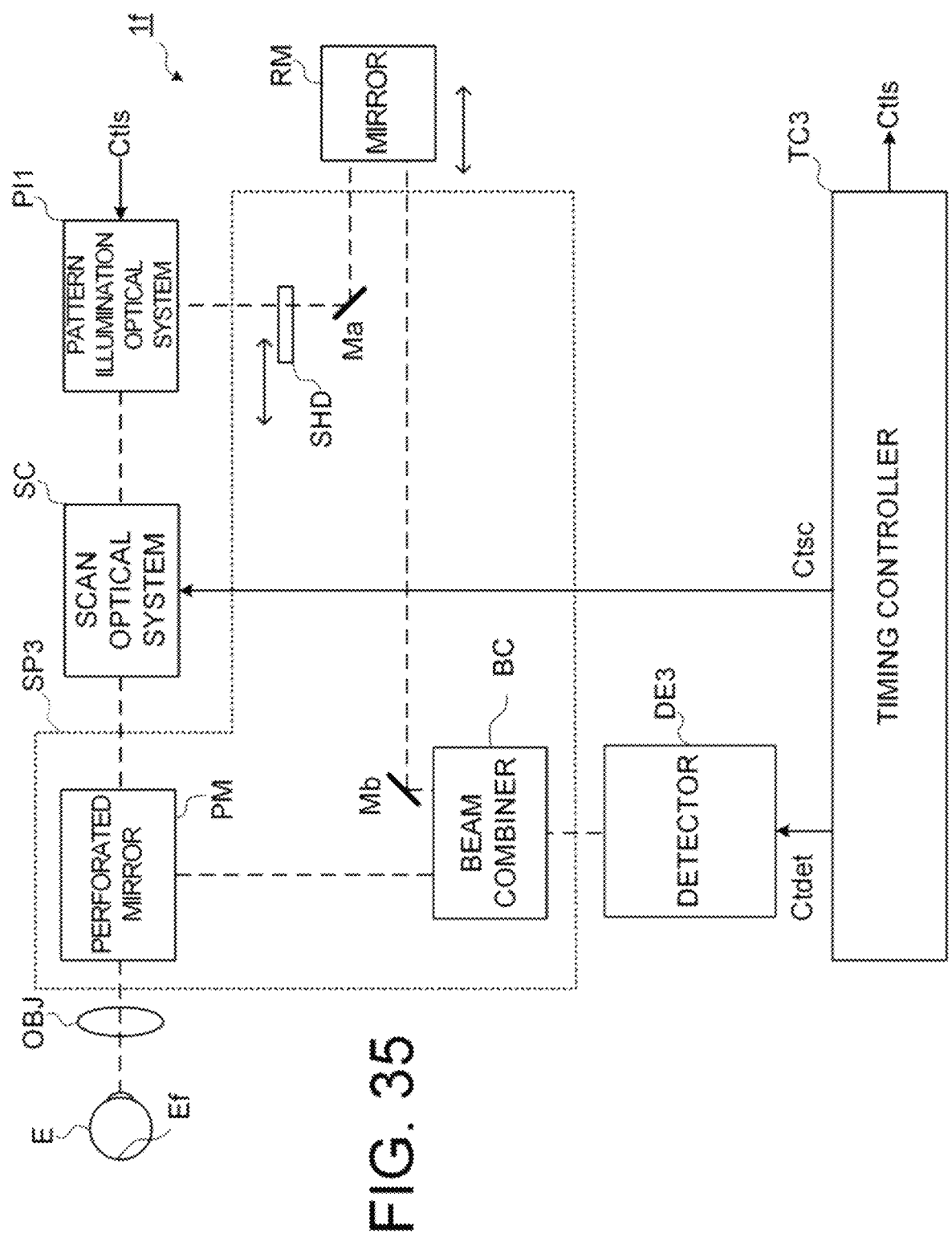
FIG. 35 is a schematic diagram illustrating an example of an configuration of an optical system of an ophthalmic apparatus according to a seventh embodiment.

FIG. 35 shows a block diagram of an example of a configuration of an ophthalmic apparatus if according to the seventh embodiment. In FIG. 35, like reference numerals designate like parts as in FIG. 28. The same description may not be repeated.

The configuration of the ophthalmic apparatus if according to the seventh embodiment differs from the configuration of the ophthalmic apparatus 1d shown in FIG. 28 in the arrangement of the scan optical system SC and the splitter SP3. That is, in the ophthalmic apparatus 1f, the illumination light generated by the pattern illumination optical system PI1 is deflected by the scan optical system SC, and the deflected illumination light is split into light guided to be objective lens OBJ and light guided to the mirror RM by the splitter SP3.

In the perforated mirror PM, a hole is formed. The illumination light or the returning light of the illumination light passes through this hole. The perforated mirror PM separates the optical path of the returning light of the illumination light from the subject's eye E from the optical path of the illumination light deflected by the scan optical system SC.

In some embodiments, the illumination light deflected by the scan optical system SC passes through the hole formed in the perforated mirror PM, and the returning light of the illumination light is reflected on the peripheral region of the hole to be guided to the beam combiner BC.

In some embodiments, the illumination light deflected by the scan optical system SC is reflected on the peripheral region of the hole to be guided to the objective lens OBJ, and the returning light of the illumination light passes through the hole to be guided to the beam combiner BC.

The beam combiner BC generates the interference light between the returning light of the illumination light from the perforated mirror PM and the reference light reflected by the mirror Mb. The interference light generated by the beam combiner BC is received by the detector DE3.

As a result, when the light-shielding plate SHD is arranged in the optical path of the reference light, the returning light alone enters the beam combiner BC. Thereby, the beam combiner BC guides the returning light of the illumination light from the subject's eye E to the detector DE3. Further, when the light-shielding plate SHD is removed from the optical path of the reference light, the beam combiner BC generates the interference light between the returning light and the reference light, and guides the generated interference light to the detector DE3.

The timing controller TC3 outputs the control signal Ctsc to the scan optical system SC, outputs the control signal Ctdet to the detector DE3, outputs the control signal Ctls to the pattern illumination optical system PI1. As a result, the light receiving results are read out from the light receiving elements at the light receiving positions of the returning light and the interference light corresponding to the irradiated positions of the illumination light, in synchronization with the movement timing of the irradiated positions of the illumination light on the subject's eye E.

Hereinafter, a specific configuration example of the ophthalmic apparatus if according to the seventh embodiment will be described.

Figure 36:
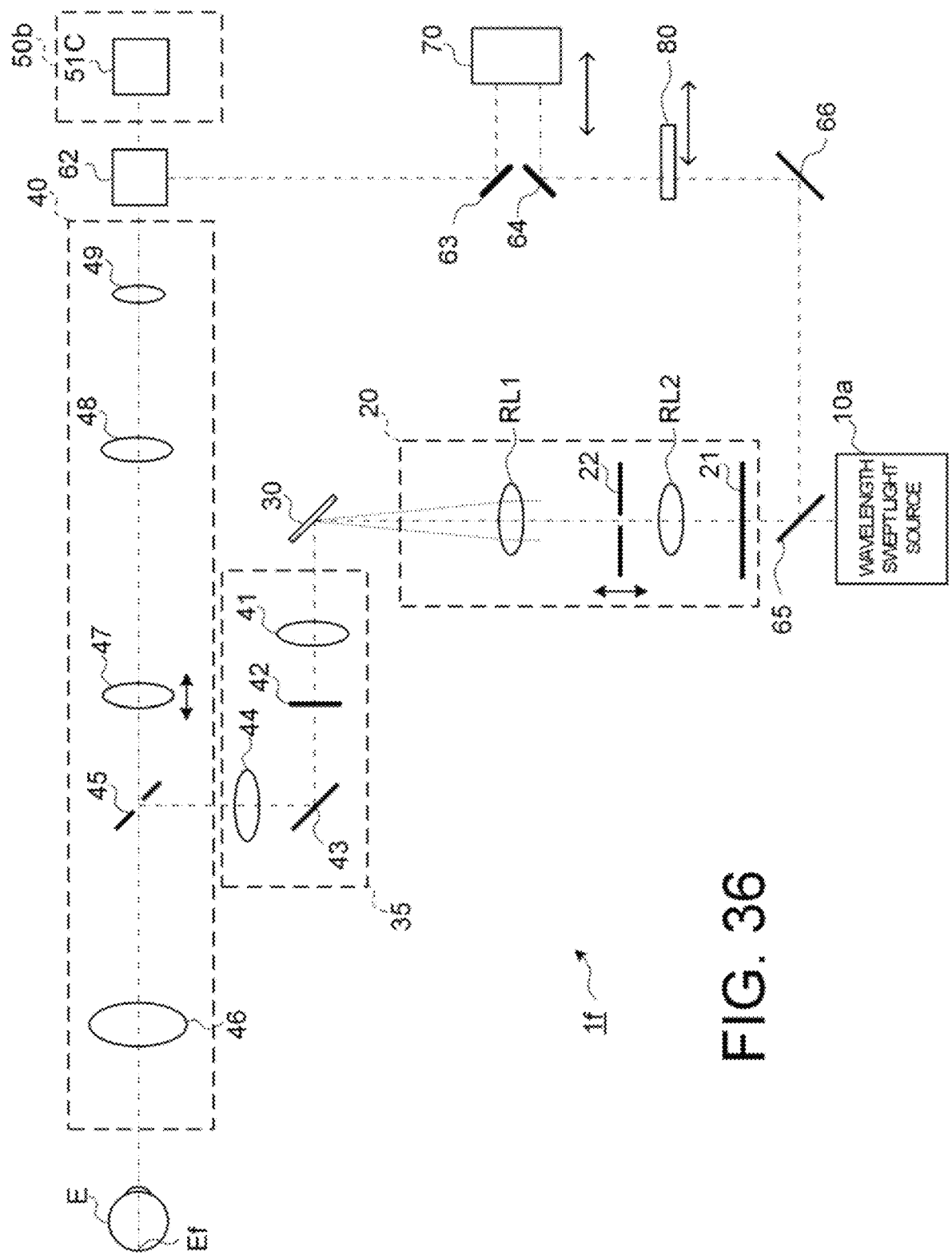
FIG. 36 is a diagram illustrating an example of the configuration of the optical system of the ophthalmic apparatus according to the seventh embodiment.

FIG. 36 shows an example of the configuration of an optical system of the ophthalmic apparatus if according to the seventh embodiment. In FIG. 36, like reference numerals designate like parts as in FIG. 34 or FIG. 35. The description will be given as appropriate.

The configuration of the optical system shown in FIG. 36 is different from the configuration of the optical system shown in FIG. 34 in that the arrangement position of the optical scanner 30 and that the mirror 66 is arranged between the beam splitter 65 and the mirror 64. Specifically, the optical scanner 30 is arranged between the projection optical system 35 and the illumination optical system 20.

In the illumination optical system 20, the illumination light transmitted through the beam splitter 65 passes through the aperture(s) formed in the iris aperture 21, is transmitted through the relay lens system RL2, passed through the aperture(s) formed in the slit 22, and is transmitted through the relay lens system RL1. The light transmitted through the relay lens system RL1 is deflected by the optical scanner 30, and is guided to the projection optical system 35. Here, in the same way as in the first embodiment, a back focal position of the relay lens system RL1 is arranged at a position substantially conjugate optically to the iris of the subject's eye E. Thereby, the optical scanner 30 (deflected surface) is arranged at the back focal position of the relay lens system RL1 or the vicinity of the back focal position.

In the projection optical system 35, the illumination light deflected by the optical scanner 30 is transmitted through the relay lens 41, passes through the black point plate 42, is reflected by the reflective mirror 43, passes through the relay lens 44, and is guided to the perforated mirror 45.

In the imaging optical system 40, the illumination light from the projection optical system 35 is reflected on the peripheral region formed in the perforated mirror 45 toward the objective lens 46. The illumination light reflected on the peripheral region of perforated mirror 45 is refracted by the objective lens 46, enters into the eye through the pupil of the subject's eye E, and illuminates the fundus Ef of the subject's eye E.

The returning light of the illumination light from the fundus Ef is refracted by the objective lens 46, passes through the hole of the perforated mirror 45, is transmitted through the focusing lens 47, is transmitted through the relay lens 48, passes through the imaging lens 49, and is received by the image sensor 51C in the imaging device 50b via the beam combiner 62.

When the light-shielding plate 80 is arranged in the optical path of the reference light between the beam splitter 65 and the mirror 64, the beam combiner 62 guides the reference light of the illumination light to the image sensor 51C. When the light-shielding plate is removed from the optical path of the reference light between the beam splitter 65 and the mirror 64, the beam combiner 62 generates the interference light between the returning light of the illumination light and the reference light, and guides the generated interference light to the image sensor 51C.

The operation of the ophthalmic apparatus 1f according to the seventh embodiment is the same as that of the fifth embodiment, and therefore the description is not repeated here.

As described above, according to the seventh embodiment, the same effects as in the fifth embodiment can be achieved.

Eighth Embodiment

The configuration according to the embodiments can be applied to an ophthalmic apparatus using other types of OCT (spectral domain type OCT or time domain OCT) other than the swept source type described in the seventh embodiment.

In the following, the eighth embodiment will be described with a focus on differences from the seventh embodiment.

Figure 37:
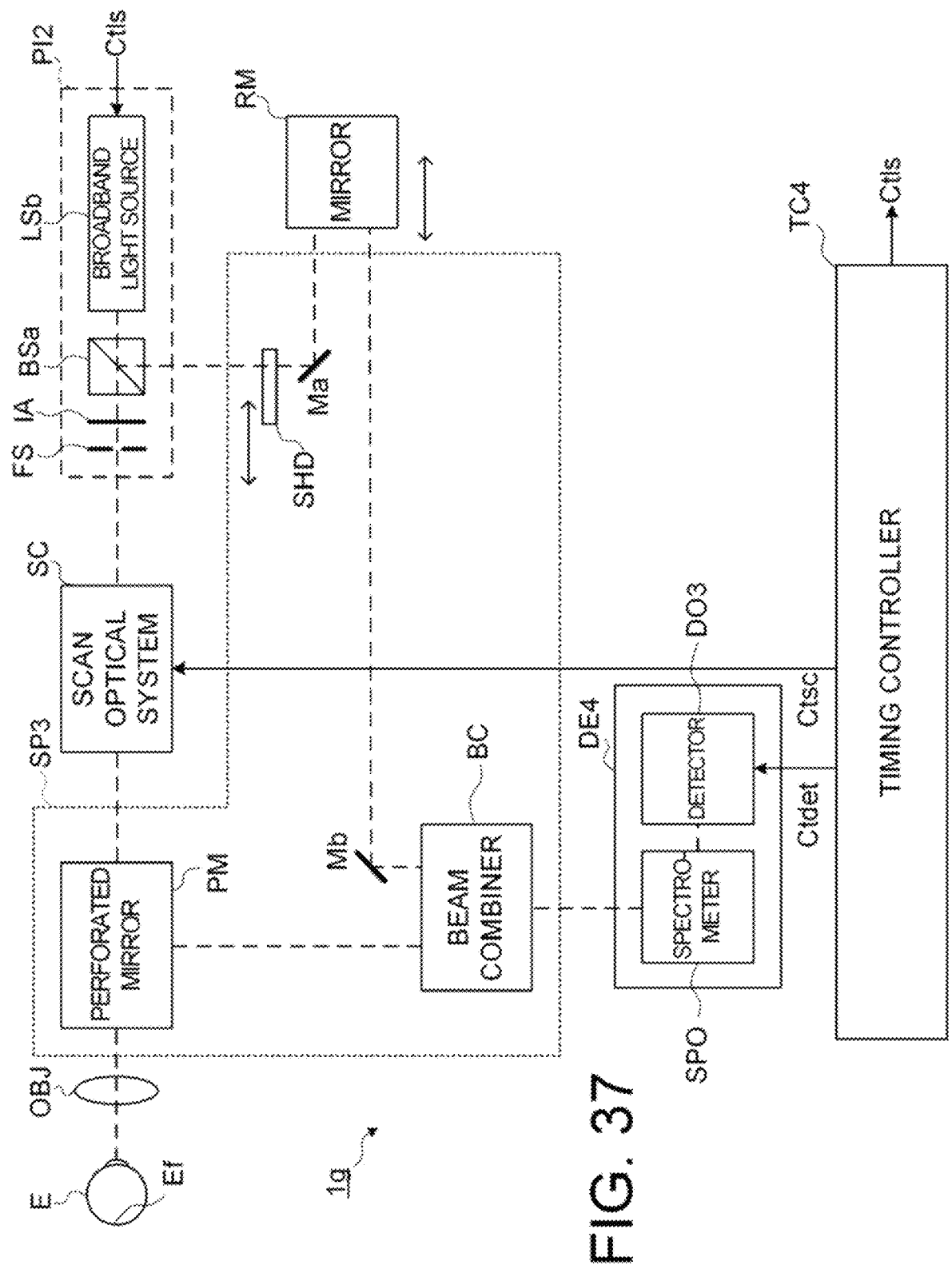
FIG. 37 is a schematic diagram illustrating an example of an configuration of an optical system of an ophthalmic apparatus according to an eighth embodiment.

FIG. 37 shows a block diagram of an example of a configuration of an ophthalmic apparatus 1g according to the eighth embodiment. In FIG. 37, like reference numerals designate like parts as in FIG. 33 or FIG. 35. The same description may not be repeated.

The difference between the configuration of the ophthalmic apparatus 1g according to the eighth embodiment and the configuration of the ophthalmic apparatus 1f shown in FIG. 35 is mainly that the pattern illumination optical system PI2 is provided instead of the pattern illumination optical system PI1, that the detector DE4 is provided instead of the detector DE3, and that the timing controller TC4 is provided instead of the timing controller TC3.

The configuration of the detector DE4 differs from the configuration of the detector DE3 shown in FIG. 35 in that a spectrometer SPO and a detector DO3 are provided.

The spectrometer SPO disperses the interference light or the returning light of the illumination light from the beam combiner BC. For example, the spectrometer SPO decomposes the returning light or the interference light into spectral components using a diffraction grating. The interference light decomposed into spectral components by the spectrometer SPO is received by the detector DO3.

The timing controller TC4 controls each part to perform the known spectral domain type OCT.

Hereinafter, a specific configuration example of the ophthalmic apparatus 1g according to the eighth embodiment will be described.

Figure 38:
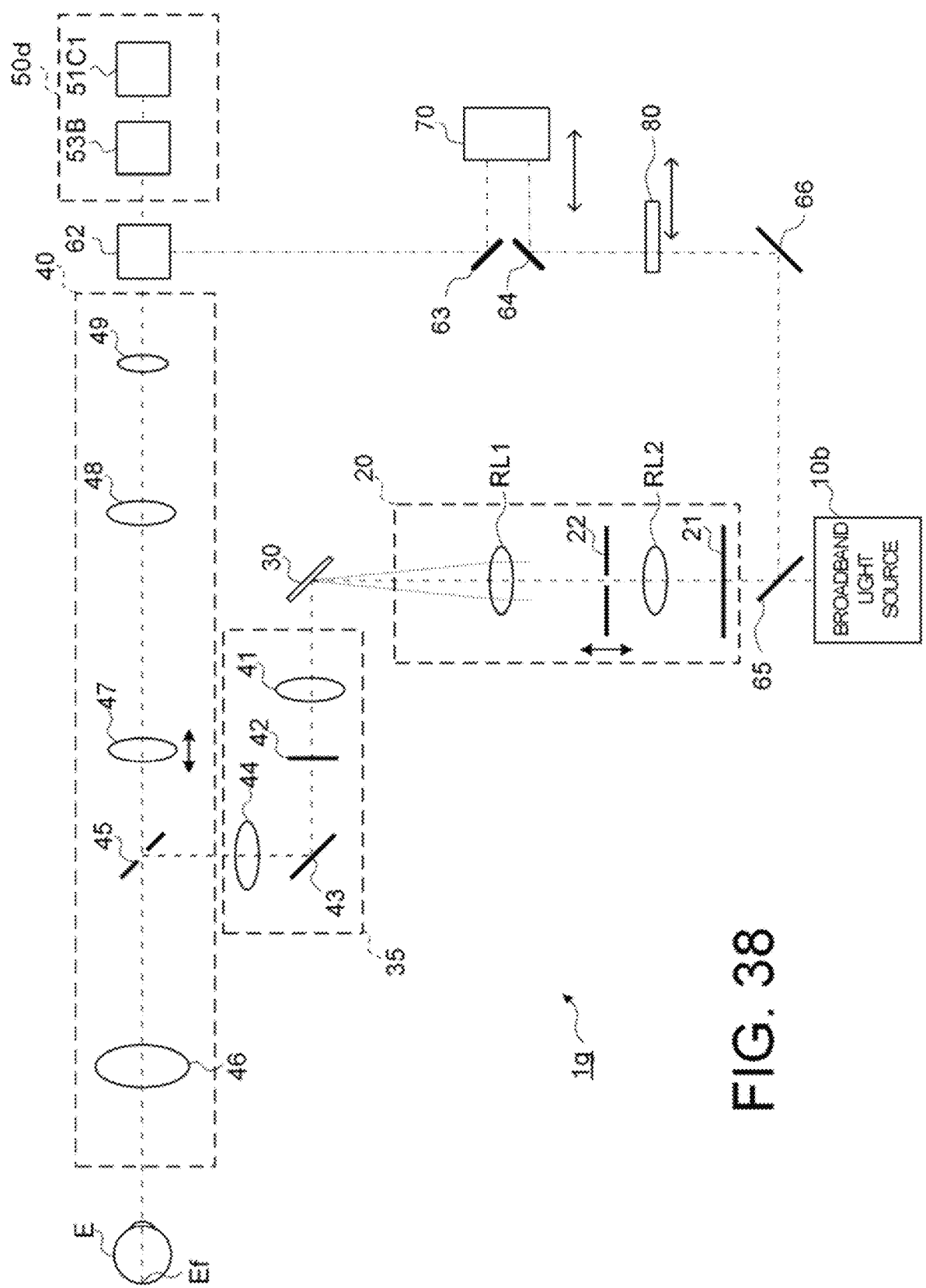
FIG. 38 is a diagram illustrating an example of the configuration of the optical system of the ophthalmic apparatus according to the eighth embodiment.

FIG. 38 shows an example of the configuration of an optical system of the ophthalmic apparatus 1g according to the eighth embodiment. In FIG. 38, like reference numerals designate like parts as in FIG. 36 or FIG. 37. The description will be given as appropriate.

In FIG. 38, the broadband light source 10b is provided instead of the wavelength swept light source 10a in FIG. 36. Further, the imaging device 50d is provided instead of the imaging device 50b in FIG. 36. The imaging device 50d includes the spectrometer 53B and the image sensor 51C1.

In other words, the broadband light source 10b corresponds to the broadband light source LSb in FIG. 37. The spectrometer 53B corresponds to the spectrometer SPO in FIG. 37. The image sensor 51C1 corresponds to the detector DO3 in FIG. 37.

When the light-shielding plate 80 is arranged in the optical path of the reference light, the beam combiner 62 directly guides the returning light of the illumination light from the imaging optical system 40 to the imaging device 50d. In contrast, when the light-shielding plate 80 is removed from the optical path of the reference light, the beam combiner 62 generates the interference light between the reference light from the mirror 63 and the returning light of the illumination light from the imaging optical system 40, and guides the generated interference light to the imaging device 50d.

The spectrometer 53B decomposes the returning light of the illumination light from the beam combiner 62 or the interference light into spectral components using the diffraction grating. The image sensor 51C1 receives the interference light decomposed into the spectral components by the spectrometer 53B. The image sensor 51C1 is, for example, a line sensor, and detects the spectral components of the interference light to generate an electric signal (that is, a detection signal).

In the eighth embodiment, a case where the configuration shown in FIG. 38, which changes the optical path length of the reference light, has been described as an example. However, the configuration of the eighth embodiment can be applied to the configuration shown in FIG. 4, which changes the optical path length of the illumination light.

According to the eighth embodiment, the same effects as in the seventh embodiment can be achieved.

Ninth Embodiment

The configuration of the ophthalmic apparatus according to the embodiments is not limited to the configurations described in the above embodiments or the modification example thereof.

In the following, the ninth embodiment will be described with a focus on differences from the first embodiment.

Figure 39:
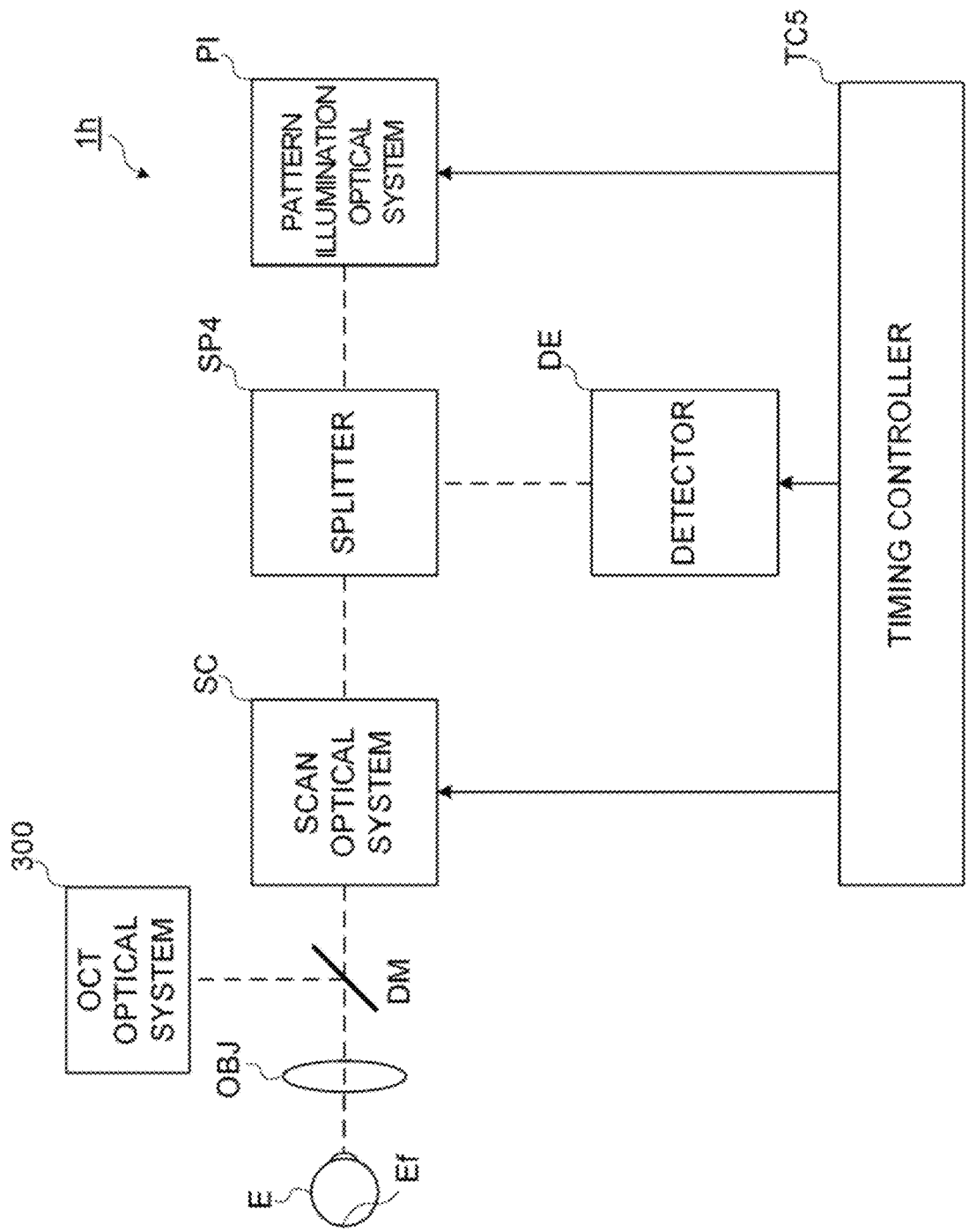
FIG. 39 is a schematic diagram illustrating an example of an configuration of an optical system of an ophthalmic apparatus according to a ninth embodiment.

FIG. 39 shows a block diagram of an example of a configuration of an ophthalmic apparatus according to the ninth embodiment. In FIG. 39, like reference numerals designate like parts as in FIG. 1. The same description may not be repeated.

The difference between the configuration of the ophthalmic apparatus 1h according to the ninth embodiment and the configuration of the ophthalmic apparatus 1 shown in FIG. 1 is mainly that the splitter SP4 is provided instead of splitter SP, that an OCT optical system 300 and a dichroic mirror DM are provided, and that a timing controller TC5 is provided instead of the timing controller TC.

The splitter SP4 transmits through the illumination light from the pattern illumination optical system PI to guide the illumination light to the scan optical system SC, and reflects the returning light of the illumination light from the scan optical system SC toward the detector DE.

The dichroic mirror DM is arranged between the scan optical system SC and the objective lens OBJ. The dichroic mirror DM transmits the illumination light from the scan optical system SC to guide the illumination light to the objective lens OBJ, and guides the returning light of the illumination light from the objective lens OBJ to the scan optical system SC. The dichroic mirror DM reflects the measurement light from the OCT optical system 300 to guide the measurement light to the objective lens OBJ, and reflects the returning light of the measurement light from the objective lens OBJ to guide the returning light to the OCT optical system 300.

The OCT optical system 300 splits light from a light source into measurement light and reference light, guides the measurement light to the dichroic mirror DM, and detects interference light between returning light of the measurement light and the reference light. The OCT optical system 300 includes an optical system for performing a known swept source type OCT, or an optical system for performing a known spectral domain type OCT.

According to the ninth embodiment, for example, by using the rolling shutter method, without being affected by unnecessary scattered light, high quality images of the fundus Ef with strong contrast can be acquired using a simple configuration. Furthermore, OCT can also be performed in an ophthalmic apparatus capable of acquiring such high quality images.

Tenth Embodiment

In the first embodiment to the eighth embodiment, a case where the light source for acquiring the front image and the light source for acquiring the tomographic image are shared has been described. However, the configuration according to the embodiments is limited thereto.

In the following, the tenth embodiment will be described with a focus on differences from the first embodiment.

Figure 40:
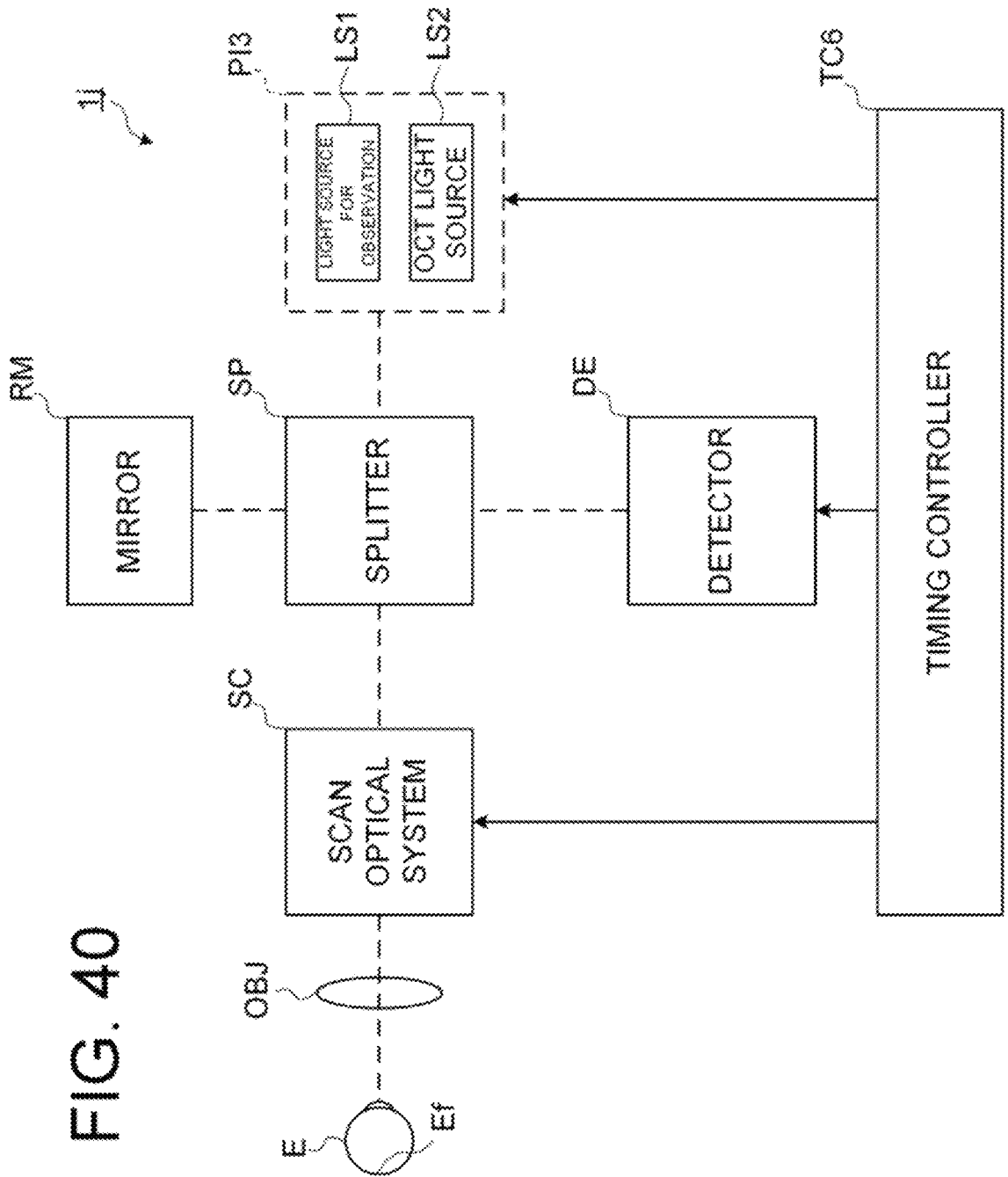
FIG. 40 is a schematic diagram illustrating an example of the configuration of an optical system of an ophthalmic apparatus according to a tenth embodiment.

FIG. 40 shows a block diagram of an example of a configuration of an ophthalmic apparatus 1j according to the tenth embodiment. In FIG. 40, like reference numerals designate like parts as in FIG. 1. The same description may not be repeated.

The configuration of an ophthalmic apparatus 1j according to the tenth embodiment is different from that of the ophthalmic apparatus 1 according to the first embodiment shown in FIG. 1 in that an the pattern illumination optical system PI3 is provided instead of the pattern illumination optical system PI.

The pattern illumination optical system PI3 includes a light source for observation LS1 and an OCT light source LS2. The light source for observation LS1 outputs light with a wavelength component in the visible region. The OCT light source LS2 outputs light with a wavelength component in the near-infrared region. The pattern illumination optical system PI3 switches between the output light from the light source for observation LS1 and the output light from the OCT light source LS2 to generate the slit-shaped illumination light similar to FIG. 1. In some embodiments, the pattern illumination optical system PI3 generates the slit-shaped illumination light similar to FIG. 1 from synthetic illumination light generated by simultaneously outputting the output light from the light source for observation LS1 and the output light from the OCT light source LS2. In this case, the light source for observation LS1, for example, outputs light with a wavelength component in the infrared region (a wavelength component that can be wavelength-separated with respect to the wavelength region of the output light from the OCT light source LS2). For example, in the same way as in the above embodiments, the detection result of the returning light of the output light from the light source for observation LS1 is obtained. For example, an observation image can be obtained by wavelength-separating the returning light of the output light from the light source for observation LS1 to detect it using the same method as in a conventional fundus camera.

The splitter SP guides the illumination light generated by the pattern illumination optical system PI3 into the illumination optical path (measurement optical path), and guides the reference light into the reference optical path. The scan optical system SC and the objective lens OBJ are arranged in the illumination optical path. The mirror RM is arranged in the reference optical path.

The illumination light that has been guided to the illumination optical path is deflected by the scan optical system SC.

The illumination light deflected by the scan optical system SC is refracted by the objective lens OBJ, enters into the eye through the pupil of the subject's eye E, and is irradiated onto the fundus Ef of the subject's eye E. The returning light of the illumination light irradiated onto the fundus Ef passes through the objective lens OBJ and the scan optical system SC, and enters the splitter SP.

The reference that has been guided to the reference optical path is reflected by the mirror RM, and returns to the splitter SP. The mirror RM can be moved along the optical path of the reference light.

The splitter SP generates the interference light (combined light) between the returning light of the illumination light from the subject's eye E passing through the illumination optical path and the reference light passing through the reference optical path. That is, the splitter SP guides the illumination light from the pattern illumination optical system PI3 to the scan optical system SC, and generates the interference light between the reference light and the returning light of the illumination light from the subject's eye E.

The detector DE detects the returning light of the illumination light from the subject's eye E passing through the illumination optical path and the interference light generated by the splitter SP, via the splitter SP. The detector DE can output the light receiving result using the rolling shutter method, the global shutter method, or the TDI method under the control from the timing controller TC5.

The timing controller TC5 controls at least the pattern illumination optical system PI3, the scan optical system SC, and the detector DE. The timing controller TC5 acquires the light reception result of the returning light or the combined light from the light receiving elements of the detector DE at the light receiving positions of the returning light corresponding to the irradiated positions, in synchronization with the movement timing of the irradiated positions of the illumination light, while moving the irradiated positions of the illumination light on the subject's eye by controlling the optical scan optical system SC.

[Actions]

The ophthalmic apparatus according to the embodiments will be described.

An ophthalmic apparatus (for example, ophthalmic apparatus 1) according to some embodiments includes an irradiation optical system (for example, pattern illumination optical system PI), an optical scanner (for example, optical scanner 30, scan optical system SC), an optical splitting and combining unit (for example, splitter SP), and a detector. The irradiation optical system includes a light source (wavelength swept light source, broadband light source) and is configured to generate measurement light (illumination light) using light from the light source. The optical scanner is configured to deflect the measurement light and to guide the deflected measurement light to a subject's eye (E). The optical splitting and combining unit is configured to guide the measurement light to the optical scanner and to generate interference light between reference light (split light) that is generated from the light from the light source and returning light of the measurement light from the subject's eye. The detector is configured to detect the returning light and the interference light via the optical splitting and combining unit.

According to such an aspect, the illumination light generated by the irradiation optical system using the light from the light source is guided to the optical scanner by the optical splitting and combining unit, and is deflected by the optical scanner, and is irradiated onto the subject's eye. The returning light of the illumination light from the subject's eye enters the optical splitting and combining unit. The optical splitting and combining unit generates the interference light between the returning light of the illumination light and the reference light generated from the light from the light source. The detector detects the returning light and the interference light via the optical splitting and combining unit. This allows to detect the returning light and the interference light for observing the subject's eye from various perspectives, while sharing the light source, the optical scanner, and the detector. As a result, an ophthalmic apparatus capable of observing the subject's eye in detail with a simple configuration can be provided.

An ophthalmic apparatus (for example, ophthalmic apparatus 1*b*) according to some embodiments includes an irradiation optical system (for example, pattern illumination optical system PI), an optical scanner (for example, optical scanner 30, scan optical system SC), an optical splitting and combining unit (for example, splitter SP), and a detector (for example, detector DE). The irradiation optical system includes a light source (wavelength swept light source, broadband light source) and is configured to generate measurement light (illumination light) using light from the light source. The optical scanner deflects the measurement light. The optical splitting and combining unit is configured to guide the measurement light deflected by the optical scanner to a subject's eye (E) and to generate interference light (split light) between reference light that is generated from the light from the light source and returning light of the measurement light from the subject's eye. The detector is configured to detect the returning light and the interference light via the optical splitting and combining unit.

According to such an aspect, the illumination light generated by the irradiation optical system using the light from the light source is deflected by the optical scanner, and is irradiated onto the subject's eye via the optical splitting and combining unit. The returning light of the illumination light from the subject's eye enters the optical splitting and combining unit. The optical splitting and combining unit generates the interference light between the returning light of the illumination light and the reference light generated from the light from the light source. The detector detects the returning light and the interference light via the optical splitting and combining unit. This allows to detect the returning light and the interference light for observing the subject's eye from various perspectives, while sharing the light source, the optical scanner, and the detector. As a result, an ophthalmic apparatus capable of observing the subject's eye in detail with a simple configuration can be provided.

In some embodiments, the irradiation optical system is configured to split the light from the light source into the measurement light and the reference light.

According to such an aspect, the reference light can be generated by dividing the power or the wavelength range. This allows for a simpler configuration of the ophthalmic apparatus.

In some embodiments, the irradiation optical system is configured to output the measurement light and the reference light by switching an optical path of the light from the light source.

According to such an aspect, the measurement light and the reference light can be generated by switching the optical path. This allows for a simpler configuration of the ophthalmic apparatus.

In some embodiments, the ophthalmic apparatus further includes a light-shielding plate (for example, light-shielding plate SHD, 80) configured to be capable of inserting and removing from at least one optical path of the measurement light and the reference light. The detector is configured to detect the returning light with the light-shielding plate arranged in the at least one optical path and to detect the interference light with the light-shielding plate removed from the at least one optical path.

According to such an aspect, when the light-shield plate is arranged in optical paths for at least one of the measurement light and the reference light, the optical splitting and combining unit guides the returning light to the detector. When the light-shielding plate is removed from the optical paths for at least one of the measurement light and the reference light, the optical splitting and composing unit guides the interference light to the detector. This allows to detect the returning light and the interference light using a single detector. Therefore, this allows for a simpler configuration of the ophthalmic apparatus.

In some embodiments, the optical splitting and combining unit includes: an optical splitter (for example, perforated mirror PM) configured to split an optical path of the measurement light and an optical path of the returning light; a first splitter (for example, splitter BS) configured to split the returning light split by the optical splitter into first returning light and second returning light; and a beam combiner (for example, beam combiner BC) configured to generate interference light between the reference light and the second returning light. The detector is configured to detect the first returning light split by the first splitter and the interference light generated by the beam combiner.

According to such an aspect, the detector detects the first returning light and the interference light between the reference light and the second returning light. Here, the first returning light is acquired by splitting the returning light using the first splitter, and the second returning light is acquired by splitting the returning light using the first splitter. Thereby, the first returning light and the interference light can be generated with a simple configuration. As a result, this allows for a simpler configuration of the ophthalmic apparatus.

In some embodiments, the optical splitter includes a perforated mirror (for example, perforated mirror PM, 45) with a hole that an optical axis passes through. the hole is arranged at a position substantially conjugate optically to an iris of the subject's eye.

According to such an aspect, it enables pupil division between the illumination light and the returning light with a simple configuration. Thereby, sufficient light amount of the illumination light entering the eye and sufficient light amount of returning light of the illumination light from the subject's eye can be ensured. As a result, an ophthalmic apparatus capable of acquiring high-definition images or high-precision measurement signals can be provided.

In some embodiments, the detector includes a first detector (for example, SLO detector DS) configured to detect the first returning light; and a second detector (for example, OCT detector DO) configured to detect the interference light.

According to such an aspect, the first returning light and the interference light can be detected in parallel. Thereby, while simplifying the configuration, an ophthalmic apparatus capable of observing the site of interest in the subject's eye in detail in a short time can be provided.

In some embodiments, the optical splitting and combining unit includes a first optical path length changing unit (for example, mirrors Ma, Mb, and RM) arranged between the first splitter and the beam combiner and configured to change an optical path length of the second returning light.

According to such an aspect, an ophthalmic apparatus capable of changing the difference between the optical path length of the measurement light and the optical path length of the reference light can be provided.

In some embodiments, the optical splitting and combining unit includes a second optical path length changing unit (for example, mirrors Ma, Mb, and RM) arranged on an optical path of the reference light and configured to change an optical path length of the reference light.

According to such an aspect, an ophthalmic apparatus capable of changing the difference between the optical path length of the measurement light and the optical path length of the reference light can be provided.

In some embodiments, the ophthalmic apparatus further includes a first image forming unit (for example, SLO image forming unit 210) configured to form a front image (SLO image) of the subject's eye based on a detection result of the returning light obtained by the detector; and a second image forming unit (for example, OCT image forming unit 220) configured to form a tomographic image (OCT image) of the subject's eye based on a detection result of the interference light obtained by the detector.

According to such an aspect, the front image and the tomographic image of the subject's eye can be obtained. Thereby, an ophthalmic apparatus capable of observing the subject's eye in detail can be provided.

In some embodiments, the light source includes a wavelength swept light source.

According to such an aspect, an ophthalmic apparatus capable of acquiring the tomographic image of the subject's eye by performing swept source type OCT can be provided.

In some embodiments, the light source includes a broadband light source, and the detector includes a spectrometer (for example, spectrometer SPO) that disperses the interference light.

According to such an aspect, an ophthalmic apparatus capable of acquiring the tomographic image of the subject's eye by performing spectral domain type OCT can be provided.

In some embodiments, the irradiation optical system is configured to generate slit-shaped measurement light using the light from the light source. The ophthalmic apparatus further includes a controller (for example, controller 100) configured to control the detector using a rolling shutter method so as to acquire light receiving result of the returning light corresponding to an irradiated position of the measurement light in a measurement site of the subject's eye.

According to such an aspect, by using the rolling shutter method, without being affected by unnecessary scattered light, an ophthalmic apparatus capable of acquiring high quality images of the subject's eye with strong contrast with a simple configuration can be provided.

In some embodiments, the irradiation optical system includes: a slit (for example, slit 22) with a slit-shaped aperture capable of being arranged at a position substantially conjugate optically to the measurement site; and an iris aperture (for example, iris aperture 21) arranged between the light source and the slit, and configured to be capable of being arranged at a position substantially conjugate optically to an iris of the subject's eye.

According to such an aspect, the illumination light and the returning light of the illumination light can be pupil-divided. Thereby, the illumination intensity required for measuring the site of interest can be secured with a simple configuration. As a result, an ophthalmic apparatus capable of acquiring high quality images of the subject's eye can be provided.

In some embodiments, the ophthalmic apparatus further includes a first movement mechanism (for example, movement mechanism 22D) configured to move the slit in an optical axis direction of the irradiation optical system. The controller is configured to control the first movement mechanism based on a dioptric power of the subject's eye.

According to such an aspect, the slit is moved according to the dioptric power of the subject's eye. Thereby, the illumination light can be efficiently guided to the site of interest in the subject's eye. As a result, even when an inexpensive light source with a wide spread angle is used, the illumination intensity required for measurement of the site of interest can be secured with a simple configuration. And this allows to acquire high quality images of the subject's eye without being affected by the condition of the subject's eye.

In some embodiments, the ophthalmic apparatus further includes a second movement mechanism (movement mechanism 10D) configured to change at least one of a position of the light source or an orientation of the light source. The controller is configured to control the second movement mechanism according to the position of the slit moved by the first movement mechanism.

According to such an aspect, even when the positional relationship between the light source and the slit is changed according to the dioptric power of the subject's eye, the light intensity distribution in a direction connecting the light source and the aperture(s) of the slit can be changed. As a result, the site of interest of the subject's eye can be illuminated with a desired illumination intensity, without being affected by the dioptric power of the subject's eye.

In some embodiments, the irradiation optical system includes a first relay lens system (for example, relay lens system RL1) arranged between the optical scanner and the slit. A back focal position of the first relay lens system is a position substantially conjugate optically to the iris.

According to such an aspect, the optical system from the first relay lens system to the iris of the subject's eye can be configured according to the Badal's principle. Thereby, even when the slit is moved in the optical axis direction in accordance with the dioptric power of the subject's eye, the size of the slit image project onto a site of interest of the subject's eye does not change, regardless of the dioptric power of the subject's eye. This means that the projection magnification of the slit image onto the site of interest does not change even when the slit moves in the optical axis direction. As a result, regardless of the dioptric power of the subject's eye, this allows to keep the deflection operation speed of the optical scanner constant, and to simplify the control of the optical scanner. In addition, since the projected angle of view (projection magnification) of the slit image with reference to the visual axis of the subject's eye is constant regardless of the dioptric power of the subject's eye, the illumination intensity of the slit image at the site of interest can be kept constant regardless of the dioptric power of the subject's eye. Further, in case of acquiring images at a predetermined imaging angle of view in the ophthalmic apparatus, since the projection magnification is constant, this eliminates the need for a margin longitudinal length of the slit provided to acquire a slit image of a predetermined size.

In some embodiments, the optical scanner is arranged at the back focal position or the vicinity of the back focal position.

According to such an aspect, regardless of the dioptric power of the subject's eye, this allows to keep the deflection operation speed of the optical scanner constant while reducing the size of the optical system, and to simplify the control of the optical scanner.

In some embodiments, the ophthalmic apparatus further includes a second relay lens system (relay lens system RL2) arranged between the slit and the iris aperture. The iris aperture is arranged at a front focal position of the second relay lens system or the vicinity of the front focal position of the second relay lens system.

According to such an aspect, by changing the focal distance of the first relay lens system or the focal distance of the second relay lens system, the projection magnification from the iris aperture to the optical scanner can be changed. Thereby, the image of the iris aperture with any size can be projected onto the optical scanner with a desired size. This allows to project the image of the iris aperture with the desired size onto the optical scanner even when the size of the emitting surface of the light source is different, and to improve the degree of freedom in designing optical systems.

In some embodiments, one or more apertures that the measurement light passes through are formed in the iris aperture so that luminous flux cross section of the measurement light and luminous flux cross section of returning light from the subject's eye are separated on a cornea of the subject's eye, an anterior surface of lens of the subject's eye, and a posterior surface of lens of the subject's eye.

According to such an aspect, by pupil-dividing the illumination light incident on the subject's eye and the returning light from the subject's eye with a high degree of accuracy, the illumination required for measuring the site of interest of the subject's eye can be secured and high quality image of the subject's eye can be acquired, with a simple configuration, without being affected by the state of the subject's eye.

In some embodiments, each of the one or more apertures has a circular segment shape, and a direction of a chord of the circular segment shape is approximately parallel to a longitudinal direction of a slit image formed by light passing through the slit.

According to such an configuration, the light amount of illumination light can be increased and high quality images with stronger contrast can be acquired, with a simple configuration.

The above-described some embodiments or the modification examples thereof are merely examples for carrying out the present invention. Those who intend to implement the present invention can apply any modification, omission, addition, or the like within the scope of the gist of the present invention.

In the above embodiments, the ophthalmic apparatus may have arbitrary functions adaptable in the field of ophthalmology. Examples of such functions include a axial length measurement function, a tonometry function, an optical coherence tomography (OCT) function, an ultrasonic inspection, and the like. It should be noted that the axial length measurement function is realized by the OCT, etc. Further, the axial length measurement function may be used to measure the axial length of the subject's eye by projecting light onto the subject's eye and detecting the returning light from the fundus while adjusting the position of the optical system in the Z direction (front-back direction) relative to the subject's eye. The tonometry measurement function is realized by the tonometer, etc. The OCT function is realized by the OCT apparatus, etc. The ultrasonic inspection function is realized by the ultrasonic diagnosis apparatus, etc. Further, the present invention can also be applied to an apparatus (multifunctional apparatus) having two or more of such functions.

In some embodiments, a program for causing a computer to execute the method of controlling the ophthalmic apparatus described above is provided. Such a program can be stored in any non-transitory computer-readable recording medium. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

The configurations described in the first embodiment to the tenth embodiment and the modification example of the first embodiment can be combined as desired.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What claimed is:

1. An ophthalmic apparatus, comprising:
   an irradiation optical system including a light source and configured to generate measurement light using light from the light source;
   an optical scanner configured to deflect the measurement light and to guide the deflected measurement light to a subject's eye;
   an optical splitting and combining unit configured to guide the measurement light to the optical scanner and to generate interference light between reference light that is generated from the light from the light source and returning light of the measurement light from the subject's eye; and a detector configured to detect the returning light and the interference light via the optical splitting and combining unit, wherein the irradiation optical system is configured to generate slit-shaped measurement light using the light from the light source, the ophthalmic apparatus further includes a controller configured to control the detector using a rolling shutter method so as to acquire light receiving result of the returning light corresponding to an irradiated position of the measurement light in a measurement site of the subject's eye, the irradiation optical system includes a slit with a slit-shaped aperture capable of being arranged at a position substantially conjugate optically to the measurement site, and an iris aperture arranged between the light source and the slit, and configured to be capable of being arranged at a position substantially conjugate optically to an iris of the subject's eye, and the ophthalmic apparatus further comprising:

a first movement mechanism configured to move the slit in an optical axis direction of the irradiation optical system, wherein the controller is configured to control the first movement mechanism based on a dioptric power of the subject's eye.

2. The ophthalmic apparatus of claim 1, wherein the irradiation optical system is configured to split the light from the light source into the measurement light and the reference light.

3. The ophthalmic apparatus of claim 2, wherein the optical splitting and combining unit includes a second optical path length changing unit arranged on an optical path of the reference light and configured to change an optical path length of the reference light.

4. The ophthalmic apparatus of claim 1, wherein the irradiation optical system is configured to output the measurement light and the reference light by switching an optical path of the light from the light source.

5. The ophthalmic apparatus of claim 1, further comprising a light-shielding plate configured to be capable of inserting and removing from at least one optical path of the measurement light and the reference light, wherein the detector is configured to detect the returning light with the light-shielding plate arranged in the at least one optical path and to detect the interference light with the light-shielding plate removed from the at least one optical path.

6. The ophthalmic apparatus of claim 1, wherein the optical splitting and combining unit includes:

an optical splitter configured to split an optical path of the measurement light and an optical path of the returning light;

a first splitter configured to split the returning light split by the optical splitter into first returning light and second returning light; and a beam combiner configured to generate interference light between the reference light and the second returning light, wherein the detector is configured to detect the first returning light split by the first splitter and the interference light generated by the beam combiner.

7. The ophthalmic apparatus of claim 6, wherein the optical splitter includes a perforated mirror with a hole that an optical axis passes through, and the hole is arranged at a position substantially conjugate optically to an iris of the subject's eye.

8. The ophthalmic apparatus of claim 6, wherein the detector includes:

a first detector configured to detect the first returning light; and a second detector configured to detect the interference light.

9. The ophthalmic apparatus of claim 6, wherein the optical splitting and combining unit includes a first optical path length changing unit arranged between the first splitter and the beam combiner and configured to change an optical path length of the second returning light.

10. The ophthalmic apparatus of claim 1, further comprising:

a first image forming unit configured to form a front image of the subject's eye based on a detection result of the returning light obtained by the detector; and a second image forming unit configured to form a tomographic image of the subject's eye based on a detection result of the interference light obtained by the detector.

11. The ophthalmic apparatus of claim 1, wherein the light source includes a wavelength swept light source.

12. The ophthalmic apparatus of claim 1, wherein the light source includes a broadband light source, and the detector includes a spectrometer that disperses the interference light.

13. The ophthalmic apparatus of claim 1, further comprising a second movement mechanism configured to change at least one of a position of the light source or an orientation of the light source, wherein the controller is configured to control the second movement mechanism according to the position of the slit moved by the first movement mechanism.

14. The ophthalmic apparatus of claim 1, wherein the irradiation optical system includes a first relay lens system arranged between the optical scanner and the slit, and a back focal position of the first relay lens system is a position substantially conjugate optically to the iris.

15. The ophthalmic apparatus of claim 14, wherein the optical scanner is arranged at the back focal position or the vicinity of the back focal position.

16. An ophthalmic apparatus, comprising:

an irradiation optical system including a light source and configured to generate measurement light using light from the light source;

an optical scanner configured to deflect the measurement light;

an optical splitting and combining unit configured to guide the measurement light deflected by the optical scanner to a subject's eye and to generate interference light between reference light that is generated from the light from the light source and returning light of the measurement light from the subject's eye; and a detector configured to detect the returning light and the interference light via the optical splitting and combining unit, wherein the irradiation optical system is configured to generate slit-shaped measurement light using the light from the light source, the ophthalmic apparatus further includes a controller configured to control the detector using a rolling shutter method so as to acquire light receiving result of the returning light corresponding to an irradiated position of the measurement light in a measurement site of the subject's eye, the irradiation optical system includes a slit with a slit-shaped aperture capable of being arranged at a position substantially conjugate optically to the measurement site, and an iris aperture arranged between the light source and the slit, and configured to be capable of being arranged at a position substantially conjugate optically to an iris of the subject's eye, and the ophthalmic apparatus further comprising:

a first movement mechanism configured to move the slit in an optical axis direction of the irradiation optical system, wherein the controller is configured to control the first movement mechanism based on a dioptric power of the subject's eye.

17. The ophthalmic apparatus of claim 16, wherein
the irradiation optical system is configured to split the light from the light source into the measurement light and the reference light.

18. The ophthalmic apparatus of claim 16, wherein
the irradiation optical system is configured to output the measurement light and the reference light by switching an optical path of the light from the light source.

19. The ophthalmic apparatus of claim 16, further comprising
a light-shielding plate configured to be capable of inserting and removing from at least one optical path of the measurement light and the reference light, wherein
the detector is configured to detect the returning light with the light-shielding plate arranged in the at least one optical path and to detect the interference light with the light-shielding plate removed from the at least one optical path.

20. The ophthalmic apparatus of claim 16, wherein
the optical splitting and combining unit includes:
an optical splitter configured to split an optical path of the measurement light and an optical path of the returning light;
a first splitter configured to split the returning light split by the optical splitter into first returning light and second returning light; and
a beam combiner configured to generate interference light between the reference light and the second returning light, wherein
the detector is configured to detect the first returning light split by the first splitter and the interference light generated by the beam combiner.

21. The ophthalmic apparatus of claim 20, wherein
the optical splitter includes a perforated mirror with a hole that an optical axis passes through, and
the hole is arranged at a position substantially conjugate optically to an iris of the subject's eye.

22. An ophthalmic apparatus, comprising:
an irradiation optical system including a light source and configured to generate measurement light using light from the light source;
an optical scanner configured to deflect the measurement light and to guide the deflected measurement light to a subject's eye;
an optical splitting and combining unit configured to guide the measurement light to the optical scanner and to generate interference light between reference light that is generated from the light from the light source and returning light of the measurement light from the subject's eye; and a detector configured to detect the returning light and the interference light via the optical splitting and combining unit, wherein
the irradiation optical system is configured to generate slit-shaped measurement light using the light from the light source,
the ophthalmic apparatus further includes a controller configured to control the detector using a rolling shutter method so as to acquire light receiving result of the returning light corresponding to an irradiated position of the measurement light in a measurement site of the subject's eye,
the irradiation optical system includes a slit with a slit-shaped aperture capable of being arranged at a position substantially conjugate optically to the measurement site, and an iris aperture arranged between the light source and the slit, and configured to be capable of being arranged at a position substantially conjugate optically to an iris of the subject's eye, and
the ophthalmic apparatus further comprising:
a second relay lens system arranged between the slit and the iris aperture, wherein
the iris aperture is arranged at a front focal position of the second relay lens system or the vicinity of the front focal position of the second relay lens system.

23. An ophthalmic apparatus, comprising:
an irradiation optical system including a light source and configured to generate measurement light using light from the light source;
an optical scanner configured to deflect the measurement light and to guide the deflected measurement light to a subject's eye;
an optical splitting and combining unit configured to guide the measurement light to the optical scanner and to generate interference light between reference light that is generated from the light from the light source and returning light of the measurement light from the subject's eye; and
a detector configured to detect the returning light and the interference light via the optical splitting and combining unit, wherein
the irradiation optical system is configured to generate slit-shaped measurement light using the light from the light source,
the ophthalmic apparatus further includes a controller configured to control the detector using a rolling shutter method so as to acquire light receiving result of the returning light corresponding to an irradiated position of the measurement light in a measurement site of the subject's eye,
the irradiation optical system includes a slit with a slit-shaped aperture capable of being arranged at a position substantially conjugate optically to the measurement site, and an iris aperture arranged between the light source and the slit, and configured to be capable of being arranged at a position substantially conjugate optically to an iris of the subject's eye, and
one or more apertures that the measurement light passes through are formed in the iris aperture so that luminous flux cross section of the measurement light and luminous flux cross section of returning light from the subject's eye are separated on a cornea of the subject's eye, an anterior surface of lens of the subject's eye, and a posterior surface of lens of the subject's eye.

24. The ophthalmic apparatus of claim 23, wherein
each of the one or more apertures has a circular segment shape, and a direction of a chord of the circular segment shape is approximately parallel to a longitudinal direction of a slit image formed by light passing through the slit.

25. An ophthalmic apparatus, comprising:
an irradiation optical system including a light source and configured to generate measurement light using light from the light source;
an optical scanner configured to deflect the measurement light;
an optical splitting and combining unit configured to guide the measurement light deflected by the optical scanner to a subject's eye and to generate interference light between reference light that is generated from the light from the light source and returning light of the measurement light from the subject's eye; and
a detector configured to detect the returning light and the interference light via the optical splitting and combining unit, wherein
the irradiation optical system is configured to generate slit-shaped measurement light using the light from the light source,
the ophthalmic apparatus further includes a controller configured to control the detector using a rolling shutter method so as to acquire light receiving result of the returning light corresponding to an irradiated position of the measurement light in a measurement site of the subject's eye,
the irradiation optical system includes a slit with a slit-shaped aperture capable of being arranged at a position substantially conjugate optically to the measurement site, and an iris aperture arranged between the light source and the slit, and configured to be capable of being arranged at a position substantially conjugate optically to an iris of the subject's eye, and
the ophthalmic apparatus further comprising:
a second relay lens system arranged between the slit and the iris aperture, wherein
the iris aperture is arranged at a front focal position of the second relay lens system or the vicinity of the front focal position of the second relay lens system.

26. An ophthalmic apparatus, comprising:
an irradiation optical system including a light source and configured to generate measurement light using light from the light source;
an optical scanner configured to deflect the measurement light;
an optical splitting and combining unit configured to guide the measurement light deflected by the optical scanner to a subject's eye and to generate interference light between reference light that is generated from the light from the light source and returning light of the measurement light from the subject's eye; and
a detector configured to detect the returning light and the interference light via the optical splitting and combining unit, wherein
the irradiation optical system is configured to generate slit-shaped measurement light using the light from the light source,
the ophthalmic apparatus further includes a controller configured to control the detector using a rolling shutter method so as to acquire light receiving result of the returning light corresponding to an irradiated position of the measurement light in a measurement site of the subject's eye,
the irradiation optical system includes a slit with a slit-shaped aperture capable of being arranged at a position substantially conjugate optically to the measurement site, and an iris aperture arranged between the light source and the slit, and configured to be capable of being arranged at a position substantially conjugate optically to an iris of the subject's eye, and
one or more apertures that the measurement light passes through are formed in the iris aperture so that luminous flux cross section of the measurement light and luminous flux cross section of returning light from the subject's eye are separated on a cornea of the subject's eye, an anterior surface of lens of the subject's eye, and a posterior surface of lens of the subject's eye.

* * * * *